US012661464B2

(12) United States Patent
Payton et al.

(10) Patent No.: US 12,661,464 B2
(45) Date of Patent: Jun. 23, 2026

(54) FLOW THERAPY SYSTEM AND METHOD

(71) Applicant: Fisher & Paykel Healthcare Limited, Auckland (NZ)

(72) Inventors: Matthew Jon Payton, Auckland (NZ); Thomas Heinrich Barnes, Auckland (NZ); Anil Patel, London (GB); Seyed Ahmad Reza Nouraei, London (GB); Jonathan Mark Cousins, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 915 days.

(21) Appl. No.: 17/766,141

(22) PCT Filed: Oct. 8, 2020

(86) PCT No.: PCT/NZ2020/050122
§ 371 (c)(1),
(2) Date: Apr. 1, 2022

(87) PCT Pub. No.: WO2021/071366
PCT Pub. Date: Apr. 15, 2021

(65) Prior Publication Data
US 2022/0401676 A1 Dec. 22, 2022

Related U.S. Application Data

(60) Provisional application No. 62/912,373, filed on Oct. 8, 2019.

(51) Int. Cl.
A61M 16/00 (2006.01)
A61B 5/00 (2006.01)
(Continued)

(52) U.S. Cl.
CPC ......... A61M 16/026 (2017.08); A61B 5/0205 (2013.01); A61B 5/0826 (2013.01);
(Continued)

(58) Field of Classification Search
CPC .......... A61M 16/0057; A61M 16/0066; A61M 16/0069; A61M 16/01; A61M 16/024;
(Continued)

(56) References Cited

U.S. PATENT DOCUMENTS 6,223,064 B1 4/2001 Lynn et al.
7,201,734 B2 4/2007 Hickle
(Continued)

FOREIGN PATENT DOCUMENTS

WO WO 1994/004071 3/1994
WO WO 2010/053845 5/2010
(Continued)

OTHER PUBLICATIONS

Rivas et al., Ventilation/Perfusion distribution abnormalities in morbidly obese subjects before and after bariatric surgery. Chest. Apr. 2015;147(4):1127-1134. doi: 10.1378/chest.14-1749.*
(Continued)

*Primary Examiner* — Joseph D. Boecker
(74) *Attorney, Agent, or Firm* — Knobbe, Martens, Olson & Bear, LLP

(57) ABSTRACT

A method of determining a duration of safe apnoea. Information is obtained relating to a respiratory indicator, which can include information relating to a potential respiratory equilibrium, and a duration of safe apnoea is determined from the obtained information.

21 Claims, 18 Drawing Sheets

(51) Int. Cl.

| | |
|---|---|
| *A61B 5/0205* | (2006.01) |
| *A61B 5/08* | (2006.01) |
| *A61B 5/097* | (2006.01) |
| *A61B 5/145* | (2006.01) |
| *A61M 16/01* | (2006.01) |
| *A61M 16/12* | (2006.01) |
| *G16H 20/40* | (2018.01) |
| *G16H 50/20* | (2018.01) |
| *G16H 50/30* | (2018.01) |

(52) U.S. Cl.
CPC .......... *A61B 5/097* (2013.01); *A61B 5/14542* (2013.01); *A61B 5/4836* (2013.01); *A61M 16/01* (2013.01); *G16H 20/40* (2018.01); *G16H 50/20* (2018.01); *G16H 50/30* (2018.01); *A61B 5/082* (2013.01); *A61M 16/12* (2013.01); *A61M 2202/0208* (2013.01); *A61M 2202/0225* (2013.01); *A61M 2205/3334* (2013.01); *A61M 2230/08* (2013.01); *A61M 2230/202* (2013.01); *A61M 2230/205* (2013.01)

(58) Field of Classification Search
CPC .......... A61M 16/026; A61M 2230/005; A61M 2230/202; A61M 2230/205; A61M 2230/30; A61M 2230/432; A61M 2230/435; A61B 5/0205; A61B 5/0826; A61B 5/0935; A61B 5/097; A61B 5/4836
See application file for complete search history.

(56) References Cited

U.S. PATENT DOCUMENTS

| | | | |
|---|---|---|---|
| 8,028,694 | B2 | 10/2011 | Hickle |
| 8,545,416 | B1 | 10/2013 | Kayyali et al. |
| 8,670,811 | B2 | 3/2014 | O-Reilly |
| 9,636,056 | B2 | 5/2017 | Ai-Ali |
| RE47,353 | E | 4/2019 | Kiani |
| 10,588,518 | B2 | 3/2020 | Kiani |
| 10,918,341 | B2 | 2/2021 | Al-Ali et al. |
| 10,973,466 | B2 | 4/2021 | Payton et al. |
| 10,987,066 | B2 | 4/2021 | Chandran |
| 2006/0169281 | A1 | 8/2006 | Aylsworth et al. |
| 2007/0175473 | A1 | 8/2007 | Lewis et al. |
| 2008/0236582 | A1 | 10/2008 | Tehrani |
| 2009/0299430 | A1 | 12/2009 | Davies et al. |
| 2011/0006901 | A1 | 1/2011 | Lellouche et al. |
| 2011/0067697 | A1 | 3/2011 | Lellouche et al. |
| 2013/0201020 | A1 | 8/2013 | Covidien |
| 2013/0253359 | A1 | 9/2013 | Emtell et al. |
| 2015/0248290 | A1 | 9/2015 | Gschwind et al. |
| 2015/0258290 | A1 | 9/2015 | Landwehr |
| 2018/0085544 | A1* | 3/2018 | Holyoake ......... A61M 16/0616 |
| 2018/0104426 | A1* | 4/2018 | Oldfield .............. A61M 16/024 |
| 2018/0126110 | A1* | 5/2018 | Payton ................ A61M 16/104 |
| 2018/0280641 | A1* | 10/2018 | White ............... A61M 16/0096 |
| 2018/0311454 | A1 | 11/2018 | Klein et al. |
| 2019/0224434 | A1* | 7/2019 | Silver .................. A61N 1/3925 |
| 2020/0261675 | A1 | 8/2020 | Rehman et al. |
| 2021/0022676 | A1 | 1/2021 | Lamego et al. |
| 2021/0138172 | A1 | 5/2021 | Evans et al. |
| 2021/0244365 | A1 | 8/2021 | Assouad |
| 2023/0173208 | A1 | 6/2023 | Evans et al. |

FOREIGN PATENT DOCUMENTS

| | | | | |
|---|---|---|---|---|
| WO | WO 2013/158791 | 10/2013 | | |
| WO | WO2016/133406 | 8/2016 | | |
| WO | WO2016/157106 | 10/2016 | | |
| WO | WO2018/136821 | 7/2018 | | |
| WO | WO2018/185714 | 10/2018 | | |
| WO | WO-2018185714 A1 * | 10/2018 | .......... | A61B 5/0826 |
| WO | WO2019/070136 | 4/2019 | | |
| WO | WO 2019/089655 | 5/2019 | | |
| WO | WO 2021/202465 | 10/2021 | | |

OTHER PUBLICATIONS

F. R. Altermatt, H. R. Muñoz, A. E. Delfino, L. I. Cortínez, Pre-oxygenation in the obese patient: effects of position on tolerance to apnoea, BJA: British Journal of Anaesthesia, vol. 95, Issue 5, Nov. 2005, pp. 706-709, https://doi.org/10.1093/bja/aei231.*

Bouroche G, Bourgain JL. Preoxygenation and general anesthesia: a review. Minerva Anestesiol. Aug. 2015;81(8):910-20. Epub Jun. 5, 2015. PMID: 26044934.*

Elena Bignami, Francesco Saglietti, Alessandro Girombelli, Andrea Briolini, Tiziana Bove, Luigi Vetrugno, Preoxygenation during induction of anesthesia in non-critically ill patients: A systematic review, Journal of Clinical Anesthesia, vol. 52, 2019, pp. 85-90, https://doi.org/10.1016/j.jclinane.2018.09.008.*

Bouroche et al., "Preoxygenation and general anesthesia: a review", Minerva Anestesiologica, 2015; 81:910-20, published in Aug. 2015.

Benumof, Jonathan L. et al., "Critical hemoglobin desaturation will occur before return to an unparalyzed state following 1 mg/kg intravenous succinylcholine", Anesthesiology: The Journal of the American Society of Anesthesiologists, Oct. 1997, vol. 87, No. 4, pp. 979-982.

Biffen, Andrew et al., "Apnoea and Pre-Oxygenation"—Anaesthesia tutorial of the Week 297, Nov. 4, 2013, pp. 1-7.

Farmery, A.D. et al., "A model to describe the rate of oxyhaemoglobin desaturation during apnoea", British Journal of Anaesthesia, 1996, vol. 76, No. 2, pp. 284-291.

Rajan, S. et al., 2018, Effects of Preoxygenation with Tidal Volume Breathing Followed by Apneic Oxygenation with and without Continuous Positive Airway Pressure on Duration of Safe Apnea Time and Arterial Blood Gases, Anesthesia: Essays and Researches, 12(1):229-233.

Sands et al., Dec. 4, 2009, A Model Analysis of Arterial Oxygen Desaturation during Apnea in Preterm Infants, PLOS Computational Biology, 5(12):e1000588.

* cited by examiner

600

602 — Measure SpO$_2$ and PaO$_2$ at set times

604 — Determine PaO$_2$ value that relates to minimum safe value of SpO$_2$

606 — Determine time remaining until PaO$_2$ is reached

SpO$_2$ (%)

PaO$_2$ (mmHg)

SpO$_2$ (%)

PaO$_2$ (mmHg)

PaO$_2$

SpO$_2$

T1

1000

1002 — Measure physical and/or physiological parameters(s)

1004 — Predict desaturation equilibrium and duration of safe apnoea

1006 — Provide information to clinician based on prediction

1008 — Monitor patient during procedure and refine equilibrium and duration of safe apnoea determinations 1010 — Control respiratory therapy

Typical Patient (e.g., Normal BMI) with Respiratory Equilibrium Between 95-100% SpO$_2$

Atypical Patient (e.g., High BMI) with Respiratory Equilibrium of About 85% SpO$_2$

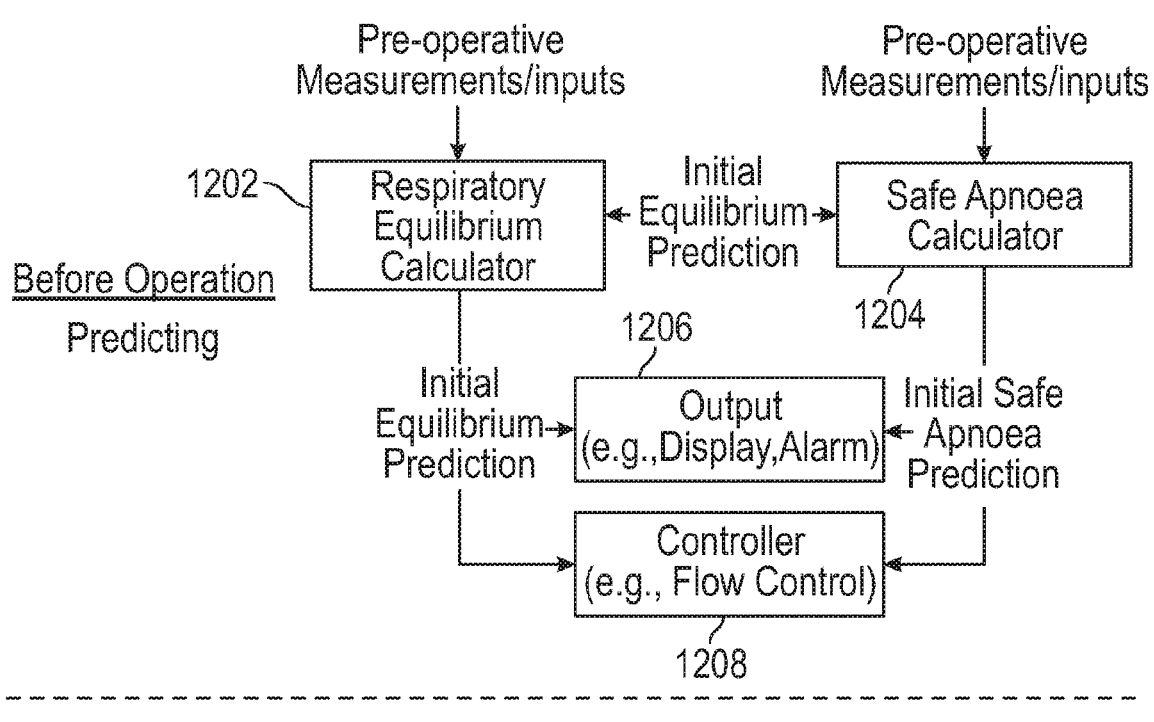
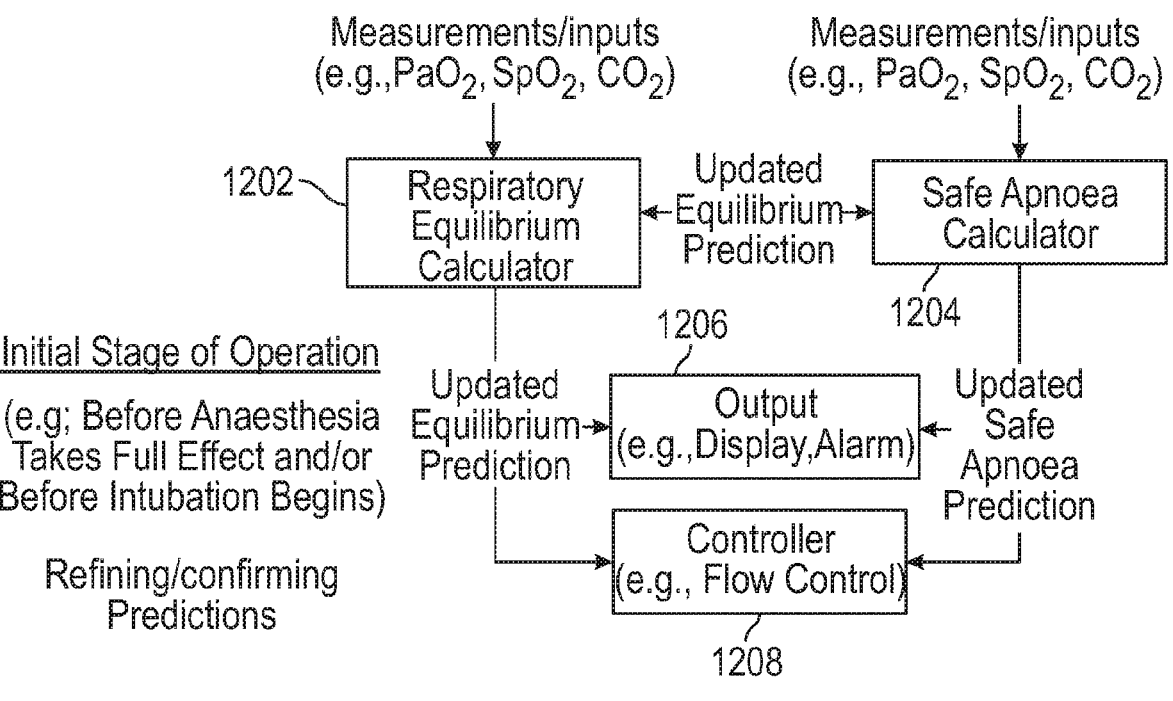
FIG. 12

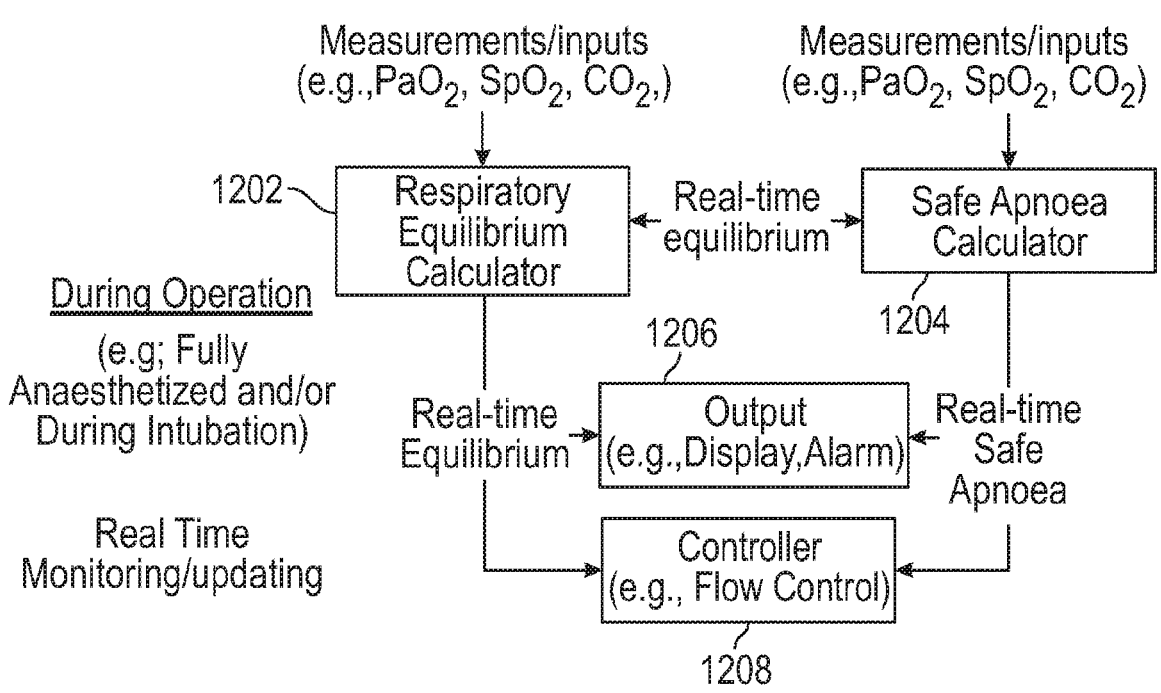

1220

Measurements/inputs
(e.g.,$PaO_2$, $SpO_2$, $CO_2$,)

Measurements/inputs
(e.g.,$PaO_2$, $SpO_2$, $CO_2$)

1202 — Respiratory Equilibrium Calculator

Real-time equilibrium

Safe Apnoea Calculator

<u>During Operation</u>

(e.g; Fully Anaesthetized and/or During Intubation)

Real Time Monitoring/updating

Real-time Equilibrium

1206

Output (e.g.,Display,Alarm)

Real-time Safe Apnoea

1204

Controller (e.g., Flow Control)

Upper Respiratory Region

Lower Respiratory Region

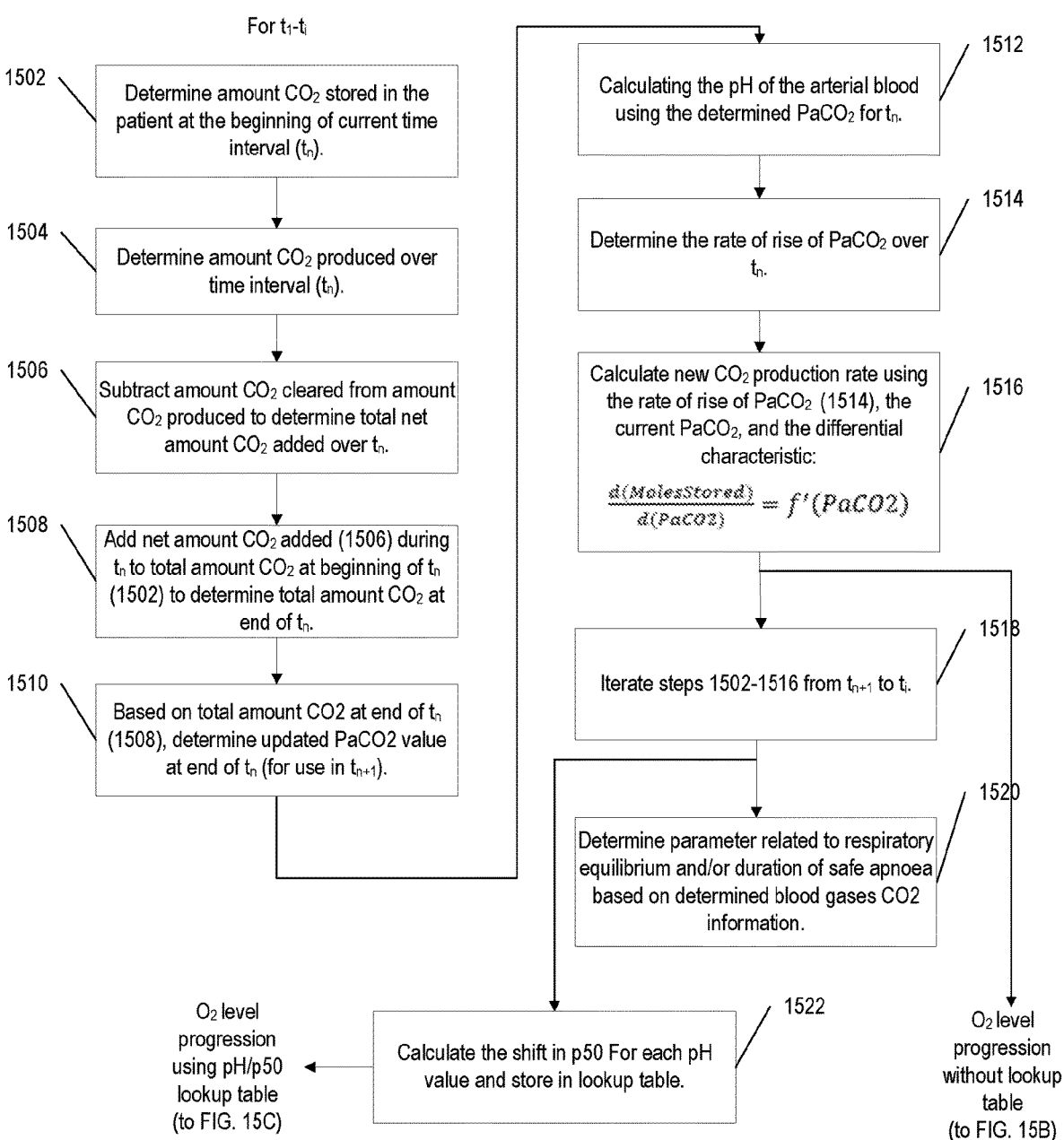

For $t_1$-$t_i$

1502 — Determine amount $CO_2$ stored in the patient at the beginning of current time interval ($t_n$).

1504 — Determine amount $CO_2$ produced over time interval ($t_n$).

1506 — Subtract amount $CO_2$ cleared from amount $CO_2$ produced to determine total net amount $CO_2$ added over $t_n$.

1508 — Add net amount $CO_2$ added (1506) during $t_n$ to total amount $CO_2$ at beginning of $t_n$ (1502) to determine total amount $CO_2$ at end of $t_n$.

1510 — Based on total amount CO2 at end of $t_n$ (1508), determine updated PaCO2 value at end of $t_n$ (for use in $t_{n+1}$).

1512 — Calculating the pH of the arterial blood using the determined PaCO2 for $t_n$.

1514 — Determine the rate of rise of PaCO2 over $t_n$.

1516 — Calculate new $CO_2$ production rate using the rate of rise of PaCO2 (1514), the current PaCO2, and the differential characteristic:

$$\frac{d(MolesStored)}{d(PaCO2)} = f'(PaCO2)$$

1518 — Iterate steps 1502-1516 from $t_{n+1}$ to $t_i$.

1520 — Determine parameter related to respiratory equilibrium and/or duration of safe apnoea based on determined blood gases CO2 information.

1522 — Calculate the shift in p50 For each pH value and store in lookup table.

O2 level progression using pH/p50 lookup table (to FIG. 15C)

O2 level progression without lookup table (to FIG. 15B)

FIG. 15A

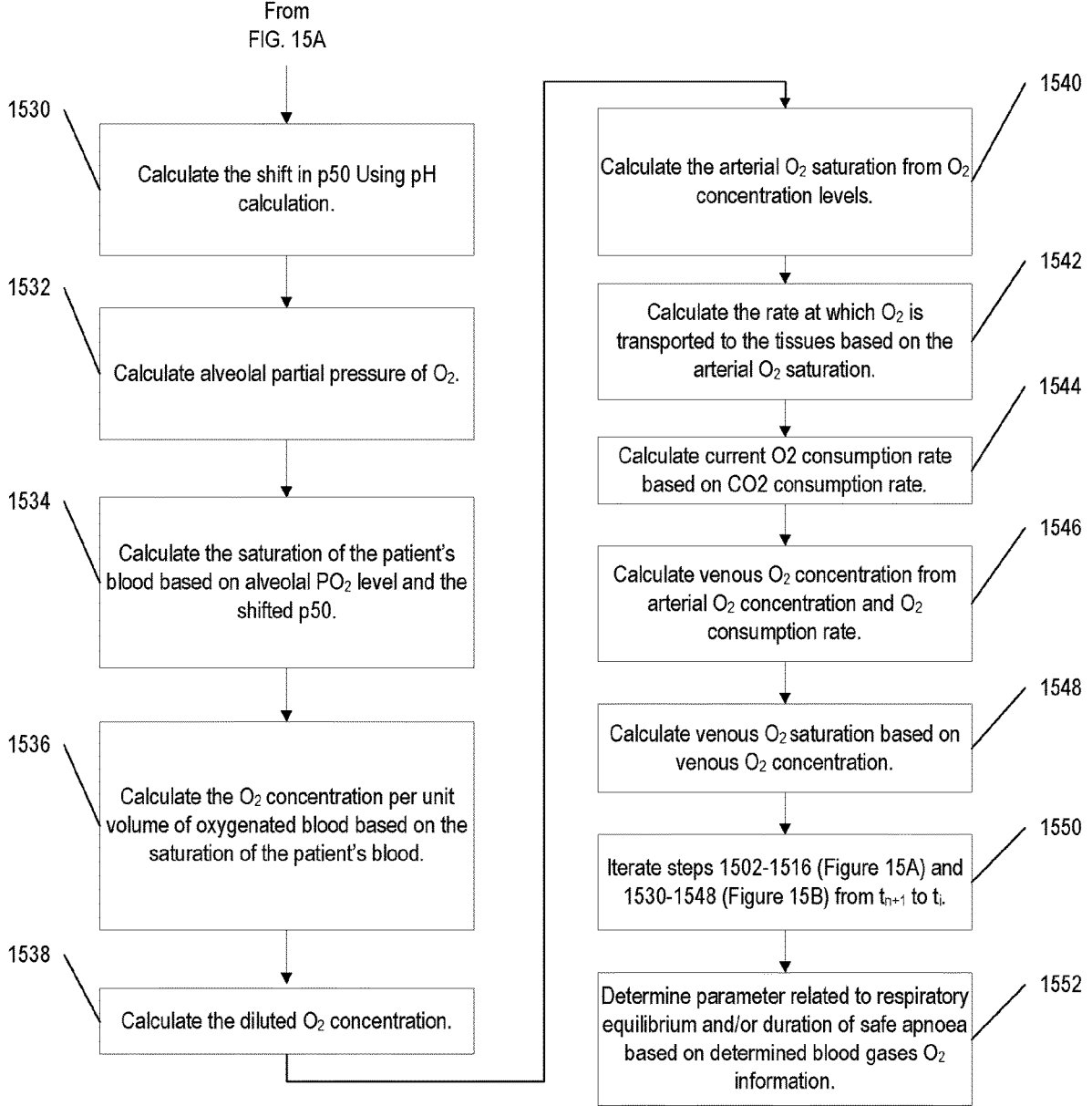

From
FIG. 15A

1530 — Calculate the shift in p50 Using pH calculation.

1532 — Calculate alveolal partial pressure of $O_2$.

1534 — Calculate the saturation of the patient's blood based on alveolal $PO_2$ level and the shifted p50.

1536 — Calculate the $O_2$ concentration per unit volume of oxygenated blood based on the saturation of the patient's blood.

1538 — Calculate the diluted $O_2$ concentration.

1540 — Calculate the arterial $O_2$ saturation from $O_2$ concentration levels.

1542 — Calculate the rate at which $O_2$ is transported to the tissues based on the arterial $O_2$ saturation.

1544 — Calculate current O2 consumption rate based on CO2 consumption rate.

1546 — Calculate venous $O_2$ concentration from arterial $O_2$ concentration and $O_2$ consumption rate.

1548 — Calculate venous $O_2$ saturation based on venous $O_2$ concentration.

1550 — Iterate steps 1502-1516 (Figure 15A) and 1530-1548 (Figure 15B) from $t_{n+1}$ to $t_i$.

1552 — Determine parameter related to respiratory equilibrium and/or duration of safe apnoea based on determined blood gases $O_2$ information.

FIG. 15B

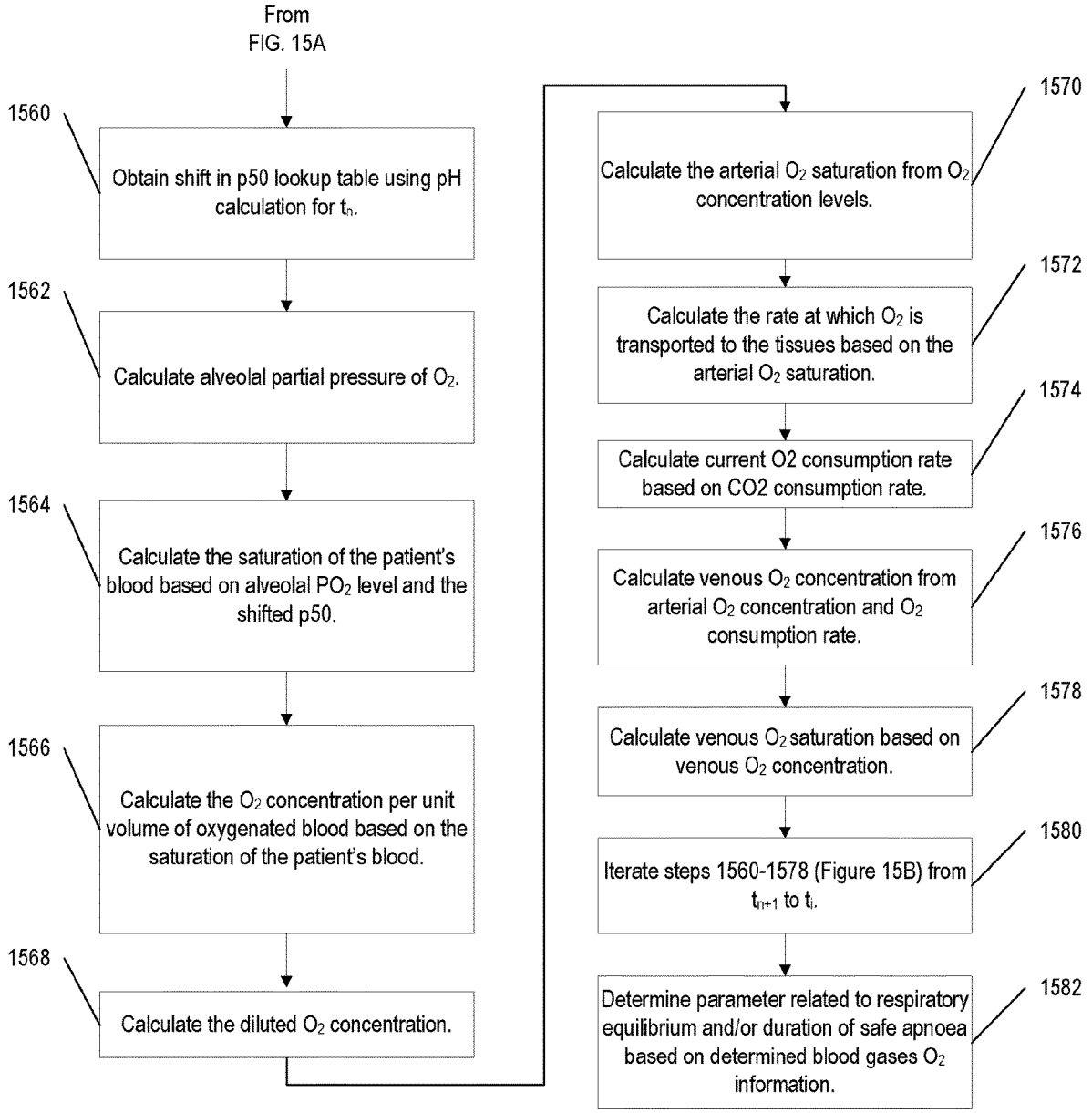

From
FIG. 15A

1560 — Obtain shift in p50 lookup table using pH calculation for $t_n$.

1562 — Calculate alveolal partial pressure of $O_2$.

1564 — Calculate the saturation of the patient's blood based on alveolal $PO_2$ level and the shifted p50.

1566 — Calculate the $O_2$ concentration per unit volume of oxygenated blood based on the saturation of the patient's blood.

1568 — Calculate the diluted $O_2$ concentration.

1570 — Calculate the arterial $O_2$ saturation from $O_2$ concentration levels.

1572 — Calculate the rate at which $O_2$ is transported to the tissues based on the arterial $O_2$ saturation.

1574 — Calculate current O2 consumption rate based on CO2 consumption rate.

1576 — Calculate venous $O_2$ concentration from arterial $O_2$ concentration and $O_2$ consumption rate.

1578 — Calculate venous $O_2$ saturation based on venous $O_2$ concentration.

1580 — Iterate steps 1560-1578 (Figure 15B) from $t_{n+1}$ to $t_i$.

1582 — Determine parameter related to respiratory equilibrium and/or duration of safe apnoea based on determined blood gases $O_2$ information.

FIG. 15C

FLOW THERAPY SYSTEM AND METHOD

TECHNICAL FIELD

The present disclosure generally relates to respiratory gas therapy. More particularly, the present disclosure relates to respiratory gas therapy systems, apparatus, and methods for treating patients receiving anaesthesia or undergoing intubation or endoscopy.

BACKGROUND ART

Intubation is often practiced on patients suffering from various illnesses or injuries. In general, patients who are sedated for a medical procedure require intubation as they often stop spontaneous breathing. In some cases, intubation of a patient can be completed in thirty to sixty seconds, but in other cases, particularly if the patient's airway is difficult to traverse (for example, due to cancer or severe injury), intubation can take much longer.

To prevent hypoxia or hypoxemia during intubation, a medical professional performing the intubation will often pre-oxygenate the patient to be intubated by applying a face mask and delivering oxygen for a period of time until the patient's blood oxygen saturation level (measured using, for example, near infrared spectroscopy or pulse oximetry) reaches approximately 100%. Pre-oxygenation also denitrogenises the patient's lungs, creating an alveolar oxygen reservoir that serves to maintain oxygen saturation levels for a small post-ventilatory window.

Pre-oxygenation can provide a buffer against undesirable declines in oxygen saturation, but for long intubation procedures, it is often necessary to interrupt the intubation process and reapply the face mask to again increase the patient's oxygen saturation level to adequate levels.

The interruption of the intubation process, which can happen several times for a difficult intubation process, can be frustrating to the medical professional. Additionally, the patient can experience rises in blood carbon dioxide due to the poor management of physiological dead space. Similar difficulties can be encountered with patients undergoing, for example, upper endoscopies.

SUMMARY

An apnoea is the temporary absence of breathing. It commonly occurs at the induction of anaesthesia. The duration of safe apnoea is defined as the time until a patient reaches a specified oxygen saturation level. Typically, that oxygen saturation level may be 88-92%, although that level may vary depending on the patient and procedure being carried out. Saturations below this level can rapidly deteriorate to critical levels (e.g., <70%) on the steep section of the oxyhaemoglobin dissociation curve posing significant risk to the patient. Alternatively, the duration of safe apnoea can be defined as the time until a patient reaches a or reaches close to a specified $CO_2$ level, which could be a saturation or threshold level. The duration of safe apnoea can vary considerably patient to patient, and there is a need for methods of assessing the duration of safe apnoea.

According to certain embodiments, aspects and advantages of at least one of the embodiments disclosed herein, a system is disclosed comprising:

at least one input configured to receive information relating to one or more parameters associated with a patient; and at least one processor configured to, based on the information relating to the one or more parameters, determine one or more properties associated with the patient's apnoeic respiratory equilibrium.

In accordance with certain additional features, aspects and advantages of at least one of the embodiments disclosed herein, a method is disclosed of determining one or more properties associated with a respiratory equilibrium of a patient, the method comprising:

receiving information relating to one or more parameters associated with a patient; and based on the information relating to one or more parameters, determining with a processor one or more properties associated with the patient's apnoeic respiratory equilibrium.

According to certain embodiments, aspects and advantages of at least one of the embodiments disclosed herein, a system is disclosed comprising:

one or more inputs configured to receive:

information relating to at least one first parameters associated with one or both of a patient's body mass index (BMI) or body shape index (BSI); and information relating to at least one second physiological parameters associated with the patient; and at least one processor configured to, analyze the information relating to the first and second parameters to determine one or more properties associated with a duration of safe apnoea for the patient.

In accordance with certain additional features, aspects and advantages of at least one of the embodiments disclosed herein, a method is disclosed of determining one or more properties associated with a respiratory equilibrium of a patient, the method comprising:

receiving information relating to at least one first parameter associated with one or both of a patient's body mass index (BMI) and body shape index (BSI);

receiving information relating to at least one second physiological parameter associated with the patient; and analyzing the information relating to the first and second parameters to determine one or more properties associated with a duration of safe apnoea for the patient.

According to certain embodiments, aspects and advantages of at least one of the embodiments disclosed herein, a system is disclosed comprising:

an input configured to obtain at least one parameter capable of being used to determine one or more properties associated with a patient's respiratory equilibrium;

a flow generator adapted to provide pressurized gases to the patient;

at least one hardware controller configured to:

control the flow generator to adjust the flow of pressurized gases to the patient;

receive data corresponding to the at least one parameter as obtained by the input; and determine one or more properties associated with the patient's respiratory equilibrium by analyzing the data.

In accordance with certain additional features, aspects and advantages of at least one of the embodiments disclosed herein, a method of predicting a duration of safe apnoea is disclosed, the method comprising:

measuring an indicator; and determining a duration of safe apnoea from the measured indicator.

In some configurations, the indicator is one or more of a respiratory indicator, and/or a physiological indicator.

In some configurations, the indicator (such as a respiratory indicator and/or a physiological indicator) comprises, or is based on, carbon dioxide concentration, carbon dioxide clearance, respiratory rate, oxygen concentration, arterial oxygen content, arterial carbon dioxide content, venous oxygen content, venous carbon dioxide content, lung volume, lung compliance, lung/airway pressure, airway resistance/patency, V/Q mismatch (ventilation (V)–perfusion (Q)), heart rate, blood pressure, or metabolic rate.

In some configurations, the method comprises measuring a plurality of indicators (such as a respiratory indicator and/or a physiological indicator) of the patient comprising, or based on, two or more of carbon dioxide concentration or clearance, heart rate, respiratory rate, oxygen concentration, blood pressure, arterial oxygen or carbon dioxide content, lung volume, lung compliance, lung/airway pressure, airway resistance/patency, metabolic rate, V/Q mismatch (ventilation (V)–perfusion (Q)) heart rate, blood pressure, or metabolic rate.

In some configurations, the method comprises determining an average duration of safe apnoea from the plurality of measured indicators (such as a respiratory indicator and/or a physiological indicator). In some alternative configurations, the method comprises determining a plurality of durations of safe apnoea from the plurality of measured indicators (such as a respiratory indicator and/or a physiological indicator) and optionally further selecting the shortest duration of safe apnoea from the plurality of durations of safe apnoea In some configurations, the step of determining a duration of safe apnoea comprises comparing or fitting a model to the measured indicator (such as a respiratory indicator and/or a physiological indicator) to determine the duration of safe apnoea.

In some configurations, the method comprises measuring carbon dioxide as an indicator (such as a respiratory indicator and/or a physiological indicator), wherein the carbon dioxide is measured based on expired carbon dioxide, transcutaneous carbon dioxide, or blood gases. In some configurations, the step of determining a duration of safe apnoea comprises comparing the measured carbon dioxide to a maximum carbon dioxide limit. In some configurations, the maximum carbon dioxide limit is determined from a look up table with different carbon dioxide limits. In some configurations, the look up table comprises different carbon dioxide limits depending on one or more of disease, age, height, weight, pregnancy status, difficult airway type. In some alternative configurations, the maximum carbon dioxide limit is predetermined by a breath hold test to establish the maximum carbon dioxide level before the patient needs to breathe again.

In some configurations, the method comprises measuring oxygen concentration as an indicator (such as a respiratory indicator and/or a physiological indicator). In some configurations, the oxygen concentration is measured based on expired oxygen, transcutaneous oxygen, blood gases, haemoglobin oxygen concentration, blood pressure, arterial partial pressure of oxygen, arterial oxygen content, venous oxygen content or venous carbon dioxide content.

In some configurations, the duration of safe apnoea is determined based on a threshold arterial (PaO2) and/or venous (PvO2) partial pressure of oxygen.

In some configurations, the threshold arterial oxygen content is determined from a threshold haemoglobin oxygen saturation (SpO2).

In some configurations, a user may input the specified threshold (arterial and/or venous) haemoglobin oxygen saturation ($SpO_2$, $SvO_2$), threshold arterial partial pressure of oxygen ($PaO_2$) and/or threshold venous partial pressure of oxygen ($PVO_2$).

In some configurations, the threshold (arterial and/or venous) haemoglobin oxygen saturation ($SpO_2$, $SvO_2$), threshold arterial partial pressure of oxygen (PaO2) and/or threshold venous partial pressure of oxygen ($PVO_2$) may be a predetermined value.

In some configurations, the duration of safe apnoea is based on, or for example may be equal to, a length of time until the arterial partial pressure of oxygen reaches the threshold arterial partial pressure of oxygen In some configurations, the length of time until the arterial partial pressure of oxygen reaches the threshold arterial partial pressure of oxygen is determined by measuring or estimating a rate of change of arterial partial pressure of oxygen.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea from a measured indicator.

In some configurations, the indicator is one or more of a respiratory indicator, and/or a physiological indicator.

In some configurations, the processor is a remote processor.

In some configurations, the respiratory indicator (such as a respiratory indicator and/or a physiological indicator) comprises, or is based on, carbon dioxide concentration, carbon dioxide clearance, respiratory rate, oxygen concentration, arterial or venous oxygen, arterial or venous carbon dioxide content, lung volume, lung compliance, lung/airway pressure, airway resistance/patency, V/Q mismatch (ventilation (V)–perfusion (Q)), heart rate, blood pressure, or metabolic rate.

In some configurations, the processor is configured to determine the duration of safe apnoea from a plurality of indicators (such as a respiratory indicator and/or a physiological indicator) comprising, or based on, two or more of carbon dioxide concentration, carbon dioxide clearance, respiratory rate, oxygen concentration, arterial or venous oxygen, arterial or venous carbon dioxide content, lung volume, lung compliance, lung/airway pressure, airway resistance/patency, V/Q mismatch (ventilation (V)–perfusion (Q)), heart rate, blood pressure, or metabolic rate.

In some configurations, the processor is configured to determine an average duration of safe apnoea from the plurality of measured indicators (such as a respiratory indicator and/or a physiological indicator). In some alternative configurations, the processor is configured to determine a plurality of durations of safe apnoea from the plurality of measured indicators (such as a respiratory indicator and/or a physiological indicator) and further optionally wherein the processor selects the shortest duration of safe apnoea from the plurality of durations of safe apnoea.

In some configurations, the processor is configured to compare or fit a model to the measured indicator (such as a respiratory indicator and/or a physiological indicator) determine the duration of safe apnoea.

In some configurations, the or an indicator (such as a respiratory indicator and/or a physiological indicator) comprises measured carbon dioxide, and the processor is configured to compare the measured carbon dioxide to a maximum carbon dioxide limit to determine the duration of safe apnoea. In some configurations, the processor is configured to determine the maximum carbon dioxide limit from a look up table with different carbon dioxide limits. In some configurations, the look up table comprises different carbon dioxide limits depending on one or more or a combination of disease, age, height, weight, pregnancy status, difficult airway type. In some configurations, the processor is configured to compare the measured carbon dioxide to a predetermined maximum carbon dioxide limit to predict the duration of safe apnoea.

In some configurations, the system is configured to measure oxygen concentration as an indicator.

In some configurations, the oxygen concentration is measured based on expired oxygen, transcutaneous oxygen, blood gases, haemoglobin oxygen concentration, blood pressure, arterial or venous partial pressure of oxygen, or arterial or venous oxygen content.

In some configurations, the processor is configured to determine the duration of safe apnoea based on a threshold arterial or venous partial pressure of oxygen (PaO2).

In some configurations, the threshold arterial or venous oxygen content is determined from a threshold haemoglobin oxygen saturation (SpO2).

In some configurations, the system may comprise comprising a user interface to enable a user to input the threshold haemoglobin oxygen arterial saturation (SpO$_2$) or venous saturation (SvO$_2$), or threshold arterial partial pressure of oxygen (PaO$_2$) or venous partial pressure of oxygen (PvO2).

In some configurations, the threshold haemoglobin oxygen arterial saturation (SpO$_2$) or venous saturation (SvO$_2$), or threshold arterial partial pressure of oxygen (PaO2) or venous partial pressure of oxygen (PvO2) may be a predetermined value.

In some configurations, the processor is configured to determine the duration of safe apnoea based on, a length of time until the arterial or venous partial pressure of oxygen reaches the threshold arterial or venous partial pressure of oxygen In some configurations, the length of time until the arterial or venous partial pressure of oxygen reaches the threshold arterial or venous partial pressure of oxygen is determined by the processor by measuring or estimating a rate of change of arterial or venous partial pressure of oxygen.

Additionally, in accordance with certain features, aspects and advantages of at least one of the embodiments disclosed herein, a method of determining a duration of safe apnoea is disclosed, the method comprising:

determining a duration of safe apnoea based on a relationship between haemoglobin arterial oxygen saturation (SpO2) or venous saturation (SvO$_2$) and arterial partial pressure of oxygen (PaO2) or venous partial pressure of oxygen (PvO2).

In some configurations, the method comprises measuring SpO2, SvO$_2$, PvO2, and PaO2 at set times. In some configurations, the measuring of SpO2 comprises using pulse oximetry.

In some configurations, the measuring of PaO2 or PvO2 comprises measuring blood gases or inferring the PaO2 or PvO2 from a transcutaneous oxygen measurement.

In some configurations, the method comprises determining a PaO2 or PvO2 value that relates to a specified minimum safe value of SpO2 or SvO$_2$. In some configurations, the specified minimum safe value of SpO2 or SvO$_2$ is a predetermined value or is a user input value. In some configurations, the minimum safe value of SpO2 is about 90%.

In some configurations, the method comprises determining the time remaining until the determined PaO2 or PvO2 value is reached, based on a relationship between measured PaO2 or PvO2 values and time.

In some configurations, the method comprises determining the time remaining until the determined PaO2 or PvO2 value is reached, based on a rate of change of PaO2 or PvO2.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on a relationship between haemoglobin arterial oxygen saturation (SpO2) or venous oxygen saturation (SpO2) and arterial partial pressure of oxygen (PaO2) or venous partial pressure of oxygen (PvO2).

In some configurations, the processor is a remote processor.

In some configurations, the system is configured to predict the duration of safe apnoea based on a relationship between measured values of SpO2 and PaO2 (or SvO2 and PvO2) at set times. In some configurations, the processor is configured to determine a PaO2 value that relates to a specified minimum safe value of SpO2 (or a PvO2 value that relates to a specified minimum safe value of SvO2). In some configurations, the specified minimum safe value of SpO2 (or SvO2) is a predetermined value. In some alternative configurations, the system comprises a user interface to enable a user to input the specified minimum safe value of SpO2 (or SvO2).

In some configurations, the processor is configured to determine the time remaining until the determined PaO2 (or PvO2) value is reached, based on a relationship between measured PaO2 (or PvO2) values and time.

In some configurations, the method comprises determining the time remaining until the determined PaO2 (or PvO2) value is reached, based on a rate of change of PaO2 (or PvO2).

Additionally, in accordance with certain features, aspects and advantages of at least one of the embodiments disclosed herein, a respiratory therapy system is disclosed, the system comprising a method of determining a duration of safe apnoea, the method comprising:

determining a duration of safe apnoea based on a relationship between a patient's oxygen reservoir and the patient's oxygen consumption.

In some configurations, the method comprises determining the functional residual capacity of a patient's lungs to estimate a maximum oxygen reservoir volume. In some configurations, the step of determining the functional residual capacity comprises estimating the functional residual capacity using one or more of nitrogen washout, helium dilution, body plethysmography, using a look up table.

In some configurations, the method comprises measuring or predicting a fraction of expired oxygen in the patient's lungs. In some configurations, the method comprises determining the patient's oxygen reservoir based on the maximum oxygen reservoir volume less the amount or volume or fraction of expired oxygen, plus an amount or volume of oxygen provided to the patient by the respiratory therapy system, if any. In some configurations, the method comprises determining the patient's oxygen consumption by estimating the patient's oxygen consumption based on weight, or metabolic rate, or measuring or estimating the patient's oxygen consumption, or measuring or estimating a $CO_2$ volume or concentration at or near a patient's airway.

In some configurations, the method comprises determining the duration of safe apnoea based on the patient's determined oxygen reservoir divided by the patient's oxygen consumption.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on a relationship between a patient's oxygen reservoir and the patient's oxygen consumption.

In some configurations, the processor is a remote processor.

In some configurations, the processor is configured to determine the patient's oxygen reservoir based on a maximum oxygen reservoir volume, less an amount or volume or fraction of expired oxygen, plus an amount or volume of oxygen provided by the respiratory therapy system, if any. In some configurations, the processor is configured to determine the duration of safe apnoea based on the patient's determined oxygen reservoir divided by the patient's oxygen consumption.

In some configurations, the system may be configured to determine the patient's oxygen consumption by estimating the patient's oxygen consumption based on weight, or metabolic rate, or measuring or estimating the patient's oxygen consumption, or measuring or estimating a $CO_2$ volume or concentration at or near a patient's airway.

Additionally, in accordance with certain features, aspects and advantages of at least one of the embodiments disclosed herein, a method of determining a duration of safe apnoea is disclosed, the method comprising:

determining a duration of safe apnoea based on one or more parameters relating to pre-oxygenation of a patient.

In some configurations, the parameter(s) is/are indicative of the effort to pre-oxygenate the patient.

In some configurations, the parameters comprise one or more of: a relationship of fraction of oxygen in expired air and fraction of inspired oxygen, a relationship of haemoglobin oxygen saturation and fraction of inspired oxygen, a relationship of arterial partial pressure of oxygen and fraction of inspired oxygen, the time to pre-oxygenate, the patient's metabolic rate.

In some configurations, the method comprises using one or more mathematical formulae or relationships to determine the duration of safe apnoea based on the one or more parameters.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on one or more parameters relating to pre-oxygenation of a patient.

In some configurations, the processor is a remote processor.

In some configurations, the parameter(s) is/are indicative of the effort to pre-oxygenate the patient.

In some configurations, the processor is configured to determine the duration of safe apnoea based on one or more of: a relationship of fraction of oxygen in expired air and fraction of inspired oxygen, a relationship of haemoglobin oxygen saturation and fraction of inspired oxygen, a relationship of arterial partial pressure of oxygen and fraction of inspired oxygen, the time to pre-oxygenate, the patient's metabolic rate.

In some configurations, the processor is configured to determine the duration of safe apnoea based on the one or more parameters using one or more mathematical formulae or relationships.

Additionally, in accordance with certain features, aspects and advantages of at least one of the embodiments disclosed herein, a method of determining a duration of safe apnoea is disclosed, the method comprising:

obtaining information relating to an indicator; and determining a duration of safe apnoea from the obtained information.

In some configurations, the indicator is one or more of a respiratory indicator, and/or a physiological indicator.

In some configurations, the method may have any one or more of the features disclosed herein.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on obtained information relating to an indicator.

In some configurations, the indicator is one or more of a respiratory indicator, and/or a physiological indicator.

In some configurations, the system may have any one or more of the features disclosed herein.

In some configurations, the processor is a remote processor.

Features from one or more embodiments may be combined with features of one or more other embodiments. Additionally, more than one embodiment may be used together during a process of respiratory support of a patient.

As relatively high gas delivery flow rates may be used with the embodiments or configurations described herein, the gases being supplied or delivered to the user or patient can may be delivered to different parts of the user's or a patient's airway.

For example, according to those various embodiments and configurations described herein, a flowrate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min (LPM), or more, and useful ranges may be selected between any of these values (for example, between about 40 LPM to about 80 LPM, or between about 50 LPM to about 80 LPM, or between about 60 LPM to about 80 LPM, or between about 70 LPM to about 80 LPM, or between about SLPM and about 150 LPM, or between 10 LPM and about 150 LPM, or between about 15 LPM and about 150 LPM, or between about 20 LPM and about 150 LPM, or between about 20 LPM and about 120 LPM, or between about 30 LPM and about 120 LPM, or between about 20 LPM and about 100 LPM, or between about 20 LPM and about 90 LPM, or between about 25 LPM and about 85 LPM, or between about 30 LPM and about 80 LPM or between about 30 LPM and about 90 LPM, or between about 35 LPM and about 75 LPM, or between about 40 LPM and about 70 LPM, or between about 45 LPM and about 65 LPM, or between about 50 LPM and about 60 LPM).

Such relatively high flowrates of gases may assist in providing the supplied gases into a user's airway, or to different parts of a user's airway, for example such flowrates may allow for a delivery of such gases to the upper or lower airway regions. Upper airway region typically includes the nasal cavity, pharynx and larynx, while the lower airway region typically includes the trachea, primary bronchi and lungs.

Additionally, in accordance with certain features, aspects and advantages of at least one of the embodiments disclosed herein, a system is disclosed, comprising:

at least one input configured to receive information relating to one or more parameters associated with a patient; and at least one processor configured to, based on the information relating to the one or more parameters, determine one or more properties associated with the patient's apnoeic respiratory equilibrium.

In some configurations, one or more properties associated with the patient's apnoeic respiratory equilibrium comprise one or more of time to reach equilibrium, duration of equilibrium, equilibrium value, and rate of decline till equilibrium.

In some configurations, the processor is further configured to, based on the determined properties associated with the patient's apnoeic respiratory equilibrium, determine a duration of safe apnoea.

In some configurations, the one or more properties comprise properties associated with oxygen saturation. In some configurations, the one or more properties comprise properties associated with carbon dioxide saturation.

In some configurations, the input is configured to receive data from one or more respiratory and/or physiological sensors. In some configurations, the one or more physiological sensors comprise a pulse oximeter. The processor in some implementations is configured to, based on the data from the one or more physiological sensors, perform one or more updates to one or more of the determination of the one or more properties associated with the patient's apnoeic respiratory equilibrium, a determination of one or more properties associated with the patient's duration of safe apnoea, and a determination of one or more properties associated with the patient's airway patency.

In some configurations, the processor is configured to perform the one or more updates based on measured information relating to PaO2.

In some configurations, the input comprises a user interface. In some configurations, the input is further configured to receive one or more safety parameters. In some configurations, the one or more safety parameters comprise a threshold desaturation level.

In some configurations, the one or more safety parameters comprise a threshold respiratory equilibrium duration.

In some configurations, the system further comprises a lung volume measurement device configured to estimate lung volume.

In some configurations, the one or more parameters associated with the patient comprise one or more of height, weight, neck circumference, waist circumference, and hip to waist ratio.

In some configurations, the one or more parameters associated with the patient comprise (body mass index) BMI or BMI distribution. In some configurations, the one or more parameters associated with the patient comprise (body shape index) BSI. In some configurations, the one or more parameters associated with the patient comprise a body morphology indication. In some configurations, the one or more parameters comprise lung volume. In some configurations, the one or more parameters comprise cardiac output. In some configurations, the one or more parameters comprise one or more of age, pregnancy status, difficult airway type, medical history, disease characteristics, treatment history, and gas flow characteristics.

In some configurations, the processor is configured to determine a V/Q (ventilation/perfusion) mismatch for the patient using the information relating to the one or more parameters associated with the patient and, based on the V/Q mismatch, determine the one or more properties associated with the patient's apnoeic respiratory equilibrium. In some configurations, the processor is configured to determine the V/Q mismatch for the patient based on the patient's BMI. In some configurations, the processor is configured to determine the V/Q mismatch for the patient based on a correlation of the patient's BMI with one or more of neck circumference, BSI, hip-to-waist ratio, monitored PaO2, and blood gas concentration.

In some configurations, the processor is configured to compare or fit a model to the information relating to the one or more parameters associated with the patient to determine the one or more properties associated with the patient's apnoeic respiratory equilibrium.

In some configurations, the processor is configured to, based on information relating to at least one first parameter of the one or more parameters associated with the patient, determine the one or more properties associated with the patient's apnoeic respiratory equilibrium, and based on information relating to at least one second parameter of the one or more parameters associated with the patient, determine a duration of safe apnoea of the patient.

In some configurations, the first parameter comprises one or more of BMI, PaO2, blood gas concentration, and cardiac output, and the second parameter comprises one or more of PaO2 and blood gas concentration.

In some configurations, the processor determines the one or more properties associated with the patient's apnoeic respiratory equilibrium based on a ratio of PaO2 and BMI.

In some configurations, the processor determines the one or more properties associated with the patient's apnoeic respiratory equilibrium based on a ratio of blood gas concentration and BMI. In some configurations, the processor determines the one or more properties associated with the patient's apnoeic respiratory equilibrium based on a ratio of cardiac output and BMI. In some configurations, the processor is configured to determine that the patient is atypical based on the information relating to the one or more parameters associated with the patient.

In some configurations, the processor is configured to determine a ratio of measured PaO2, blood gas concentration, or cardiac output to BMI, and to compare or fit the ratio to determine the one or more properties associated with the patient's respiratory equilibrium.

In some configurations, the processor is configured to determine that the patient is atypical based on the information relating to the one or more parameters, and to determine the one or more properties associated with the patient's apnoeic respiratory equilibrium based on the determined atypicality.

In some configurations, the determined atypicality is that the patient has a BMI beyond a threshold amount.

In some configurations, comprising an output configured to provide information to a user. In some configurations, the output is configured to output an alarm. In some configurations, the output comprises a display configured to display information relating to the one or more properties associated with the patient's apnoeic respiratory equilibrium, relating to a duration of safe apnoea, or both.

In some configurations, the system further comprises a flow generator adapted to provide a flow of gases to the patient. In some configurations, the processor is configured to cause the flow generator to control a flow of the gases to the patient based on the one or more properties associated with the patient's apnoeic respiratory equilibrium.

In some configurations, the system further comprises a sealing or non-sealing patient interface adapted to attach to the patient and configured to deliver the gases to the patient.

In some configurations, the system comprises a high flow respiratory therapy system. In some configurations, the system comprises a varying flow respiratory therapy system.

According to certain features, also disclosed are methods of using any of the above described systems.

Additionally, in accordance with certain features, aspects and advantages of at least one of the embodiments disclosed herein, a method is disclosed of determining one or more properties associated with a respiratory equilibrium of a patient, the method comprising:

receiving information relating to one or more parameters associated with a patient; and based on the information relating to one or more parameters, determining with a processor one or more properties associated with the patient's apnoeic respiratory equilibrium.

In some configurations, the one or more properties associated with the patient's apnoeic respiratory equilibrium comprises one or more of time to reach equilibrium, duration of equilibrium, equilibrium value, and rate of decline till equilibrium.

In some configurations, the method further comprises determining with the processor a duration of safe apnoea based on the determined properties associated with the patient's apnoeic respiratory equilibrium.

In some configurations, the one or more properties comprise properties associated with oxygen saturation. In some configurations, the one or more properties comprise properties associated with carbon dioxide saturation.

In some configurations, the method further comprises receiving data from one or more respiratory and/or physiological sensors.

In some configurations, the one or more physiological sensors comprise a pulse oximeter.

In some configurations, the method further comprises performing, based on the data from the one or more physiological sensors, one or more updates to one or more of the determination of the one or more properties associated with one or more of the patient's apnoeic respiratory equilibrium, a determination of one or more properties associated with the patient's duration of safe apnoea, and a determination of one or more properties associated with the patient's airway patency.

In some configurations, the performing is based on measured information relating to PaO2.

In some configurations, the receiving comprises receiving the information relating to the one or more parameters via a user interface.

In some configurations, the method further comprises receiving one or more safety parameters. In some configurations, the one or more safety parameters comprise a threshold desaturation level. In some configurations, the one or more safety parameters comprise a threshold respiratory equilibrium duration.

In some configurations, the method further comprises receiving an estimate of the patient's lung volume measured using a lung volume measurement device.

In some configurations, the one or more parameters associated with the patient comprise one or more of height, weight, neck circumference, waist circumference, and hip to waist ratio.

In some configurations, the one or more parameters associated with the patient comprise (body mass index) BMI or BMI distribution. In some configurations, the one or more parameters associated with the patient comprise (body shape index) BSI. In some configurations, the one or more parameters associated with the patient comprise a body morphology indication. In some configurations, the one or more parameters comprise lung volume. In some configurations, the one or more parameters comprise cardiac output. In some configurations, the one or more parameters comprise one or more of age, pregnancy status, difficult airway type, medical history, disease characteristics, treatment history, and gas flow characteristics.

In some configurations, the method further comprises, with the processor:

determining a V/Q (ventilation/perfusion) mismatch for the patient using the information relating to the one or more parameters associated with the patient; and based on the V/Q mismatch, determining the one or more properties associated with the patient's apnoeic respiratory equilibrium.

In some configurations, the method further comprises determining the V/Q mismatch is based on the patient's BMI. In some configurations, the determining the V/Q mismatch is based on a correlation of the patient's BMI with one or more of neck circumference, BSI, hip-to-waist ratio, monitored PaO2, and blood gas concentration.

In some configurations, the determining the one or more properties associated with the patient's apnoeic respiratory equilibrium comprises comprising comparing or fitting a model to the information relating to the one or more parameters associated with the patient.

In some configurations, the determining the one or more properties associated with the patient's apnoeic respiratory equilibrium is based on information relating to at least one first parameter of the one or more parameters associated with the patient, and wherein the method further comprises, based on information relating to at least one second parameter of the one or more parameters associated with the patient, determining a duration of safe apnoea of the patient.

In some configurations, the first parameter comprises one or more of BMI, PaO2, blood gas concentration, and cardiac output, and the second parameter comprises one or more of PaO2 and blood gas concentration.

In some configurations, the determining the one or more properties associated with the patient's apnoeic respiratory equilibrium is based on a ratio of PaO2 and BMI. In some configurations, the determining the one or more properties associated with the patient's apnoeic respiratory equilibrium is based on a ratio of blood gas concentration and BMI. In some configurations, wherein the determining the one or more properties associated with the patient's apnoeic respiratory equilibrium is based on a ratio of cardiac output and BMI. In some configurations, the method further comprises determining that the patient is atypical based on the information relating to the one or more parameters associated with the patient.

In some configurations, the method further comprises:

determining a ratio of measured PaO2, blood gas concentration, or cardiac output to BMI; and comparing or fitting the ratio to determine the one or more properties associated with the patient's respiratory equilibrium.

In some configurations, the method further comprises:

determining that the patient is atypical based on the information relating to the one or more parameters; and determining the one or more properties associated with the patient's apnoeic respiratory equilibrium based on the determined atypicality.

In some configurations, the determined atypicality is that the patient has a BMI beyond a threshold amount.

In some configurations, the method further comprises outputting information to a user relating to the one or more properties associated with the patient's apnoeic respiratory equilibrium. In some configurations, the outputting comprises outputting an alarm. In some configurations, the outputting comprises displaying on a display information relating to the one or more properties associated with the patient's apnoeic respiratory equilibrium, information relating to a duration of safe apnoea, or both.

In some configurations, the method further comprising providing a flow of gases to the patient. In some configurations, the method further comprises controlling the flow of the gases to the patient based on the one or more properties associated with the patient's apnoeic respiratory equilibrium. In some configurations, providing comprises using a sealing or non-sealing patient interface to deliver the gases to the patient. In some configurations, wherein the providing is performed using a high flow respiratory therapy system. In some configurations, the providing is performed using a varying flow respiratory therapy system.

According to certain features, also disclosed are systems configured to implement any of the above methods.

Additionally, in accordance with certain features, aspects and advantages of at least one of the embodiments disclosed herein, a system comprises:

one or more inputs configured to receive:

information relating to at least one first parameters associated with one or both of a patient's body mass index (BMI) or body shape index (BSI); and information relating to at least one second physiological parameters associated with the patient; and at least one processor configured to, analyze the information relating to the first and second parameters to determine one or more properties associated with a duration of safe apnoea for the patient.

In some configurations, the second parameter comprises lung volume. In some configurations, the second parameter comprises cardiac output. In some configurations, the second parameter comprises oxygen saturation. In some configurations, the second parameter comprises carbon dioxide saturation. In some configurations, the second parameter comprises blood gas concentration. In some configurations, the second parameter comprises one or more of age, height, pregnancy status, difficult airway type, medical history, disease characteristics, treatment history, and gas flow characteristics. In some configurations, the second parameter comprises one or more of neck circumference, body shape index (BSI), and hip-to-waist ratio. In some configurations, the second parameter comprises $PaO_2$.

In some configurations, the first parameter comprises height and weight, and the processor is configured to calculate a BMI value for the patient from the height and weight.

In some configurations, the processor determines the one or more properties associated with the duration of safe apnoea for the patient based on a ratio of BMI and information relating to another parameter. In some configurations, the processor determines the one or more properties associated with the duration of safe apnoea for the patient based on a ratio of $PaO_2$ and BMI. In some configurations, the processor determines the one or more properties associated with the duration of safe apnoea for the patient based on a ratio of blood gas concentration and BMI. In some configurations, the processor determines the one or more properties associated with the duration of safe apnoea for the patient based on a ratio of cardiac output and BMI. In some configurations, the processor is configured to determine a ratio of BMI and one or more of measured $PaO_2$, blood gas concentration, or cardiac output, and to compare or fit the ratio to a model determine the one or more properties associated with the duration of safe apnoea for the patient.

In some configurations, the processor is configured to determine one or more properties associated with an apnoeic respiratory equilibrium based on the information relating to the one or more of the first and second parameters.

In some configurations, the processor is configured to use the one or more properties associated with the apnoeic respiratory equilibrium to determine the one or more properties associated with the duration of safe apnoea.

In some configurations, the one or more properties associated with the patient's apnoeic respiratory equilibrium comprise one or more of time to reach equilibrium, equilibrium value, rate of decline until equilibrium, and airway patency.

In some configurations, the apnoeic respiratory equilibrium is an oxygen saturation level. In some configurations, the apnoeic respiratory equilibrium is a carbon dioxide saturation level.

In some configurations, the processor is configured to compare or fit a model to the information relating to the first parameter, the information relating to the second parameter, or both, to determine the one or more properties associated with the duration of safe apnoea.

In some configurations, the one or more inputs are configured to receive data from one or more physiological sensors. In some configurations, the one or more physiological sensors comprise a pulse oximeter. In some configurations, the processor is configured to, based on the data from the one or more physiological sensors, perform one or more updates to the determination of the one or more properties associated with the patient's duration of safe apnoea.

In some configurations, the processor is configured to perform the one or more updates based on measured information relating to $PaO_2$.

In some configurations, the one or more inputs comprises a user interface. In some configurations, the one or more inputs are further configured to receive one or more safety parameters. In some configurations, the one or more safety parameters comprise a threshold desaturation level. In some configurations, the one or more safety parameters comprise a threshold respiratory equilibrium duration.

In some configurations, the system further comprises a lung volume measurement device configured to estimate lung volume.

In some configurations, the system further comprises a flow generator adapted to provide a flow of gases to the patient.

In some configurations, the processor is configured to cause the flow generator to control a flow of the gases to the patient based on the one or more properties associated with the duration of safe apnoea.

In some configurations, the system further comprises comprising a sealing or non-sealing patient interface adapted to attach to the patient and configured to deliver the gases to the patient.

In some configurations, the system comprises a high flow respiratory therapy system. In some configurations, the system comprises a varying flow respiratory therapy system.

In some configurations, the at least one processor is configured to determine airway patency based on the information relating to the at least one second parameter.

According to certain features, also disclosed are methods of using any of the above systems.

Additionally, in accordance with certain features, aspects and advantages of at least one of the embodiments disclosed herein, a method of determining one or more properties associated with a respiratory equilibrium of a patient comprises:

receiving information relating to at least one first parameter associated with one or both of a patient's body mass index (BMI) and body shape index (BSI);

receiving information relating to at least one second physiological parameter associated with the patient; and analyzing the information relating to the first and second parameters to determine one or more properties associated with a duration of safe apnoea for the patient.

In some configurations, the second parameter comprises lung volume. In some configurations, the second parameter comprises cardiac output. In some configurations, the second parameter comprises oxygen saturation. In some configurations, the second parameter comprises carbon dioxide saturation. In some configurations, the second parameter comprises blood gas concentration. In some configurations, the second parameter comprises one or more of age, height, pregnancy status, difficult airway type, medical history, disease characteristics, treatment history, and gas flow characteristics. In some configurations, the second parameter comprises one or more of neck circumference, body shape index (BSI), and hip-to-waist ratio. In some configurations, the second parameter comprises PaO2.

In some configurations, the first parameter comprises height and weight, and the method further comprises calculating with the processor a BMI value for the patient from the height and weight.

In some configurations, the determining the one or more properties associated with the duration of safe apnoea for the patient is based on a ratio of BMI and information relating to another parameter. In some configurations, the determining the one or more properties associated with the duration of safe apnoea for the patient is based on a ratio of PaO2 and BMI. In some configurations, the determining the one or more properties associated with the duration of safe apnoea for the patient is based on a ratio of blood gas concentration and BMI. In some configurations, determining the one or more properties associated with the duration of safe apnoea for the patient is based on a ratio of cardiac output and BMI.

In some configurations, the method further comprises, with the processor:

determining a ratio of BMI and one or more of measured PaO2, blood gas concentration, or cardiac output; and comparing or fitting the ratio to a model determine the one or more properties associated with the duration of safe apnoea for the patient.

In some configurations, the determining the one or more properties associated with an apnoeic respiratory equilibrium is based on the information relating to the one or more of the first and second parameters.

In some configurations, the method further comprises, with the processor, using the one or more properties associated with the apnoeic respiratory equilibrium to determine the one or more properties associated with the duration of safe apnoea.

In some configurations, the one or more properties associated with the patient's apnoeic respiratory equilibrium comprise one or more of time to reach equilibrium, equilibrium value, rate of decline until equilibrium, and airway patency.

In some configurations, the apnoeic respiratory equilibrium is an oxygen saturation level.

In some configurations, the apnoeic respiratory equilibrium is a carbon dioxide saturation level.

In some configurations, the determining the one or more properties associated with the duration of safe apnoea comprises comparing or fitting a model to the information relating to the first parameter, the information relating to the second parameter, or both.

In some configurations, the one or more of the receiving the information relating to the at least one first parameter and the receiving the information relating to the at least one second parameter comprises using one or more physiological sensors. In some configurations, the one or more physiological sensors comprise a pulse oximeter.

In some configurations, the method further comprises, with the processor and based on the data from the one or more physiological sensors, performing one or more updates to the determination of the one or more properties associated with the patient's duration of safe apnoea.

In some configurations, the performing the one or more updates is based on measured information relating to PaO2.

In some configurations, the one or more of the receiving the information relating to the at least one first parameter and the receiving the information relating to the at least one second parameter is via a user interface.

In some configurations, the method further comprises receiving one or more safety parameters. In some configurations, the one or more safety parameters comprise a threshold desaturation level. In some configurations, the one or more safety parameters comprise a threshold respiratory equilibrium duration.

In some configurations, the method comprises estimating lung volume of the patient using a lung volume measurement device.

In some configurations, the method further comprises providing a flow of gases to the patient. In some configurations, the providing the flow of gases is based on the one or more properties associated with the duration of safe apnoea.

In some configurations, the method comprising using a sealing or non-sealing patient interface to deliver the gases to the patient.

In some configurations, the providing is performed using a high flow respiratory therapy system.

In some configurations, the providing is performed using a varying flow respiratory therapy system.

In some configurations, the method further comprises determining airway patency based on the information relating to the at least one second parameter.

According to certain features, also disclosed are systems for performing any of the above methods.

Additionally, in accordance with certain features, aspects and advantages of at least one of the embodiments disclosed herein, a system comprises:

an input configured to obtain at least one parameter capable of being used to determine one or more properties associated with a patient's respiratory equilibrium;

a flow generator adapted to provide pressurized gases to the patient;

at least one hardware controller configured to:

control the flow generator to adjust the flow of pressurized gases to the patient;

receive data corresponding to the at least one parameter as obtained by the input; and determine one or more properties associated with the patient's respiratory equilibrium by analyzing the data.

In some configurations, the controller is configured to control the flow generator to adjust the flow of pressurized gases to the patient in response to the analysis of the data.

Additionally, in accordance with certain features, aspects and advantages of at least one of the embodiments disclosed herein, a method of determining a patient blood gases carbon dioxide (CO2) level, the method comprising:

obtaining an nth CO2 parameter value (Pn) relating to the patient blood gases CO2 level at an nth time (tn);

determining an intermediate CO2 parameter value (Vn);

determining an (n+1)th CO2 parameter value (Pn+1) at an (n+1)th time (tn+1) based on the intermediate CO2 parameter value (Vn); and iterating said obtaining an nth CO2 parameter value (Pn), said determining an intermediate CO2 parameter value (Vn), and said determining an (n+1)th CO2 parameter value (Pn+1), to obtain a prediction of a progression of the patient blood gases CO2 level from a time t1 to a time ti.

In some configurations, the method is carried out entirely before a medical procedure.

In some configurations, the method is carried out at least partly during a medical procedure, and wherein one or more of the CO2 parameter values (P1-Pi) or one or more of the intermediate CO2 parameter values (V1-Vi) are determined using real time measurements.

In some configurations, one or more of the CO2 parameter values (P1-Pi) comprise values obtained from a population dataset, measured, estimated, or calculated.

In some configurations, a first parameter input (P1) comprises an estimated value.

In some configurations, Vn comprises a volume of CO2 that will be stored in the patient at tn+1.

In some configurations, the determining an intermediate CO2 parameter value (Vn) comprises determining the intermediate CO2 parameter value (Vn) based on a function of a CO2 production parameter (In) and a CO2 clearance parameter (3n). In some configurations, the first CO2 production parameter (I1) is based on one or more of:

a metabolic rate or oxygen (O2) consumption rate of the patient; and a respiratory exchange ratio of the patient.

In sone configuration one or more subsequent CO2 production parameter (In) is based on one or more of:

a metabolic rate of the patient or O2 consumption rate of the patient);

a respiratory exchange ratio of the patient;

temperature of the patient;

volume of the patient' blood, body fluids, or lungs;

a blood PCO2 or blood pH of the patient, or an associated parameter thereof; and haemoglobin concentration in the patient's blood.

In some configurations, the CO2 production parameter (In) comprises one or more real-time measurements.

In some configurations, the CO2 clearance parameter (Jn) comprises one or more values obtained from a population dataset, measured, estimated, or calculated. In some configurations, the CO2 clearance parameter (Jn) is based on one or more characteristics of a gases flow provided to the patient.

In some configurations, the gases flow comprises a flow rate of about 5 litres/minute to about 150 litres/minute. In some configurations, the gases flow comprises a flow rate of about 20 litres/minute to about 90 litres/minute.

In some configurations, the gases flow comprises a flow rate of about 0.4 litres/minute/kilogram to about 8 litres/minute/kilogram with a minimum of about 0.5 litres/minute and a maximum of about 25 litres/minute.

In some configurations, the one or more characteristics of the gases flow comprises one or more of a flow rate, pressure, and humidity of the gases flow.

In some configurations, the CO2 clearance parameter (Jn) is further based on one or more of the patient's cardiogenic action and CO2 concentration in the patient's lungs.

In some configurations, the method further comprises determining one or more of:

a blood gases CO2 level at or during respiratory equilibrium where the CO2 production parameter (In) and the CO2 clearance parameter (Jn) are substantially the same;

a time point when the CO2 production parameter (In) and the CO2 clearance parameter (Jn) are substantially the same;

a length of time during which the CO2 production parameter (In) and the CO2 clearance parameter (Jn) are substantially the same; and a time point when the CO2 production parameter (In) is substantially greater than the CO2 clearance parameter (Jn) and the CO2 production parameter (In) is at a predetermined threshold.

In some configurations, the predetermined threshold is set by a user.

In some configurations, the CO2 production parameter (In) and the CO2 clearance parameter (Jn) are substantially the same when a difference between the CO2 production parameter (In) and the CO2 clearance parameter (Jn) falls within a predetermined tolerance range.

In some configurations, the CO2 production parameter (In) is substantially greater than the CO2 clearance parameter (Jn) when a difference between the CO2 production parameter (In) and the CO2 clearance parameter (Jn) falls outside a predetermined tolerance range.

In some configurations, the method further comprises determining a duration of safe apnoea, wherein the duration of safe apnoea includes the length of time until reaching the time point when the CO2 production parameter (In) is substantially greater than the CO2 clearance parameter (Jn) and difference meets or exceeds the predetermined threshold.

In some configurations, the method further comprises determining a pH value of the patient's blood based on the CO2 parameter value (Pn).

In some configurations, the determining an (n+1)th CO2 parameter value (Pn+1) comprises obtaining Pn+1 from a database based on one or more patient parameters of the patient.

In some configurations, the database comprises a relationship between the volume of CO2 stored and a blood gases CO2 level of the patient.

In some configurations, the database is generated based on one or more of the following patient parameters of the patient:

the patient's lung volume;
the patient's blood volume;
the patient's gender;
the patient's weight;
the patient's gender;
percentage of water in the patient's body excluding blood;
solubility of $CO_2$; and
percentage of blood $CO_2$ in haemoglobin.

In some configurations, the one or more patient parameters used to generate the database are referenced to a population dataset.

In some configurations, the method further comprises collecting patient data during a medical procedure to form the population dataset.

In some configurations, the $CO_2$ parameter values (P1-Pi) comprise one or more of $PaCO_2$, $PvCO_2$ and end tidal $CO_2$ (EtCO2).

In some configurations, the prediction of the progression of the patient blood gases $CO_2$ level from the time t1 to the time ti includes a time period when the patient is apnoeic during a medical procedure. In some configurations, the time period when the patient is apnoeic during a medical procedure includes the entirety of t1-ti.

In some configurations, the method further comprises determining one or more properties associated with a respiratory equilibrium based on the blood gases $CO_2$ level progression.

In some configurations, the determining one or more properties associated with a respiratory equilibrium comprises determining a rate of change of a $CO_2$ saturation parameter based on one or more of the $CO_2$ parameter values P1-Pi.

In some configurations, the one or more properties associated with a respiratory equilibrium comprise one or more of time to reach equilibrium, duration of equilibrium, equilibrium value, and rate of decline till equilibrium.

In some configurations, the one or more properties associated with a respiratory equilibrium comprise one or more of time to reach equilibrium, duration of equilibrium, equilibrium value, and rate of decline till equilibrium.

In some configurations, the method further comprises determining one or more properties associated with a duration of safe apnoea based on one or more of the $CO_2$ parameter values P1-Pi.

According to certain features, also disclosed are systems for performing any of the above methods.

Additionally, in accordance with certain features, aspects and advantages of at least one of the embodiments disclosed herein, a system comprises:

at least one input configured to receive information relating to one or more parameters associated with a patient;
at least one processor configured to:
obtain an nth $CO_2$ parameter value (Pn) relating to a patient blood gases $CO_2$ level at an nth time (tn)
determine an intermediate $CO_2$ parameter value (Vn);
determine an (n+1)th $CO_2$ parameter value (Pn+1) at an (n+1)th time (tn+1) based on the intermediate $CO_2$ parameter value (Vn); and
iterate the obtaining of the nth $CO_2$ parameter value (Pn), the determination of the intermediate $CO_2$ parameter value (Vn), and the determination of the (n+1)th $CO_2$ parameter value (Pn+1), to obtain a prediction of a progression of the patient blood gases $CO_2$ level from a time t1 to a time ti.

In some configurations, the input is configured to receive data from one or more patient sensors.

In some configurations, the input comprises a user interface.

In some configurations, the system further comprises a lung volume measurement device configured to estimate lung volume.

In some configurations, the system further comprises an output configured to provide information to a user. In some configurations, the output is configured to output an alarm.

In some configurations, the system further comprises a flow generator adapted to provide a flow of gases to the patient.

In some configurations, the processor is configured to cause the flow generator to control a flow of the gases to the patient.

In some configurations, the system further comprises a sealing or non-sealing patient interface adapted to attach to the patient and configured to deliver the gases to the patient.

In some configurations, the system further comprises a high flow respiratory therapy system. In some configurations, the system comprises a varying flow respiratory therapy system.

According to certain features, also disclosed are methods of using any of the above systems.

Additionally, in accordance with certain features, aspects and advantages of at least one of the embodiments disclosed herein, a method is disclosed of determining a patient blood gases oxygen (O2) level progression, the method comprising:

receiving an nth parameter value (Pn) relating to a blood gases O2 level of the patient at an nth time (tn);
obtaining a correction factor value (Cn);
determining an (n+1)th parameter value (Pn+1) relating to a blood gases O2 level of the patient at an (n+1)th time (tn+1) based on the correction factor (Cn); and
iterating said receiving an nth parameter value (Pn), said obtaining a correction factor value (Cn), and said determining an (n+1)th parameter value (Pn+1) to obtain a prediction of the blood gases O2 level progression in the patient from a time t1 to a time ti.

In some configurations, one or more of the parameter values (P1-Pi) comprise values obtained from a population dataset, measured, estimated, or calculated.

In some configurations, the first parameter value (P1) comprises an estimated value.

In some configurations, one or more of the correction factor values (C1-Ci) comprise values obtained from a population dataset, measured, estimated, or calculated.

In some configurations, the correction factor value (Cn) comprises a blood pH of the patient.

In some configurations, the correction factor value (Cn) comprises a blood alveoli pH of the patient.

In some configurations, the method further comprises obtaining the blood pH from a blood gases $CO_2$ level progression model.

In some configurations, the determining an (n+1)th parameter value (Pn+1) comprises obtaining Pn+1 from a database generated based on a relationship between the pH and a shift in p50 (the partial pressure of O2 required to achieve 50% haemoglobin saturation), optionally, from Bohr-shifted oxygen dissociation curve based on the blood pH and/or the shift in p50.

In some configurations, the database is generated based on parameters obtained from the patient or from a patient population.

In some configurations, the database is generated using one or more of the following parameters of the patient:

haemoglobin concentration;

cardiogenic gas exchange;

cardiac output;

metabolism;

an O2 storage efficiency of haemoglobin; and disease status.

In some configurations, the determining an (n+1)th parameter value (Pn+1) comprises determining Pn+1 based on one or more of the following patient characteristics:

the patient's alveolal partial pressure of O2 and CO2;

the patient's fraction of inspired O2 (FiO2);

a level of V/Q mismatch in the patient's lungs;

a cardiac action-related parameter of the patient;

disease state of the patient;

position of the patient during the medical procedure; and a substance administered to the patient.

In some configurations, the determining Pn+1 further comprises referencing the one or more patient characteristics to a population dataset.

In some configurations, the method further comprises obtaining a real-time measurement of one or more of the level of V/Q mismatch in the patient's lungs and the cardiac-action related parameter of the patient.

In some configurations, the method further comprises using a patient's body mass index (BMI) or body shape index (BSI) to determine one or more of the level of V/Q mismatch in the patient's lungs and the cardiac-action related parameter of the patient.

In some configurations, the one or more patient characteristics comprise are obtained from a population dataset, measured, estimated or calculated.

In some configurations, the method further comprises determining the patient's FiO2 based on a gases flow provided to the patient.

In some configurations, the method further comprises determining the patient's FiO2 based on one or more flow characteristics of a gases flow provided to the patient.

In some configurations, the gases flow comprises an O2 percentage of about 15% to about 100%.

In some configurations, the method further comprising obtaining the patient's alveolal partial pressure of CO2 from a blood gases CO2 level progression model.

In some configurations, the parameter value (Pn) comprises one or more of SpO2, PaO2, SvO2, and PvO2.

In some configurations, the determining an (n+1)th parameter value (Pn+1) comprises determining Pn+1 based on an O2 amount that is transmitted from the blood to the tissue.

In some configurations, the O2 amount transmitted is based on a cardiac output and a rate of removal of O2 from the blood.

In some configurations, the method is performed when the patient is apnoeic during a medical procedure.

In some configurations, the method further comprises determining one or more properties associated with a respiratory equilibrium based on the blood gases O2 level progression.

In some configurations, the determining one or more properties associated with a respiratory equilibrium comprises determining a rate of change of an oxygen saturation parameter based on one or more of the parameter values P1-Pi.

In some configurations, the one or more properties associated with the respiratory equilibrium comprises one or more of time to reach equilibrium, duration of equilibrium, equilibrium value, and rate of decline till equilibrium.

In some configurations, the method further comprises determining one or more properties associated with a duration of safe apnoea based on one or more of the parameter values P1-Pi.

In some configurations, the method further comprises collecting patient data to form a population dataset used in said determining an (n+1)th parameter value (Pn+1).

According to certain features, also disclosed are systems configured to perform any of the above methods.

Additionally, in accordance with certain features, aspects and advantages of at least one of the embodiments disclosed herein, a system comprises:

at least one input configured to receive information relating to one or more parameters associated with a patient;

at least one processor configured to:

receive an nth parameter value (Pn) relating to a blood gases O2 level of the patient at an nth time (tn);

obtain a correction factor value (Cn);

determine an (n+1)th parameter value (Pn+1) relating to a blood gases O2 level of the patient at an (n+1)th time (tn+1) based on the correction factor (Cn); and iterate the receiving of the nth parameter value (Pn), the obtaining of the correction factor value (Cn), and the determination of the (n+1)th parameter value (Pn+1) to obtain a prediction of the blood gases O2 level (Pn+i) progression in the patient.

In some configurations, the input is configured to receive data from one or more patient sensors. In some configurations, the input comprises a user interface.

In some configurations, the system further comprises a lung volume measurement device configured to estimate lung volume.

In some configurations, the system further comprises an output configured to provide information to a user. In some configurations, the output is configured to output an alarm.

In some configurations, the system further comprises a flow generator adapted to provide a flow of gases to the patient. In some configurations, the processor is configured to cause the flow generator to control a flow of the gases to the patient. In some configurations, the system further comprises a sealing or non-sealing patient interface adapted to attach to the patient and configured to deliver the gases to the patient.

In some configurations, the system comprises a high flow respiratory therapy system. In some configurations, the system comprises a varying flow respiratory therapy system.

According to certain features, also disclosed are methods of using any of the above systems.

It should be understood that alternative embodiments may comprise any or all combinations of two or more of the parts, elements or features illustrated, described or referred to in this specification.

BRIEF DESCRIPTION OF THE DRAWINGS

Specific embodiments and modifications thereof will become apparent to those skilled in the art from the detailed description herein having reference to the figures that follow, of which:

FIG. 12 is a schematic diagram showing respiratory equilibrium and safe apnoea calculations at different stages of an operation, according to certain embodiments.

FIGS. 15A-15C show examples of methods of predicting blood gas $CO_2$ (FIG. 15A) and/or $O_2$ levels (FIGS. 15A-15C) during a medical procedure or other apnoeic conditions.

DETAILED DESCRIPTION OF SPECIFIC EMBODIMENTS

Figure 1:
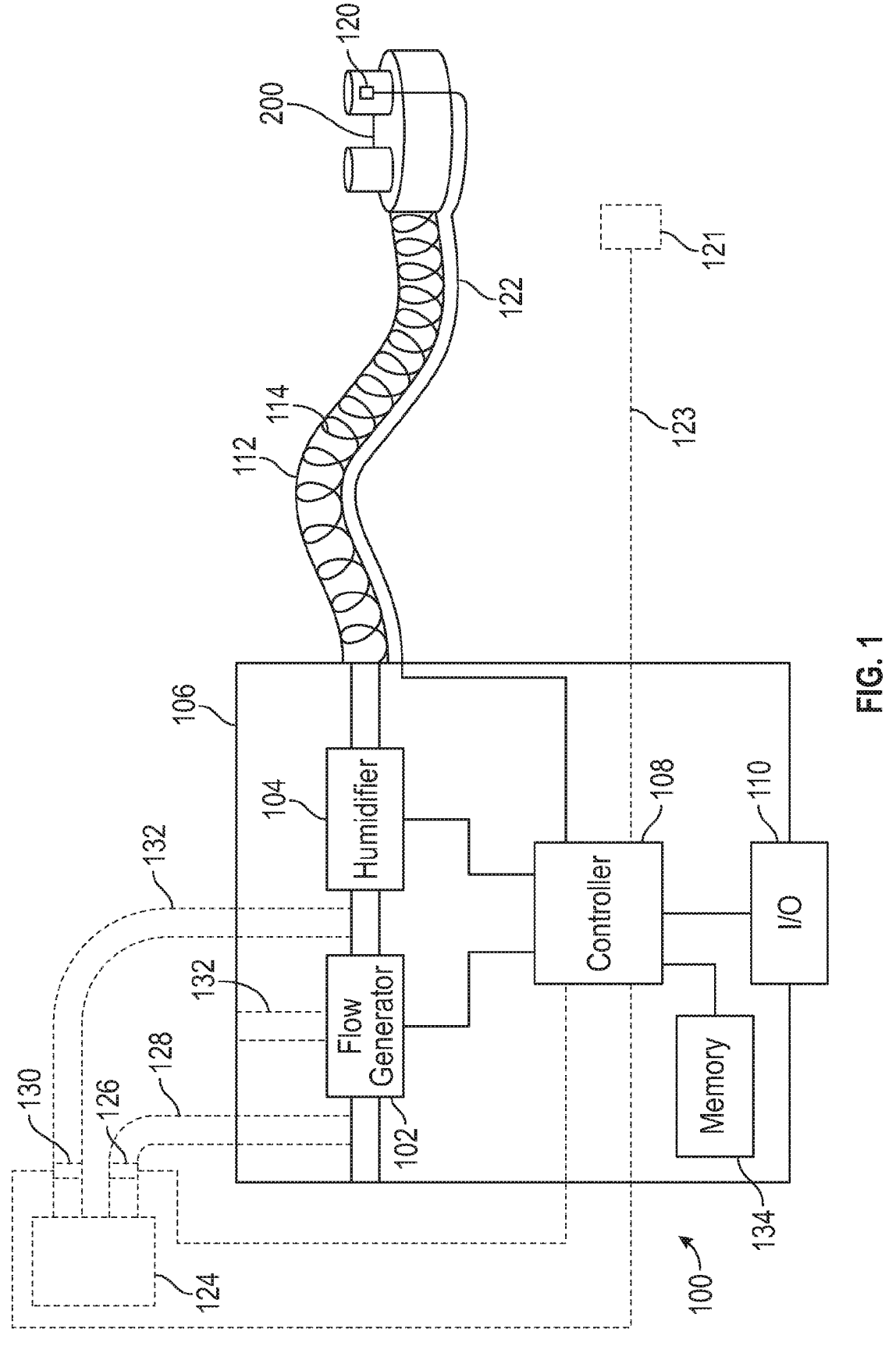
FIG. 1 shows a respiratory therapy system according to certain embodiments.

With reference to the non-limiting exemplary embodiment shown in FIG. 1, a respiratory therapy system 100 is shown. The respiratory therapy system 100 comprises a flow generator 102. The flow generator 102 is configured to generate gas flows that are passed through the respiratory therapy system 100. The flow generator 102 passes the air to a humidifier 104.

The humidifier 104 is configured to heat and humidify gas flows generated by the flow generator 102. In some configurations, the flow generator 102 comprises a mechanical blower adapted to receive gases from the environment outside of the respiratory therapy system 100 and propel them through the respiratory therapy system 100. In some configurations the flow generator 102 may deliver a flow of gases which is oscillating or has oscillating components.

In some configurations, the flow generator 102 may comprise some other gas generation means. For example, in some configurations, the flow generator 102 may comprise one or more containers of compressed air and/or another gas and one or more valve arrangements adapted to control the rate at which gases leave the one or more containers. As another example, in some configurations, the flow generator 102 may comprise an oxygen concentrator. In some configurations, the flow generator 102 may be adapted to deliver a high flow therapy. 'High flow therapy' as used in this disclosure may refer to delivery of gases to a patient at a flow rate of greater than or equal to about 10 litres per minute (10 LPM). In some configurations, 'high flow therapy' may refer to the delivery of gases to a patient at a flow rate of between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. 'High flow therapy' may also for example, according to various embodiments and configurations described herein, be a flowrate of gases supplied or provided to an interface or via a system, such as through a flow path, but is not limited to, flows of at least about 5, 10, 20, 30, 40, 50, 60, 70, 80, 90, 100, 110, 120, 130, 140, 150 L/min (LPM), or more, and useful ranges may be selected between any of these values (for example, between about 40 LPM to about 80 LPM, or between about 50 LPM to about 80 LPM, or between about 60 LPM to about 80 LPM, or between about 70 LPM to about 80 LPM, or between about 5LPM and about 150 LPM, or between 10 LPM and about 150 LPM, or between about 15 LPM and about 150 LPM, or between about 20 LPM and about 150 LPM, or between about 20 LPM and about 120 LPM, or between about 30 LPM and about 120 LPM, or between about 20 LPM and about 100 LPM, or between about 20 LPM and about 90 LPM, or between about 25 LPM and about 85 LPM, or between about 30 LPM and about 80 LPM or between about 30 LPM and about 90 LPM, or between about 35 LPM and about 75 LPM, or between about 40 LPM and about 70 LPM, or between about 45 LPM and about 65 LPM, or between about 50 LPM and about 60 LPM).

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal peak inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

Figure 14:
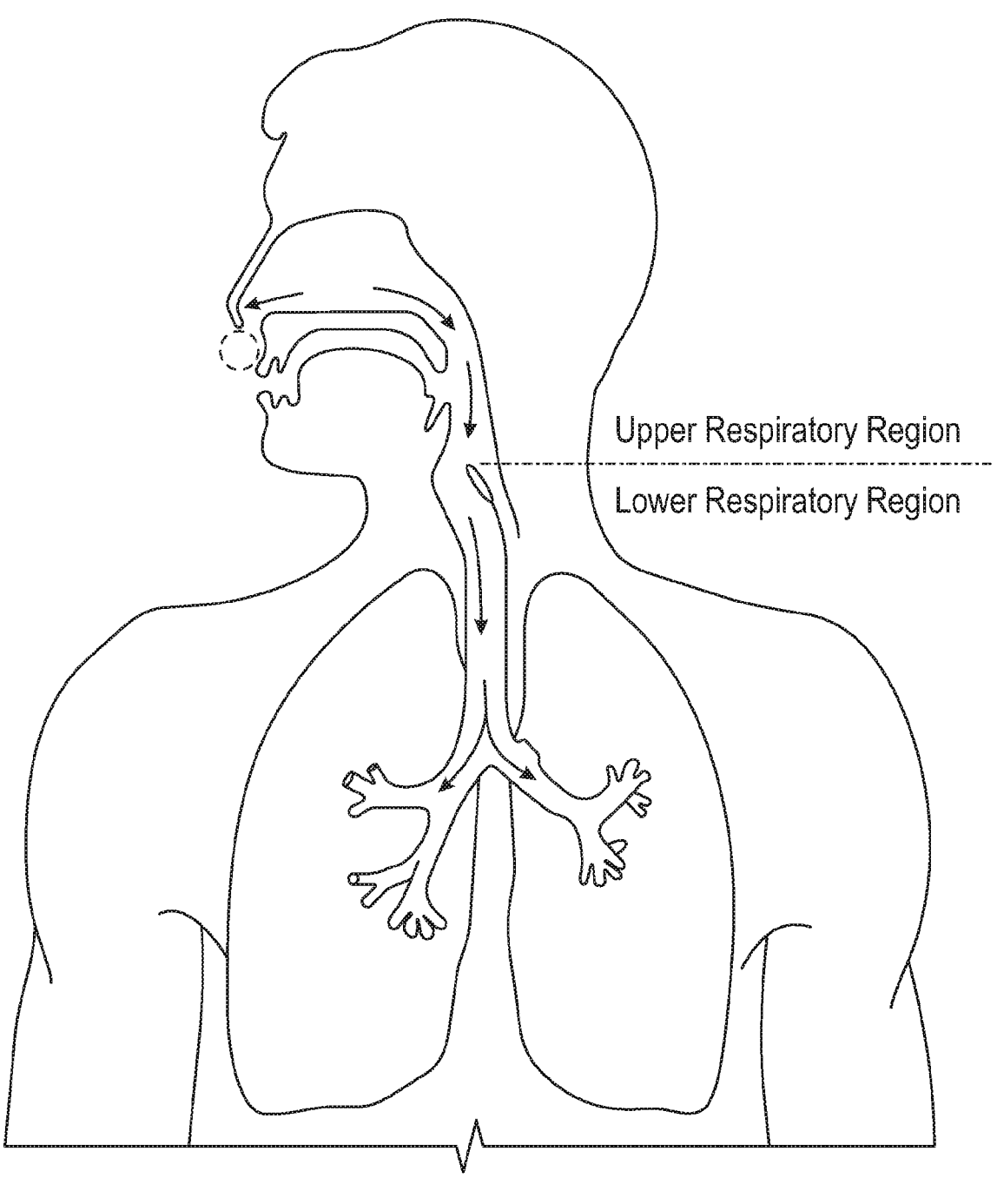
FIG. 14 shows a typical airway of a person, and includes arrows to indicate how a relatively high flowrate of gases supplied to a user may be utilised to effectively push or drive the supplied gases further or deeper into a user's airway than when the person is under normal or typical self-driven respiratory conditions.

FIG. 14 shows a typical airway of a person, and shows the direction of inward airflow during a patient's normal breathing. The arrows also indicate how a relatively high flowrate of gases supplied to a user may be utilised to effectively push or drive the supplied gases further or deeper into a user's airway than when the user is receiving a low flow rate of gases, or when the patient is apnoeic.

The respiratory therapy system 100 comprises a housing 106 that at least partially houses both the flow generator 102 and the humidifier 104 (e.g. the respiratory therapy system 100 may comprise an integrated flow generator/humidifier apparatus). In other configurations the flow generator 102 and humidifier 104 may have separate housings. The humidifier 104 will provide the benefit of reducing drying of airways. However, the humidifier is optional, and the delivered gases do not need to be humidified.

The system 100 comprises a hardware controller 108, referred to interchangeably herein as a "processor" which can be any appropriate type of processor, which is in electronic communication with the flow generator 102 and the humidifier 104, although in some configurations the hardware controller 108 might only communicate with the flow generator 102 or the humidifier 104. The hardware controller 108 may comprise a microcontroller or some other architecture configured to direct the operation of controllable components of the respiratory therapy system 100, including but not limited to the flow generator 102 and/or the humidifier 104. The controller 108 can implement any of the techniques described herein including any of the techniques for predicting respiratory equilibrium, duration of safe apnoea, and other related parameters. The system 100 can also include memory 134 which can be included in the housing 106 for example, and can be in communication with the controller 108.

An input/output module 110 is shown to be in electronic communication with the controller 108. The input/output module 110 may be configured to allow a user to interface with the controller 108 to facilitate the control of controllable components of the respiratory therapy system 100, including but not limited to the flow generator 102 and/or the humidifier 104, and/or view data regarding the operation of the respiratory therapy system 100 and/or its components. The input/output module 110 might comprise, for example, one or more buttons, knobs, dials, switches, levers, touch screens, speakers, displays and/or other input or output peripherals that a user might use to view data, input parameters for processing and/or input commands to control components of the respiratory therapy system 100.

As further shown in FIG. 1, a supplementary gas source 124 may be used to add one or more supplementary gases to the gases flowing through the respiratory therapy system 100. The one or more supplementary gases join the gas flow generated by the flow generator 102. The supplementary gas source 124 may be configured to deliver one or more supplementary gases including but not limited to air, oxygen ($O_2$), carbon dioxide ($CO_2$), nitrogen ($N_2$), nitrous oxide (NO), and/or heliox (a mixture of helium and oxygen). The supplementary gas source 124 may deliver the one or more supplementary gases via a first supplementary gas lumen 128 to a location upstream of the flow generator 102, and/or may deliver the one or more supplementary gases via a second supplementary gas conduit 132 to a location downstream of the flow generator 102 and/or upstream of the humidifier 104.

The system 100 includes one or more supplementary flow valves 126, 130 may be used to control the rates at which the one or more supplementary gases can flow from the supplementary gas source 124 and through the first and/or second supplementary gas conduits 128, 132. The one or more of the supplementary flow valves 126, 130 may be in electronic communication with the controller 108, which may in turn control the operation and/or state of the one or more of the supplementary flow valves 126, 130.

In other configurations, the supplementary gas source 124 may be configured to add one or more supplementary gases downstream of the humidifier 104. The supplementary gas source 124 may be delivered by an independent system that is not used with the same flow generator 102. The supplementary gas source may be used in an anaesthetic gas delivery system which has an independent flow generator, and the gas is circulated.

As shown in FIG. 1, the system includes a conduit 112 extending from the humidifier 104 and links the humidifier 104 to a patient interface 200. The conduit 112 may comprise a conduit heater 114 adapted to heat gases passing through the conduit 112. In other configurations the conduit heater 114 may not be present. The patient interface 200 is shown to be a nasal cannula, although it should be understood that in some configurations, other patient interfaces may be suitable. For example, in some configurations, the patient interface 200 may comprise a sealing or non-sealing interface, and may comprise a nasal mask, an oral mask, an oro-nasal mask, a full face mask, a nasal pillows mask, a nasal cannula, an endotracheal tube, a buccal tube, a combination of the above or some other gas conveying system. In a preferred embodiment, the patient interface 200 is a non-sealing interface such as a nasal cannula, which allows gases to be exchanged with the environment. For example, the non-sealing cannula allows carbon dioxide to be removed and/or cleared from the patient's airways while the patient receives flow therapy from the system 100. Further, in the preferred embodiment, the patient interface 200 is in the form of a nasal interface, such that the system does not interfere with other oral airway equipment and/or devices, for example, a tracheal tube in an intubation procedure. Accordingly, the patient may continue to receive flow therapy throughout the intubation procedure.

As shown, in some configurations the patient interface 200 may also comprise a gas sensing module 120 adapted to measure a characteristic of gases passing through the patient interface 200. In other configurations the gas sensing module 120 could be positioned and adapted to measure the characteristics of gases at or near other parts of the respiratory therapy system 100. An example of such a configuration involves the gas sensing module 120 being located within the housing 106. The gas sensing module 120 may comprise one or more sensors adapted to measure various characteristics of gases, including but not limited to pressure, flow rate, temperature, absolute humidity, relative humidity, enthalpy, gas composition, oxygen concentration, carbon dioxide concentration, and/or nitrogen concentration. Gas properties determined by the gas sensing module 120 may be utilized in a number of ways, including but not limited to closed loop control of parameters of the gases. For example, in some configurations flow rate data taken by a gas sensing module 120 may be used to determine the instantaneous flow, which in turn may be used to determine the respiratory cycle of the patient to facilitate the delivery of flow in synchronicity with portions of the respiratory cycle. The gas sensing module 120 may communicate with the controller 108 over a first transmission line 122. In some configurations, the first transmission line 122 may comprise a data communication connection adapted to transmit a data signal. The data communication connection could comprise a wired data communication connection such as but not limited to a data cable, or a wireless data communication connection such as but not limited to Wi-Fi or Bluetooth. In some configurations, both power and data may be communicated over the same first transmission line 122. For example, the gas sensing module 120 may comprise a modulator that may allow a data signal to be 'overlaid' on top of a power signal. The data signal may be superimposed over the power signal and the combined signal may be demodulated before use by the controller 108. In other configurations the first transmission line 122 may comprise a pneumatic communication connection adapted to transmit a gas flow for analysis at a portion of the respiratory therapy system 100.

Additionally as shown the system 100 can include a physiological sensor module 121. The physiological sensor module 121 may be configured to detect various characteristics of the patient or of the health of the patient, including but not limited cardiac output (such as to heart rate), blood pressure, EEG signal, EKG/ECG signal, blood gas concentration such as blood oxygen concentration or a parameter relating to blood oxygen concentration (via, for example, a pulse oximeter or a direct sensing line), blood $CO_2$ concentration or a parameter relating to blood $CO_2$ concentration, transcutaneous $CO_2$ ($TcCO_2$) or $O_2$ ($TcO_2$), expelled $CO_2$ or $O_2$, oxygen saturation via, for example, a pulse oximeter or a direct sensing line, and/or blood glucose. Similarly, the physiological sensor module 121 may communicate with the controller 108 over a second transmission line 123. The second transmission line 123 may comprise wired or wireless data communication connections similarly to the first transmission line 122, and power and data may be communicated similarly. The physiological sensor module 121 may be used, for example, to determine the blood oxygen saturation of the patient.

Figures 2, 3:
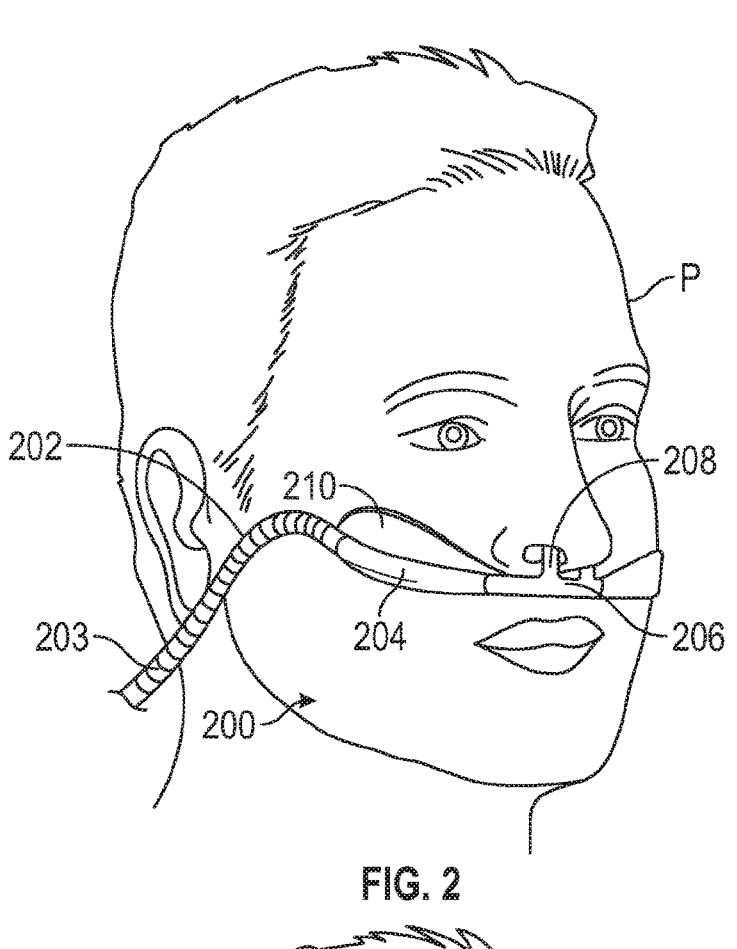
FIG. 2 shows a patient wearing a patient interface.
FIG. 3 shows a patient wearing a patient interface and a face mask, which can be connected to a second respiratory system such as an anaesthetic machine.

FIG. 2 shows a patient P wearing a patient interface 200. In the illustrated non-limiting configuration, the patient interface 200 is a nasal cannula. The patient interface 200 comprises a first gas lumen 202 defined by a tubular wall. The first gas lumen 202 is adapted to receive gases from the respiratory therapy system 100 (for example, via the conduit 112 shown in FIG. 1) and channel the gases to the patient P. The illustrated first gas lumen 202 is defined at least in part by a wall within which gases can be channeled. The first gas lumen 202 may comprise a reinforcement element 203 adapted to strengthen and/or add rigidity to the first gas lumen 202 to prevent deformation or collapse of the first gas lumen 202 arising due to the application of forces against the first gas lumen 202. The reinforcement element 203 may include a number of structures, including but not limited to plastic or metallic reinforcing beads that lie in or on the wall of the first gas lumen 202.

The first gas lumen 202 is in pneumatic communication with a flow manifold 206. The flow manifold 206 receives gases from the first gas lumen 202 and passes them to one or more nasal delivery elements 208 (e.g. prongs). The one or more nasal delivery elements 208 extend outwardly from the flow manifold 206. The one or more nasal delivery elements 208 are adapted to be non-sealingly positioned in one or more nares of the patient P. As shown, the patient interface 200 comprises two nasal delivery elements 208 adapted to be positioned one in each of the patient's nares. Each nasal delivery element 208 may be shaped or angled such that it extends inwardly towards a septum of the patient's nose.

Additionally, each nasal delivery element may be shaped or angled such that a tip of each nasal delivery element points, in use, towards a back of the head of the patient P. In the embodiment shown in FIG. 2, the flow manifold 206 receives flow from one lateral side of the flow manifold 206

(e.g. with respect to an imaginary vertical plane bisecting the face of the patient P) and channels flow to each of the nasal delivery elements 208. In other configurations, the patient interface 200 may comprise greater (for example, three or four) or fewer (for example, one) nasal delivery element 208.

In other configurations, each nasal delivery elements 208 can have different properties. For example, one of a pair of nasal delivery elements 208 can be relatively long and the other nasal delivery element 208 can be relatively short. In some configurations, the flow manifold 206 may be configured to receive flow from two lateral sides of the flow manifold 206 (e.g. from a 'left' and 'right' of the flow manifold 206 when instead of just the 'left' of the flow manifold 206 as seen in FIG. 2). In some such configurations, multiple gas lumens may be used to provide for pneumatic communication between the flow manifold 206 and the respiratory therapy system 100. In some configurations, the flow manifold 206 may be configured to receive flow from a non-lateral side of the flow manifold 206 (e.g. from a 'bottom' or 'top' of the flow manifold 206).

The patient interface 200 may further comprise mounts and/or supports, e.g., cheek supports 210, for attaching and/or supporting the gas lumen 202 on the patient's face. Additionally, the patient interface 200 may comprise a headgear or head straps to attach and/or support the patient interface 200 (including the gas lumen 202) on the patient's face.

FIG. 3 shows a non-limiting exemplary embodiment of a patient P wearing the patient interface 200 as shown in FIG. 2 underneath a face mask 300 assembly. FIG. 3 schematically shows the face mask as a transparent structure in order to illustrate the patient interface 200 under it.

Face mask assembly 300 may be used as a second respiratory support subsystem and/or to deliver one or more other substances, for example anaesthetic agents, to the patient. Accordingly, the embodiment shown in FIG. 3 allows for the delivery of gas from multiple sources via two respiratory support subsystems. Additionally, this configuration may allow the patient interface 200 to be left on the patient throughout the surgical procedure and/or into recovery (whether or not the patient continues to receive flow therapy through the patient interface 200 throughout the procedure).

In the embodiment shown, face mask assembly 300 comprises a full face mask 302 configured to cover both the patient's nose and mouth. In other configurations, the face mask 300 may be a nasal mask which is placed over the patient interface 200 to cover only the patient's nasal region.

As shown, the face mask 302 comprises a seal region 304 adapted to seal against the patient's face. The face mask assembly 300 is connected to a transmission line 310 such as a hose or tube, which is connected to a second respiratory system 312 that provides a second gas source which supplies the one or more other gases to the patient via the face mask. That is, second gas source is preferably different from the source supplying gas (for example, supplementary gas source 124) to the patient interface 200.

The second respiratory system 312 connected to the face mask assembly 300 can be a separate gas source or respiratory support device. For example, the second respiratory system 312 can be a ventilator or a CPAP or a high flow therapy device.

Alternatively the second respiratory system 312 to which the mask 300 is connected could be an anaesthetic device, and anaesthetic gas can be delivered via the mask 302.

The embodiment shown in in FIG. 3 allows for the delivery of gas from multiple sources via at least two different respiratory support modes, and further allows a doctor, clinician or medical professional to quickly and easily change the type of respiratory support mode.

Figure 3A:
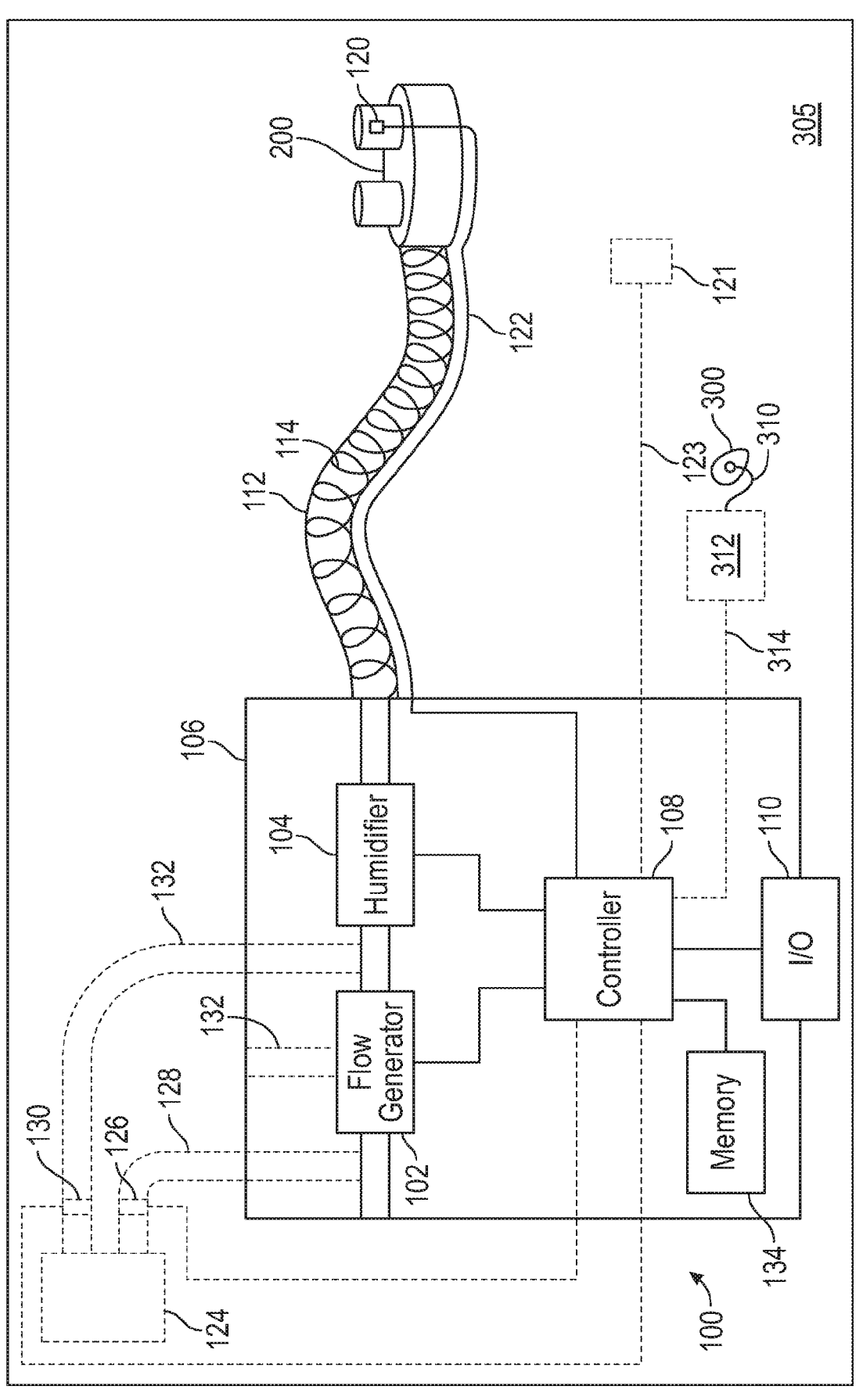
FIG. 3A shows a respiratory therapy system including a second respiratory system, such as an anaesthetic machine.

FIG. 3A shows another example of a system 305 including a first respiratory device 100, which can be similar to or the same as the respiratory therapy system 100 shown in FIG. 1. The system 305 further includes a second respiratory system 312 connected to mask 300 via the transmission line 310. As shown, the second respiratory system 312 can be connected via wireless or wired connection 314 to the first respiratory system 100, and can be in communication with the processor 108.

With the advent of nasal high flow and its intended use in the anaesthesia setting the user of the system would want an estimate for how long an apnoeic period would be safe. The following embodiments relate to different systems and methods for monitoring an apnoeic period and predicting or determining the duration of safe apnoea. It should be noted these systems and methods are not exclusive to anaesthesia and nasal high flow. The methods could also be used for apnoeic periods in a general respiratory setting and/or when different respiratory support mechanisms are used.

Embodiments may be used to pre-predict a duration of safe apnoea before apnoea occurs and/or may be used to monitor or record apnoea trends during a medical procedure.

Certain embodiments relate to determining one or more properties relating to a patient's respiratory equilibrium, which can be used in making safe apnoea determinations including predicting a duration of safe apnoea. Such techniques relating to the prediction/monitoring of respiratory equilibrium are described below with respect to FIGS. 9-12 and can utilize any of the techniques for determining a duration of safe apnoea described elsewhere herein, such as with respect to FIGS. 4-7. Techniques for determining safe apnoea that can be incorporated into the systems and methods described herein can also be found in PCT Application Serial No. PCT/IB2018/052387, entitled Flow Therapy System and Method, which is hereby incorporated by reference in its entirety herein.

Some or all of the embodiments will be performed by one or more processors. The processor may be the hardware controller 108 of the respiratory therapy system 100. Alternatively, the processor may be one or more other hardware processors. Alternatively, the embodiments may be performed by the controller 108 along with one or more other processors.

Some or all of the embodiments comprise obtaining and/or receiving information relating to one or more parameter or indicator (such as a respiratory parameter/indicator and/or a physiological parameter/indicator), and determining a duration of safe apnoea from the obtained information. Where the term 'indicator' is used, reference to 'indicator' may refer to either or both of a respiratory indicator and/or a physiological indicator.

The respiratory therapy system comprises one or more patient interfaces, and a processor configured to update, predict and/or determine one or more properties associated with an apnoeic respiratory equilibrium and/or a duration of safe apnoea based on obtained information relating to one or more respiratory indicators. Additionally, or alternatively the processor may be configured to update, predict and/or determine one or more properties associated with an apnoeic respiratory equilibrium and/or a duration of safe apnoea based on obtained information relating to one or more physiological indicators.

Techniques for Determining Duration of Safe Apnoea

Figure 4:
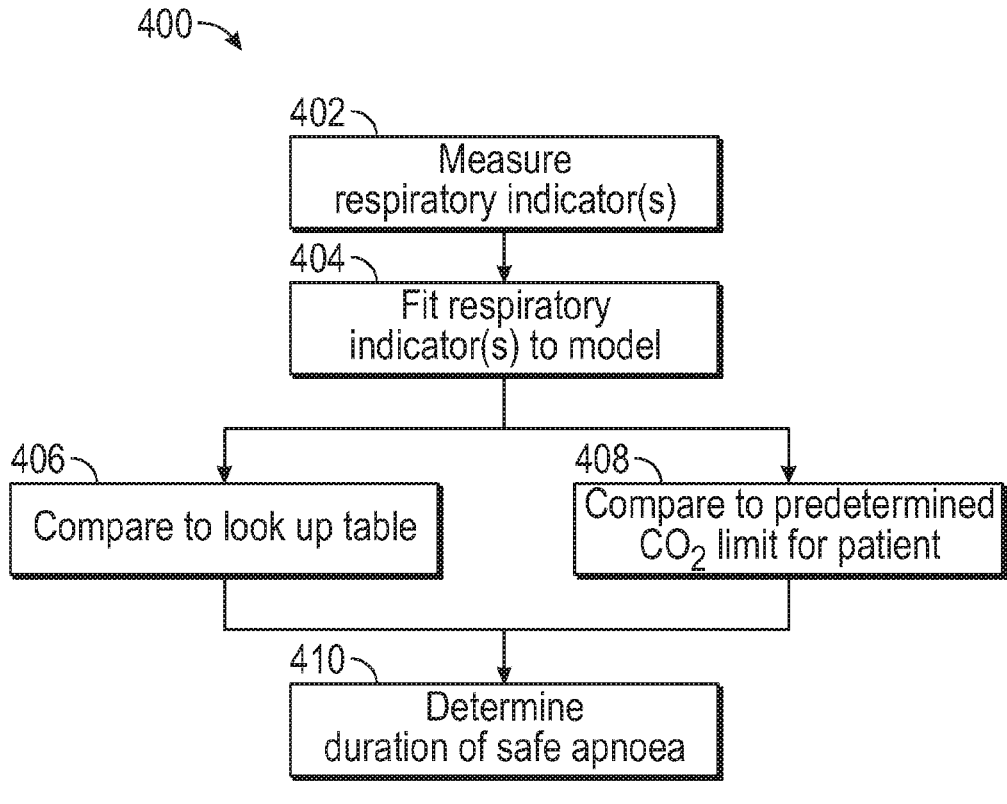
FIG. 4 is a flow chart schematically showing a first embodiment of a method of predicting or determining duration of safe apnoea.
Figure 5:
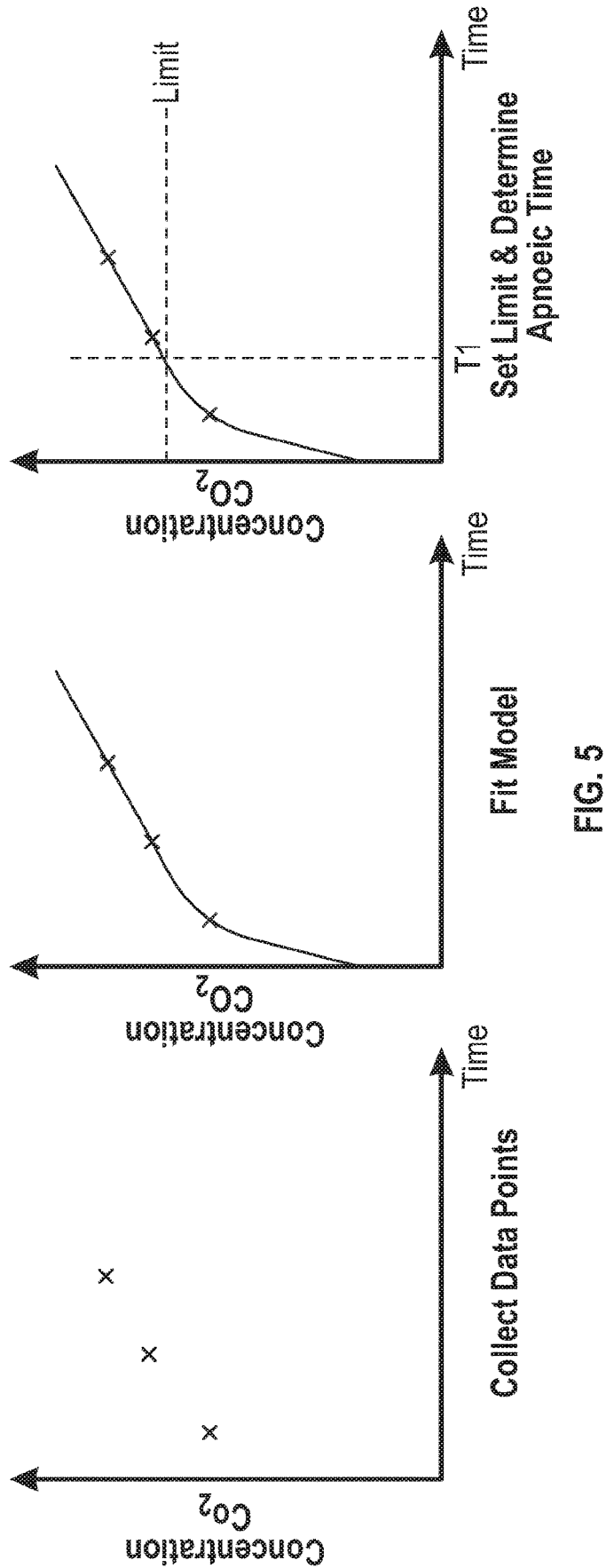
FIG. 5 shows plots representing various stages of the method of FIG. 4.

FIGS. 4 and 5 schematically show a first embodiment method 400 for predicting or determining a duration of safe apnoea. In a first step 402, this method comprises measuring an indicator of a patient. The indicator may be any suitable indicator such as carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V)–perfusion (Q)), heart rate, blood pressure, or metabolic rate for example. Additionally, a parameter relating to the opening of alveoli may be measured. The indicator (such as a respiratory indicator and/or a physiological indicator) may be measured by one or more suitable sensors, which may be the sensors 120, 121 in the respiratory therapy system or may be additional or alternative sensors. The measurements from the sensor(s) may be recorded automatically by the processor 108, or may be recorded by an operator and input to the processor via a user interface such as a keyboard or touch screen.

In apnoea, there is a reduced capacity for carbon dioxide ($CO_2$) to be removed from the lungs and it accumulates in the blood, or there is not enough oxygen being supplied to the lungs and/or blood. A greater lung volume generally means a greater presence of $O_2$ which should result in a longer duration of safe apnoea. Lung volume may be measured by electrical impedance tomography (EIT) or another method. Measuring the patient's carbon dioxide and comparing or fitting a model to it may be used to determine the duration of safe apnoea. Such a process is shown schematically in FIG. 5. As shown in FIG. 5(*a*), a plurality of carbon dioxide concentration measurements are taken at different times. Carbon dioxide concentration may be measured based on expired carbon dioxide, transcutaneous carbon dioxide, or blood gases for example.

The processor determines the duration of safe apnoea from the measured indicator (such as a respiratory indicator and/or a physiological indicator), for example carbon dioxide. The processor 108 may compare or fit 404 the measured indicator to a model, as shown in FIG. 5(*b*).

Once compared or fit to the model, the processor 108 may determine the duration of safe apnoea based on a maximum carbon dioxide limit in the model. This is shown in FIG. 5(*c*). In one configuration 406, the processor may determine the maximum carbon dioxide limit from a look up table with predetermined different safe carbon dioxide limits. The processor may be pre-programmed with a look up table. Alternatively, the processor may access a look up table and perform a comparison with the look up table. The safe carbon dioxide limits in the look up table may be based on one or more of:

disease (for example chronic obstructive pulmonary disease, emphysema, asthma etc.);
age;
height;
weight;
BMI (Body Mass Index) or BMI distribution;
body shape or BSI (Body Shape Index);
cardiac output;
pregnancy status;
difficult airway type;
treatment history (e.g., type and/or amount of drugs administered to a patient); and
clinical history (for example, of acidosis).

In an embodiment, the safe carbon dioxide limit can be calculated in real time for a patient based on one or more of these parameters. These parameters may be inputted into the processor and used to calculate the safe carbon dioxide limit.

In another configuration 408, the maximum carbon dioxide limit in the model may be a predetermined maximum carbon dioxide limit for the specific patient. The maximum carbon dioxide limit may be entered to the processor via a user interface. The carbon dioxide limit may be a clinical parameter entered by a user for example a clinician. Alternative 408 may be used as a preferred option for a conscious patient, with alternative 406 used if the patient is unconscious.

The processor may then determine 410 the duration of safe apnoea, the apnoeic respiratory equilibrium, or both, based on the maximum carbon dioxide limit and the model. While the process shown in FIG. 5 has various plots, it will be appreciated by a skilled person that actual plots will not necessarily be provided, and the processor 108 may perform the method using suitable calculations and/or steps. However, the plots are analogous of the process that may be performed by the processor 108.

Instead of measuring carbon dioxide, the method may be performed based on a different indicator such as, respiratory rate, oxygen concentration, arterial oxygen or carbon dioxide content, lung volume, lung compliance, lung/airway pressure, airway resistance/patency, metabolic rate, V/Q mismatch (ventilation (V)–perfusion (Q)), heart rate, blood pressure, or metabolic rate. The steps of the method may correspond to those outlined above. When using measured oxygen concentration as the indicator, oxygen concentration may be measured based on expired oxygen, transcutaneous oxygen, blood gases, haemoglobin oxygen concentration, blood pressure, arterial partial pressure of oxygen, or arterial oxygen content. Arterial oxygen content may be determined as (haemoglobin concentration×1.34×arterial oxygen saturation)+(0.0031×partial pressure of oxygen).

V/Q mismatch, also known as shunt, occurs if gas exchange doesn't take place when blood goes past the lungs. This may lead to $CO_2$ accumulating in the blood and/or not enough $O_2$ in the blood. V/Q mismatch is caused by anything that increases or decreases ventilation or perfusion of the lungs. For example, V/Q mismatch could be caused by a condition that does not cause a corresponding proportional increase in perfusion when ventilation is increased. This may occur due to gravity or due to a certain blood flow pattern or from atelectasis. If the oxygen being delivered to a patient is increased but more oxygen is not appearing in the blood, then this indicates there is a V/Q mismatch.

Alternatively, the method may comprise measuring a plurality of indicators, for example one or more respiratory indicators and/or physiological indicators of the patient.

The plurality of indicators may comprise two or more of carbon dioxide concentration or carbon dioxide clearance, respiratory rate, oxygen concentration, arterial oxygen or carbon dioxide content, lung volume, lung compliance, lung/airway pressure, airway resistance/patency, V/Q mismatch (ventilation (V)— perfusion (Q)), heart rate, blood pressure, or metabolic rate. For example, carbon dioxide may be measured in addition to one or more of the listed indicators.

When a plurality of indicators are measured, the processor may determine an average duration of safe apnoea from the plurality of measured indicators. Alternatively, the processor may determine a plurality of durations of safe apnoea from the plurality of measured respiratory indicators and/or measured physiological indicators and the processor may then be configured to select the shortest duration of safe apnoea from the plurality of measured respiratory indicators.

Figures 6, 6A, 6B:
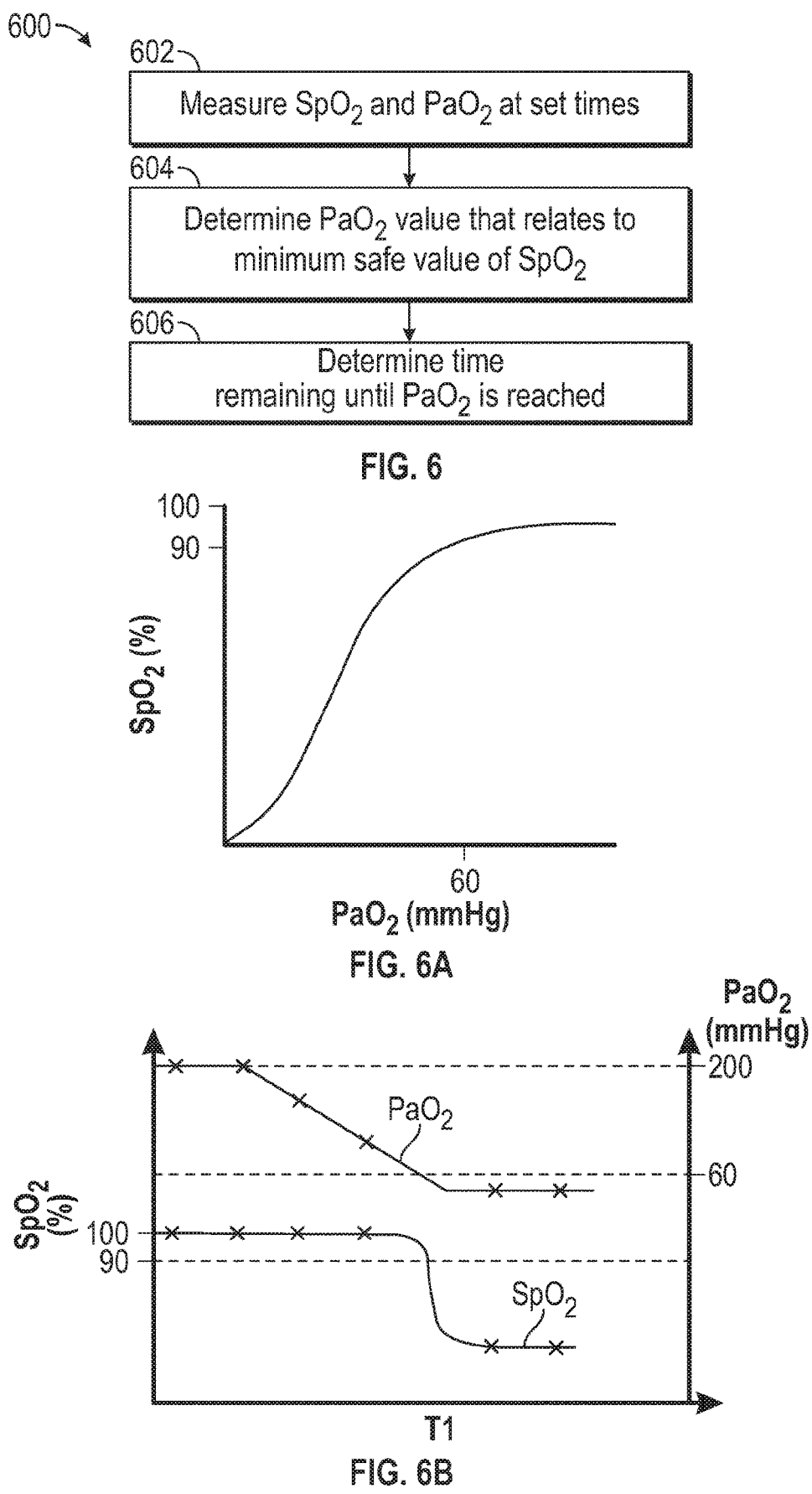
FIG. 6 is a flow chart showing a second embodiment of a method of predicting or determining a duration of safe apnoea.
FIG. 6A is an example of a graph showing the relationship between $SpO_2$ to $PaO_2$.
FIG. 6B is an example of a graph showing the variance in $PaO_2$ and $SpO_2$ over time.

FIG. 6 schematically shows a second embodiment method 600 for predicting or determining a duration of safe apnoea. This method comprises determining a duration of safe apnoea based on a relationship between a patient's haemoglobin oxygen saturation ($SpO_2$) and arterial partial pressure of oxygen ($PaO_2$). In an anaesthetised patient, the oxygen consumption remains fairly constant. This oxygen is delivered to the tissues by haemoglobin. The oxygen in the haemoglobin is then replenished, on return to the pulmonary circulation, by the diminishing store of oxygen within the lungs. The haemoglobin oxygen saturation remains greater than 90% as long as the haemoglobin can be re-oxygenated in the lungs. The $SpO_2$ only starts to decrease when the store of oxygen in the lungs is depleted. However the $PaO_2$ decreases in direct relation to the diminishing store of oxygen within the lungs.

An oxyhaemoglobin dissociation curve mathematically equates $SpO_2$ to $PaO_2$. A typical curve showing the relationship between $SpO_2$ to $PaO_2$ is shown in FIG. 6A. As the duration of a safe apnoea can be defined by the de-saturation, a patient specific dissociation curve can be used to estimate the relationship between $SpO_2$ to $PaO_2$ and the remaining safe apnoea time. A threshold $SpO_2$ may be input by a clinician or determined based on a particular patient and or their characteristics. The $SpO_2$ threshold may correspond with the safe threshold of $SpO_2$ for a patient, below which a patient will be considered to have desaturated. The $SpO_2$ threshold may be for example 90% (as for example shown in FIGS. 6A and 6B).

FIG. 6B shows $PaO_2$ and $SpO_2$ over time during an apnoea event as may be for example measured by method 600. FIG. 6B shows a patient with an initial SpO2 of about 100%, and an initial PaO2 of about 200 mmHg. Once the apnoea event begins the patient's PaO2 decreases as oxygen is consumed but not replaced. FIG. 6B shows that even though PaO2 is decreasing no corresponding decrease in SpO2 is initially observed. Once a decrease of SpO2 is observed it can often be too late, and the patient can desaturate rapidly. Further, due to the rapid decrease of SpO2 no warning of patient desaturation is provided.

In some configurations, the safe apnoea time may be based on a threshold arterial partial pressure of oxygen (PaO2). The threshold arterial oxygen content may be determined from a threshold haemoglobin oxygen saturation (SpO2) as described above, and as shown in FIG. 6A. For example as shown in FIGS. 6A and 6B one example threshold haemoglobin oxygen saturation (SpO2) is 90%, which corresponds to 60 mmHg $PaO_2$.

In some configurations, the duration of safe apnoea is based on, or may be equal to, a length of time until the arterial partial pressure of oxygen reaches (or optionally goes below) the threshold arterial partial pressure of oxygen. The length of time until the arterial partial pressure of oxygen reaches the threshold arterial partial pressure of oxygen may be determined by measuring or estimating a rate of change of arterial partial pressure of oxygen. For example in FIG. 6B the length of time until the arterial partial pressure of oxygen reaches the threshold arterial partial pressure of oxygen (or the duration of safe apnoea) is T1. At the time T1 the arterial partial pressure of oxygen may be 60 mmHG, which corresponds to a haemoglobin oxygen saturation ($SpO_2$) of 90%, as determined from FIG. 6A

In a first step 602, a patient's $SpO_2$ and $PaO_2$ are measured at set times. This generates a set of points on the dissociation curve, and a sigmoidal shape can then be fitted to the points. These data points and/or the resulting fitted curve may include correction factors for temperature, pH, $PaCO_2$, and/or the characteristics of the patient's haemoglobin. Such correction factors address the left or right-hand shifts of the curve, also known as Bohr/Haldane shifts, as such shifts could significantly change the safe apnoea time.

The $SpO_2$ may be measured by or inferred from pulse oximetry. The $PaO_2$ may be measured using blood gases or by inferring the $PaO_2$ from a transcutaneous oxygen measurement, by pulse oximetry, or other methods known in the art.

The processor 108 may then determine 604 an $PaO_2$ that relates to a specified minimum safe value of $SpO_2$. The minimum safe value of $SpO_2$ may be a predetermined value or alternatively may be a value that has been entered to the processor via a user interface. By way of example, the minimum safe value of haemoglobin oxygen saturation may be about 90%, may be 90%, between about 88% and about 90%, may be between 88% and 90%, or may be any suitable value as entered by a clinician or as determined from a look up table based on one or more patient characteristics such as:

disease (for example chronic obstructive pulmonary disease, emphysema, asthma etc.);
   age;
   height;
   weight;
   BMI (Body Mass Index) or BMI distribution;
   body shape or BSI (Body Shape Index);
   cardiac output;
   pregnancy status;
   difficult airway type;
   treatment history (e.g., type and/or amount of drugs administered to a patient); and
   clinical history (for example, of acidosis).

The $PaO_2$ and/or $SpO_2$ may then be plotted against time (from the first step). Based on this relationship between the measured $PaO_2$ and/or $SpO_2$, and time, the processor may then determine 606 the time remaining until the determined $PaO_2$ is reached, thereby determining the duration of safe apnoea. That may be achieved by the same method as the carbon dioxide method of the embodiment of FIGS. 4 and 5.

Additionally or alternatively, the method comprises determining the time remaining until the determined $PaO_2$ value is reached, based on a rate of change of $PaO_2$.

While the method is described with reference to forming curves, fitting a sigmoidal shape to the points, and plotting $PaO_2$ against time, it will be appreciated by a skilled person that actual curves, shape, and plots will not necessarily be provided, and the processor 108 may perform the method using suitable calculations and/or steps. However, the curves, shape, and plots are analogous of the process that may be performed by the processor 108.

Figure 7:
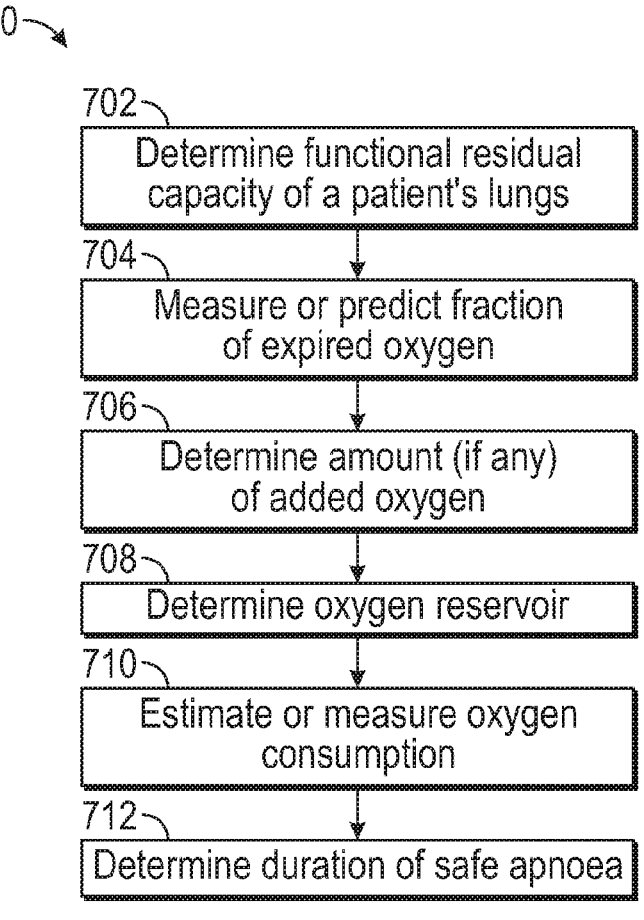
FIG. 7 is a flow chart showing a third embodiment of a method of predicting or determining a duration of safe apnoea.

FIG. 7 schematically shows a third embodiment method 700 for predicting or determining a duration of safe apnoea. This method comprises determining a duration of safe apnoea based on a relationship between a patient's oxygen reservoir (for example, the amount of oxygen present in a patient's lungs) and their oxygen consumption.

The rate of oxygen de-saturation is influenced by the balance between the oxygen reservoir in the lungs and consumption, as outlined by the following equation:

$$\text{Time of safe apnoea} \sim \frac{\text{Oxygen reservoir}}{(\text{Oxygen consumption} - \text{Oxygen supplied})}$$

A first step 702 of the method comprises determining the functional capacity of a patient's lungs to determine a maximum oxygen reservoir volume. The step of determining the functional capacity may comprise estimating using one or more of nitrogen washout, helium dilution, body plethysmography, or a look up table. The step of determining the functional capacity may be performed by the processor or otherwise. The look up table may provide indicative functional reservoir values for different types of patients, for example a healthy patient may have a typical volume reservoir of 30 ml/kg and an obese patient may have a typical volume reservoir of 15 ml/kg.

A second step 704 of the method may comprise measuring or predicting the oxygen consumption of a patient. In some embodiments the oxygen consumption of a patient may be based on a volume of expired oxygen ($FeO_2$) or volume of CO2 entering or exiting the patients airway, or in the patient's lungs. The oxygen consumption of a patient and/or the volume of expired oxygen may be influenced by pre-oxygenation level, age, weight, disease state, etc. The step of measuring or predicting may be performed by the processor or otherwise.

In some embodiments, any supplied oxygen may be shut off for a period of time, and the volume of expired or expelled oxygen ($FeO_2$), or expired or expelled carbon dioxide ($CO_2$) can be measured. In other embodiments, such measurements may be taken while oxygen continues to be supplied.

In some embodiments, the volume of expired oxygen ($FeO_2$) may be determined based on a measurement or estimation of metabolic rate of the patient. Additionally or alternatively, the volume of expired oxygen ($FeO_2$) may be determined based on a measurement or estimation of concentration or volume of $CO_2$ (optionally expelled or expired) at or near a patient's airway. Additionally or alternatively, the volume of expired oxygen ($FeO_2$, or expired carbon dioxide ($CO_2$)) may be determined based on a measurement or estimation of a flow sensor in the ventilation circuit. The flow sensor may output a flow signal indicative of a tidal flow of a patient's breathing pattern, optionally said flow signal may include a bias flow or provided flow component. Optionally, the known supplied or provided flow component can then be removed or filtered from the flow signal to provide a filtered flow signal indicative of a tidal flow of a patient's breathing pattern. From the flow signal indicative of a tidal flow of a patient's breathing pattern, the volume or amount of expired or expelled $CO_2$ and/or the volume or amount of expired or expelled oxygen ($FeO_2$) may be determined (optionally utilising the measurement of concentration of expelled or expired carbon dioxide ($CO_2$) at or near a patient's airway, and/or expelled or expired oxygen ($FeO_2$).

If any oxygen has been provided to the patient by the respiratory therapy system 100, a third step 706 may comprise determining the amount of additional oxygen provided to the patient and/or provided to the patient's lungs by the respiratory therapy system.

The processor 108 may then determine 708 the patient's oxygen reservoir based on the maximum oxygen reservoir volume, less the volume of expired oxygen, plus the amount of oxygen provided to the patient by the respiratory therapy system, if any.

The processor 108 may determine 710 the patient's oxygen consumption. This may be estimated based on the patient's weight ($=10\times\text{Weight}^{3/4}$), may be measured, or may be determined using any other suitable method. It will be appreciated that this step may be carried out before, during, or after the other steps 702-708.

The processor may determine 712 the duration of safe apnoea based on the patient's determined oxygen reservoir divided by the patient's oxygen consumption.

Figure 8:
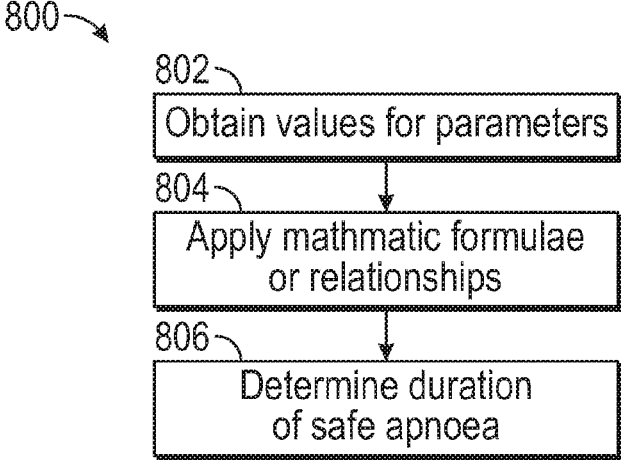
FIG. 8 is a flow chart showing a fourth embodiment of a method of predicting or determining a duration of safe apnoea.

FIG. 8 schematically shows a fourth embodiment method 800 for predicting or determining a duration of safe apnoea. This method comprises determining a duration of safe apnoea based on one or more parameters relating to pre-oxygenation of a patient. The parameter(s) is/are indicative of the effort (i.e. ease or difficulty) to pre-oxygenate the patient to a desired level.

The parameter(s) may comprise one or more of:

i. the ratio of fraction of oxygen in expired air to the fraction of inspired oxygen $$\frac{F_eO_2}{F_iO_2}$$

ii. the ratio of haemoglobin oxygen saturation and fraction of inspired oxygen $$\frac{S_pO_2}{F_iO_2}$$

iii. the P/F ratio which is the ratio of arterial partial pressure of oxygen and fraction of inspired oxygen $$\frac{P_aO_2}{F_iO_2}$$

iv. the ratio of peripheral venous oxygenation and peripheral arterial oxygenation $$\frac{P_vO_2}{P_aO_2}$$

v. the time required to pre-oxygenate the patient
vi. the patient's metabolic rate.
vii. the rate of rise of $PaO_2$ If $FeO_2$ observed during the pre-oxygenation process reaches a predetermined level quickly, this may suggest that there is V/Q mismatch. For example, if the $FeO_2$ increases, and the $SpO_2$ or $PaO_2$ does not increase, or does not increase at a corresponding rate, this suggests that oxygen is going into the lungs well, but not getting into the blood well, and could be an indicator that the patient will desaturate more quickly during an apnoeic event than an average healthy patient, and indicates that a shorter safe apnoea time is more suitable for that patient.

If $PaO_2$ indicates that it is easy to pre-oxygenate the patient (i.e. it rises well and quickly during pre-oxygenation), then this suggests a slow desaturation during an apnoea event because a lot of alveoli are open and good gas exchange is occurring, and therefore a longer safe apnoea time may be appropriate for that patient.

In a first step 802 of the method, values are obtained for the parameters that will be used. The values may be obtained by suitable measurement and/or estimation techniques, and may be obtained by the processor or otherwise.

In a second step 804 of the method, the processor applies one or more mathematical formulae or relationships or algorithms to determining the duration of safe apnoea.

Any of the above methods may be performed or calculated by the processor, or alternatively could be determined on a remote server and then sent to the processor to execute.

In any of the above methods, during respiratory therapy of a patient, the processor 108 may be configured to generate an alert based on the determined duration of safe apnoea. The alert may be a visual alert such as a warning light or a warning on a display unit, an audible alert such as an audible alarm, or a tactile alert such as a vibrating alert. Alternatively, the alert may be a combination of any of the above. The processor may generate the alert substantially at the end of the duration of safe apnoea, or at a specified time before the duration of safe apnoea, such as 10-15 seconds for example. The generation of the alert(s) will alert an anaesthetist to the end of the safe apnoea period, to enable them to supply additional oxygen to the patient or induce breathing assistance to the patient.

In addition or alternatively, the processor 108 may be configured to supply additional oxygen to the patient or induce breathing assistance to the patient, based on the determined duration of safe apnoea. Again, that may occur substantially at the end of the duration of safe apnoea, or at a specified time before the duration of safe apnoea, such as 10-15 seconds for example. For example, the processor may be configured to cause oxygen to be delivered through one of the patient interfaces of the respiratory support system.

Predicting and Using Respiratory Equilibrium in Making Safe Apnoea Determinations Certain aspects described herein can predict a patient's apnoeic respiratory equilibrium which can provide an anaesthetist or other clinician with information to tailor treatment for enhanced safety. For example, systems and methods according to certain aspects use predicted apnoeic respiratory equilibrium to aid in determining a duration of safe apnoea and/or related calculations. The term "respiratory equilibrium" as used herein can refer to a level of saturation at which equilibrium is achieved, and is therefore used interchangeably with the term "saturation equilibrium".

Individuals having normal characteristics such as normal body mass index (BMI) or body shape (BSI) usually exhibit a gradual desaturation profile upon induction of apnoea (see for example FIG. 6B). The rate of desaturation will depend on whether the patient is receiving high flow therapy. Normal individuals may expect to experience a respiratory equilibrium above 95% SpO2. A normal BMI individual receiving high flow therapy may have a very gradual desaturation profile or may have a profile which shows negligible desaturation. A normal BMI patient may be able to for example stay at above 95% $SpO_2$ for a long period of time.

Interestingly, certain patients, such as those having a high body mass index (BMI) (e.g., patients having a BMI equal to or greater than 25, 30, 35, 40, 45, 50 or more), another identified body morphology, compromised lung function, or respiratory disease, may initially de-saturate at the induction of apnoea, to a level where they substantially equilibriate at. This level could be below 90% or below about 88-90% $SpO_2$. For instance, the system 100 can predict and/or detect upon induction of apnoea, that a high BMI patient is likely to stop de-saturating at some level below about 90% saturation and stabilise at a new safe equilibrium level (e.g., about 80% $SpO_2$). The system 100 could also predict and/or detect if a high BMI patient is likely to stop de-saturating at some level below about 90% saturation and equilibrate at a dangerous level (e.g., below 50% $SpO_2$). The information on the latter situation would impact an anaesthetist's handling of the patient's respiratory support during a medical procedure.

Where a patient such as a high BMI patient is likely to reach respiratory equilibrium at a safe level, systems and methods described herein can calculate a likely respiratory equilibrium and provide such information to the clinician, who can decide for example, to continue an intubation process or other procedure instead of stopping to re-administer oxygen.

On the other hand, if the system predicts based on the patient's body morphology that the patient is likely to stabilise at a likely unsafe level (e.g., 70% or 30% $SpO_2$), then the anaesthetist can use this information to choose to intervene immediately during a significant desaturation event.

According to certain aspects, systems described herein can also use the equilibrium to determine, or assist anaesthetists in determining, a duration of safe apnoea. For instance, if the system 100 predicts that the patient will equilibrate at a potential level below a 'normal' threshold saturation level (e.g., equilibriate at 85% $SpO_2$) and if this level is allowed to be reached during a medical procedure, an anaesthetist may choose to intervene and stop any attempt at intubation or other procedure (if the patient is not already intubated) and start re-oxygenating the patient to a desired saturation level, after a relatively short period of time (e.g., 5 minutes), even if the patient is capable of remaining stable at that lower than normal level for a considerable amount of time. Alternatively, the anaesthetist may choose to stop and attempt at intubation or other procedure (if the patient is not already intubated) and start re-oxygenating the patient to a desired saturated level, before that lower than normal level is reached. On the other hand, if the system 100 predicts that the patient will equilibrate at a level above a 'normal' threshold saturation level (e.g., at or above 92%), the anaesthetist may choose to intervene after a longer period of time or may choose to continue the intubation or other procedure until completion.

According to certain aspects, the term "equilibrium" as used herein can mean the level at which things (certain chosen parameters) are stable and not changing (or are changing within acceptable limits or where the rate of change is substantially reduced/changed). For instance, during equilibrium there can be substantial homeostasis in chosen parameters. A respiratory equilibrium may or may not include the act of breathing. In preferred embodiments, it refers to a state in which a patient is not spontaneously breathing. A respiratory equilibrium can mainly include states where there is substantially no breathing or insignificant respiratory distress, e.g., an apnoeic state. In preferred embodiments it refers to gases exchange at the lungs and saturation/desaturation of blood gases. Moreover, a patient may be said to "equilibriate" when they reach a respiratory equilibrium.

Patient Respiratory Equilibrium and V/Q Mismatch

Embodiments described herein can predict a patient's respiratory equilibrium (such as an oxygen saturation equilibrium) by measuring or estimating patient properties or parameters. One example of such a property is V/Q mismatch, which may also be referred to herein as shunt.

A patient can begin to desaturate due to a blocked airway or due to collapsed alveoli. Collapsed alveoli or a partial collapse of a lung is referred to as atelectasis. Anaesthesia in a person undergoing surgery generally causes some amount of atelectasis. Collapsing of alveoli by external pressures may be referred to as compression atelectasis. High BMI patients tend to have more collapsed alveoli and a greater degree of compression atelectasis. During atelectasis, the volume of un-collapsed alveoli gradually drops but does not go to zero and eventually plateaus because of structures that hold some of the lungs/alveoli open such as ribs, surfactant, pressure/elasticity of tissue etc. Atelectasis can be reduced by high flow therapy.

If a patient's airway is blocked, the atelectasis and desaturation effect will be different (compared with compression atelectasis) and the patient will proceed along the oxygen dissociation curve at a rate depending on the rate of remaining oxygen consumption which may be rapid. If atelectasis is occurring, then the curve depends on the extent of alveoli collapse and the saturation may equilibrate and stabilise.

In atelectasis, when alveoli are collapsed, blood does not fully oxygenate due to V/Q mismatch. Oxygenation in the lungs does not fully occur as some blood moves from the pulmonary artery to the pulmonary vein without gas exchange—a percentage of this is V/Q mismatch. V/Q mismatch may lead to $CO_2$ accumulating in the blood and/or not enough $O_2$ in the blood. V/Q mismatch can be caused by anything that increases or decreases ventilation or perfusion of the lungs. This may occur due to gravity or due to a certain blood flow pattern or from atelectasis. If the oxygen being delivered to a patient is increased but more oxygen is not appearing in the blood (or a proportional rise in oxygen in the blood is not observed), this indicates there is a V/Q mismatch.

$PaO_2$, for example during apnoea, drops at a rate dependent on how the alveoli are closing so may be used as an indicator of V/Q mismatch. When a patient is lying on their back there is an increase in compression atelectasis and V/Q mismatch due to body weight pushing down on the lungs which can collapse alveoli. Here, V/Q mismatch directly relates to compression atelectasis. In high BMI patients, there may be more compression atelectasis and thus more V/Q mismatch.

As will be described in more detail herein, systems and methods according to certain embodiments measure pre-operative parameters that provide an indication of V/Q mismatch. This estimate of V/Q mismatch (which may be correlated to a patient BMI) can then be used to predict a respiratory equilibrium, preferably an oxygen saturation level. A duration of safe apnoea time can also be determined by the estimate of V/Q mismatch.

At a certain percentage of V/Q mismatch in a person, equilibrium is reached between the lungs pushing out and bodyweight pushing down when a patient is lying horizontally. There is a balancing of forces between the mass pushing down and the internal pressure from the lungs/skeleton/high flow therapy. Using oxygen saturation as an example, in a non-high BMI patient, this equilibrium typically occurs at around 100% oxygen saturation on high flow therapy. In high BMI patients (or patients that meet certain criteria based on determined parameters described herein, such as those with another identified body morphology, compromised lung function, or respiratory disease), the equilibrium may occur at a lower oxygen saturation, e.g. around 85% on high flow therapy.

A clinician will typically stop an intubation or other procedure once a patient drops below a threshold $SpO_2$ level (e.g. 90% as mentioned earlier). In a high BMI patient this stoppage may be before $SpO_2$ reaches the 85% equilibrium and stabilises. Intervention occurs because the non-high BMI patient (with equilibrium at about 100% $SpO_2$) in this example would be heading towards the steep part of the oxygen dissociation curve after 90% $SpO_2$ where saturations can rapidly deteriorate to critical levels (<70%), posing significant risk to the patient as organs, tissues and cells require oxygen to function. The high BMI patient might not rapidly desaturate and they may stabilise at 85%. Therefore, it is useful to have an indication of a respiratory equilibrium where the patient may stabilise so that therapy can be tailored to each patient as best seen fit by the anaesthetist, and not stopped prematurely.

Figures 9, 10:
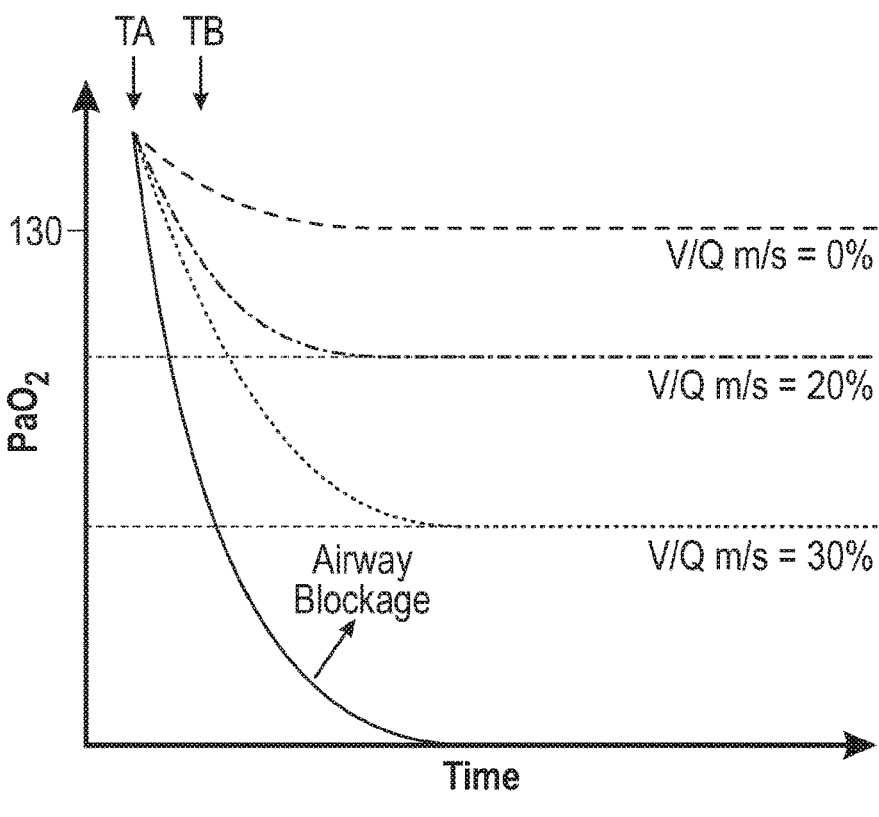
FIG. 9 is an example of a graph showing $PaO_2$ over time for different amounts of V/Q mismatch.
FIG. 10 is a flow chart showing an embodiment of a method of predicting or determining respiratory equilibrium and duration of safe apnoea.

FIG. 9 shows an example of the effect of the degree of V/Q mismatch on oxygen saturation. Different degrees of V/Q mismatch represent different degrees of compression atelectasis which may be a function of BMI (i.e. V/Q mismatch may be correlated to patient BMI). It can be seen that at the shown percentages of V/Q mismatch an equilibrium is reached. This equilibrium is related to compression atelectasis and represents the plateaued volume of un-collapsed ('active') alveoli, as previously described.

In FIG. 9, as V/Q mismatch increases from 0 to 30%, the stable oxygen saturation decreases. This figure shows that if a percentage of V/Q mismatch can be estimated then it can be monitored and extrapolated to a value at which equilibrium will be reached. Using this V/Q mismatch equilibrium estimate and/or other parameters, such as $PaO_2$, a respiratory equilibrium, such as oxygen saturation equilibrium, can be estimated. Calculating the area under these V/Q mismatch curves may also be used to estimate a property associated with a respiratory equilibrium.

FIG. 9 also shows the other situation described above where an airway blockage is occurring and causing oxygen desaturation. It can be seen that when this blockage occurs a rapid drop/discontinuity is seen in $PaO_2/SpO_2$. $PaO_2$ or another parameter may be monitored during a procedure and if a rapid drop like this is detected, there can be an alert that the cause of desaturation is likely to be a blocked airway.

Predicting and Utilizing Respiratory Equilibrium

FIG. 10 is a flow chart schematically showing an embodiment of a method 1000 of predicting or determining respiratory equilibrium, and using the predicted value equilibrium in the course of monitoring and treating a patient.

At step 1002, one or more physiological parameters of the patient are measured. The measurements can occur before an operation (e.g., before administering anaesthetic, before intubation, etc.), during an operation (e.g., after administering anaesthetic, during intubation), or both.

For example, a variety of physical measurements can be taken pre-operatively. Such measurements can be used to determine characteristics indicative of respiratory equilibrium. For instance, such measurements can provide an indication of the patient's BMI, BMI distribution, or body shape index (BSI), or other body morphology indicators. These and other measurements can be correlated to and used to determine compression atelectasis and related V/Q mismatch, which can indicate respiratory equilibrium. In order to determine BMI, BSI or other body morphology indications, a variety of measurements could be used, including without limitation:

weight;
  height;
  neck circumference;
  patient waist circumference; and
  hip to waist ratio.

Such measurements can be entered into the system (e.g., into the memory 134 of the system 100 of FIG. 3A). For instance, the clinician may manually enter them into the system using a keypad or touch screen of the I/O module 110 after measuring them or reading them from patient notes. Or the measurements may be taken using electronic scales or other electronic measurement instruments, and communicated wired or wirelessly to the system 100.

The system 100 can calculate BMI, BSI, or other body morphology indication using a combination of one or more of any of the parameters listed above, or other appropriate parameters. For instance, the system 100 can use a combination of one or more of any of the above listed parameters to determine BMI. The system 100 can use the hip to waist ration to determine BMI distribution. As another example, the system 100 can use one or more of the patient's waist circumference, height and BMI to calculate BSI.

A variety of other pre-operative physical measurements/indicators can be measured and/or input into the system 100 at step 1002, such as:

A sickness level or a Ramsay score.

Age, pregnancy status, patient clinical history (for example, acidosis), treatment history (e.g., type and/or amount of drugs administered to a patient). For example, older patients may have less lung volume, and pregnant patients can have less lung volume and/or consume more oxygen than patients who are not pregnant.

Difficult airway type/patency, which the system may be determine by delivering trace gases to a patient (e.g., via the patient interface 200 or mask 300) and measuring resulting changes (e.g., via the sensor 120). Some examples of techniques for determining airway patency that can be incorporated into the systems and methods described herein are referred to in PCT Application Number PCT/IB2017/052458 (published as WO/2017/187391), entitled "System for Determining Airway Patency", which is incorporated in its entirety by reference herein.

Gas/therapy flow characteristics such as velocity and pressure.

A variety of the patient's physiological parameters can also be measured before administering anaesthetic, and can be used by the system 100 in combination with or instead of any of the previously monitored physiological parameters to predict respiratory equilibrium.

One such physiological parameter is V/Q mismatch (e.g., percentage of V/Q mismatch), which as discussed may be a proxy for or represent BMI or represent the correlation of BMI with another parameter. Because V/Q mismatch can be correlated to physiological parameters such as BMI, BSI, etc., the system 100 in some embodiments determines V/Q mismatch indirectly using BMI or other physiological parameters/measurements.

However, in other embodiments, V/Q mismatch can be determined by other physiological measurements. For instance, V/Q mismatch may be determined with measurements taken using an electrical impedance tomography belt, MRI imaging, or by increasing patient $O_2$ ($FiO_2$) (e.g., using high flow administered by the patient interface 200) and observing $PaO_2$ change. The physiological sensor module 121 can include appropriate componentry for making such measurements.

In some embodiments, the system 100 can be used to monitor blood gases such as $PaO_2$ or $SpO_2$ to give an indication of V/Q mismatch. For instance, the physiological sensor module 121 can include a pulse oximeter that can be used to monitor $PaO_2$ (or monitor a $PaO_2$ proxy, infer $PaO_2$, or derive $PaO_2$) and/or $SpO_2$ when a patient moves between various positions e.g. from standing or sitting up to lying down, etc. The clinician could change the oxygen percentage delivered using the flow generator 102 while the patient is in the different positions and compare the $PaO_2$ and/or SpO$_2$ responses over time between the different positions to determine V/Q mismatch. For example, a percentage of V/Q mismatch may represent BMI or the correlation of BMI with another parameter.

A number of other physiological parameters can be measured by the sensor module system 100, including without limitation:

Cardiac output: For example the physiological sensor module 121 may include an electrocardiograph (ECG), pulse oximeter, 2D/3D echocardiograph, or other device that can measure the stroke volume and how fast the heart is beating, which can be an indicators of a patient's oxygenation. For instance, a faster beating heart and larger cardiogenic oscillations (larger stroke volume) can indicate more CO$_2$ clearance and more inspired oxygen, while a slower beating heart and smaller oscillations can indicate less CO$_2$ clearance and less inspired oxygen. Changes in amplitudes of cardiogenic oscillations over time, which can impact CO$_2$ clearance and therefore PaCO$_2$ progression and blood pH, which in turn affects O$_2$ progression levels.

Blood pressure: The physiological sensor module 121 may include a blood pressure monitor.

PaO$_2$ or PaCO$_2$; CO$_2$ or O$_2$ saturation levels; transcutaneous CO$_2$ or O$_2$. Metabolic rate (CO$_2$ production and clearance). The physiological sensor module 121 can include a capnograph, pulse oximeter, or other appropriate device for measuring these parameters. Arterial oxygen content may be determined as well. Measuring PaO$_2$ (or transcutaneous O$_2$, which can provides a measure of arterial O$_2$) can be useful in predicting desaturation because it can indicate a decreased oxygen level in the blood. PaCO$_2$ (or transcutaneous CO$_2$ which also provides a measure of arterial CO$_2$) gives an indication of when the CO$_2$ has reached an unacceptably high level. In both cases the rate of change of can be useful to show when the value crosses a 'safe' limit. In addition, the capnograph according to certain embodiments can be used to measure CO$_2$ coming out of the mouth and can therefore provide an indication as to whether the airway is patent, how much CO$_2$ is coming out (and by inference how much O$_2$ is going in), and/or the rate of consumption of O$_2$. The pulse oximeter can be used, for example, to measure when saturation drops below a safe level, e.g., by looking at the rate of change (e.g., of the SpO$_2$).

Blood gases may be estimated using a pulse oximeter. The physiological sensor module 121 can also include non-invasive electrodes or infrared spectroscope for taking blood gas measurements.

Lung volume: The physiological sensor module 121 can include a spirometer to measure the volume of inspired/expired air. For instance, the Helium dilution technique may be employed in some embodiments. Alternatively, CT scans, electrical impedance tomography (EIT) or lung plethysmography may be used to take such measurements. For example, greater lung volume can indicate more oxygen and therefore a longer time to desaturation.

Lung compliance: This can also be calculated from measurements taken using a spirometer. For example, lung compliance can relate the pressure being applied to the lungs and the resulting volume increase that it causes. Thus, if the system 100 can monitor pressure and compliance it can determine lung volume.

Response to 100% delivered O$_2$: The physiological sensor module 121 can measure parameters such as PaO$_2$ and/or stroke volume before and after 100% oxygen is administered to the patient through the cannula 200.

Fluctuations in flow and/or inspired/expelled CO$_2$/O$_2$ (FiO$_2$/FeO$_2$ or FiCO$_2$/FeCO$_2$): The physiological sensor module 121 can include a mouth-based flow meter and/or CO$_2$ meter to make such measurements. The system 100 can also determine PaO$_2$/FiO$_2$ (or similar) ratio.

Ratio of PaO$_2$ (or another suitable physiological indicator) and BMI (or another physical characteristic indicative of BMI, such as neck circumference and/or hip to waist ratio).

Airway resistance: The physiological sensor module 121 can include a whole plethysmography device to measure airway resistance, such as by using the forced oscillation technique or the interrupter technique.

Lung/airway pressure: The physiological sensor module 121 can include a common pressure sensor to measure this.

Opening of alveoli: The physiological sensor module 121 can include an acoustic sensor to make such measurements, which provides an indication of shunt.

Patient Temperature and 2,3-diphosphoglyceric acid concentration in the blood.

In addition to (or instead of) using pre-operative physical and measurements to predict respiratory equilibrium, the system 100 can also utilize measurements of one or more physiological parameters taken after initiation of the medical procedure/operation. As an example, following administration of anaesthetic using the second respiratory system 312, the system may measure PaO$_2$ or SpO$_2$ using the physiological sensor module 121.

At step 1004 the system 100 then uses the parameters measured at step 1002 to predict respiratory equilibrium, duration of safe apnoea, or other related parameters. In general, the system 100 can use any combination of the measured physical or physiological characteristics to estimate the expected level respiratory equilibrium, duration of safe apnoea, duration of safe respiratory equilibrium, time until the expected level of respiratory equilibrium is reached, rate of increase/decline of a respiratory parameter (e.g. a rate of decline of PaO$_2$), etc. The system can make such calculations in any appropriate manner, such as via lookup tables by comparing or fitting the measured parameters with empirically obtained data or models, or via computationally processing using the measured parameters as inputs. In some embodiments, the system 100 can employ one or more of the methods of FIGS. 15A-15C to predict or determine respiratory equilibrium or duration of safe apnoea, such as where the predicted PaCO$_2$ level progression (FIG. 15A) or predicted O$_2$ level progression (FIGS. 15A-15C) are used to predict respiratory equilibrium or duration of safe apnoea.

At step 1006 the system 100 provides information to the clinician based on the respiratory equilibrium prediction or other parameter determined at step 1004. Such information can be provided via the input/output interface 110 of the system 100, or some other appropriate mechanism. For instance, the system 100 can notify the clinician by presenting on a display one or more of a predicted respiratory equilibrium value (e.g., 70% O$_2$, 85% O$_2$, 90% O$_2$, etc.), a predicted duration of safe respiratory equilibrium, a predicted duration of safe apnoea, or another predicted parameter.

At step 1008 the system 100 monitors the patient during the medical procedure and refines the predictions based on the monitoring, and/or performs real time monitoring of the equilibrium. For instance, the system 100 can monitor one or more of $PaO_2$, $SPO_2$, $CO_2$, or the like and use the monitored values to evaluate in real time the accuracy of the predicted values, and update the information provided to the clinician as appropriate. For instance, if the predicted respiratory equilibrium is 85% $O_2$ but the system 100 determines via $PaO_2$ monitoring during the intubation procedure that monitored $PaO_2$ indicates an airway blockage, the system 100 may output an audible or visual alarm via the I/O interface 110 (e.g., speaker, flashing LED, graphics on a display, etc.) that shows an airway blockage is the cause for the desaturation to prompt the clinician to stop intubation or otherwise intervene as appropriate. For example, where the system employs one or more of the methods of FIG. 15A-15C to predict respiratory equilibrium or duration of safe apnoea at step 1004, the system 100 can update and refine the simulated $CO_2$ or $O_2$ level progressions (e.g., $PaCO_2$ or $SpO_2$ level progressions) using patient monitoring or other measured data, and use the updated progressions or other updates to refine the respiratory equilibrium or safe apnoea determinations.

At step 1010 the system 100 in some embodiments can control one or more other devices in the patient environment 305 using the predicted respiratory equilibrium or other predicted or measured values. For instance, the system 100 in one implementation predicts a respiratory equilibrium value of 85%, and increases gas flow to the patient interface 200 by controlling the flow generator 102, e.g., in order to affect the patient's blood oxygen content and thereby increase the respiratory equilibrium value to a higher value such as 86% or 87% and/or the lengthen the duration of safe equilibrium (e.g., from 5 minutes to 10 minutes). Duration of safe equilibrium may be an estimated duration of time that a patient can be allowed to remain at the equilibrium level. This could be a pre-set duration or a duration set by a user.

Example Scenarios for Typical and Atypical Patients

Illustrative examples will now be described in conjunction with FIGS. 10 and 11A-11D. FIGS. 11A-11D are examples of graphs showing profiles of the change in $PaO_2$ and $SpO_2$ over time.

Figure 11A:
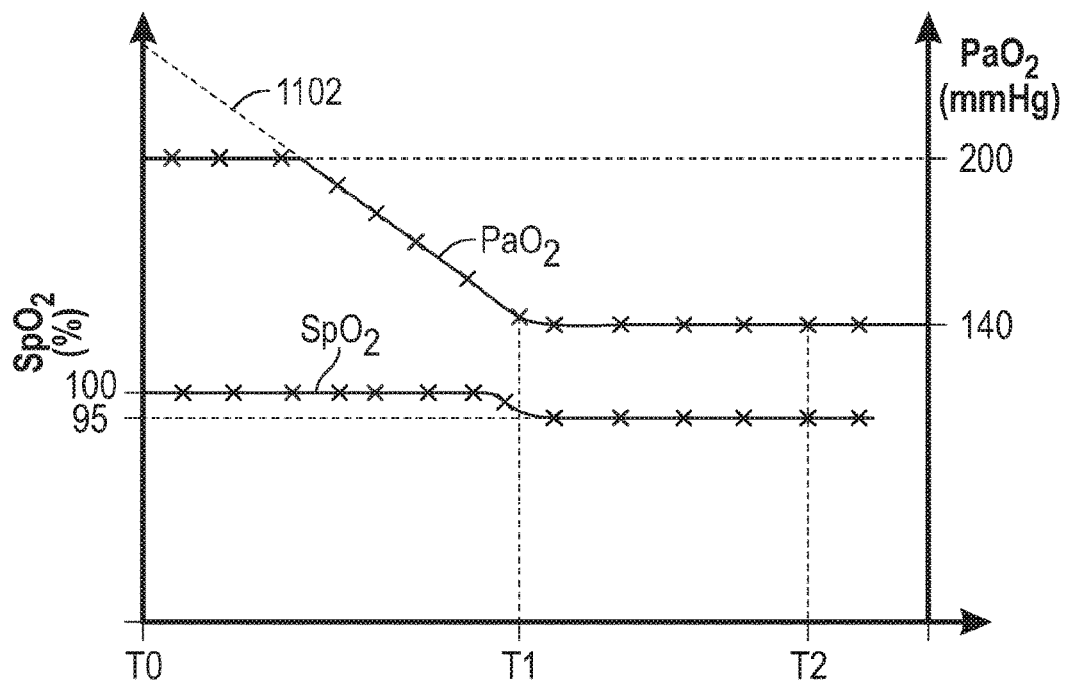
FIGS. 11A-11D are examples of graphs showing the change in $PaO_2$ and $SpO_2$ over time for various patients/individuals.

FIG. 11A shows an example of a profile for a typical patient/individual, such as a normal, non-high BMI patient, where the patient equilibrates at what would ordinarily be considered an acceptable saturation level of between about 95-100%.

Figure 11B:
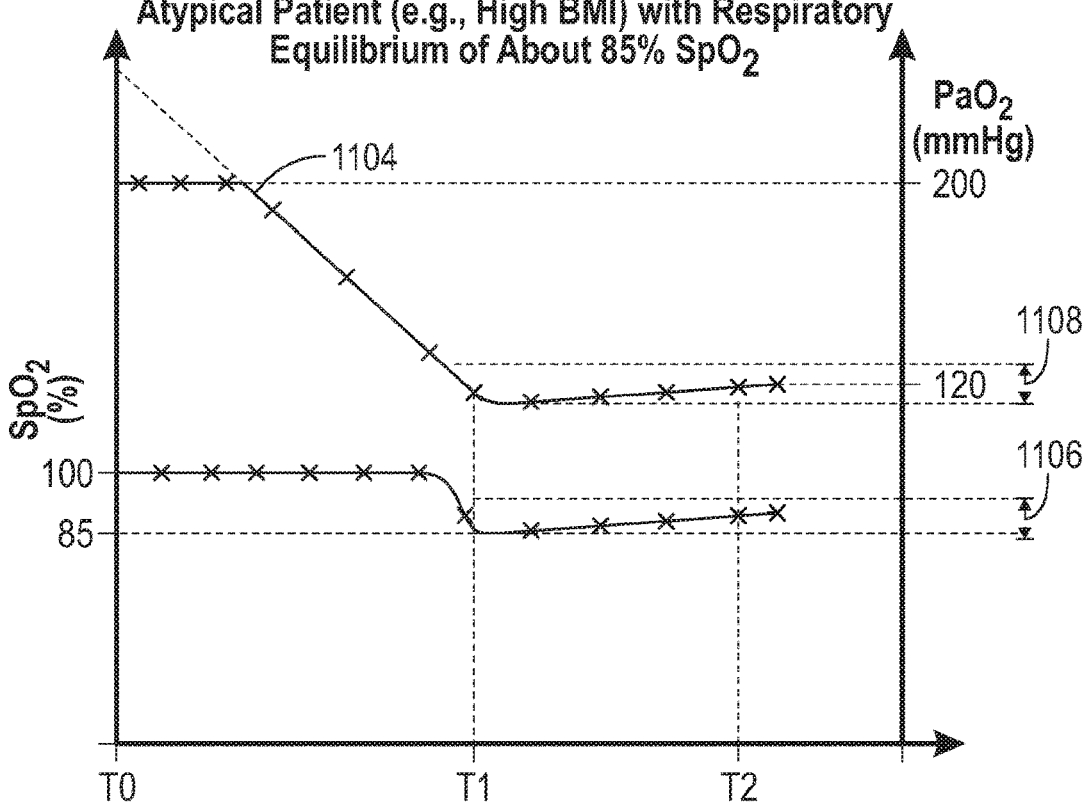

FIG. 11B shows an example of a profile for an atypical patient/individual, such as high BMI patient, where the patient equilibrates at about 85%, which may be considered an acceptable saturation level, but which is below a SpO2 and/or PaO2 threshold for a typical (e.g., non-high BMI) patient.

Figure 11C:
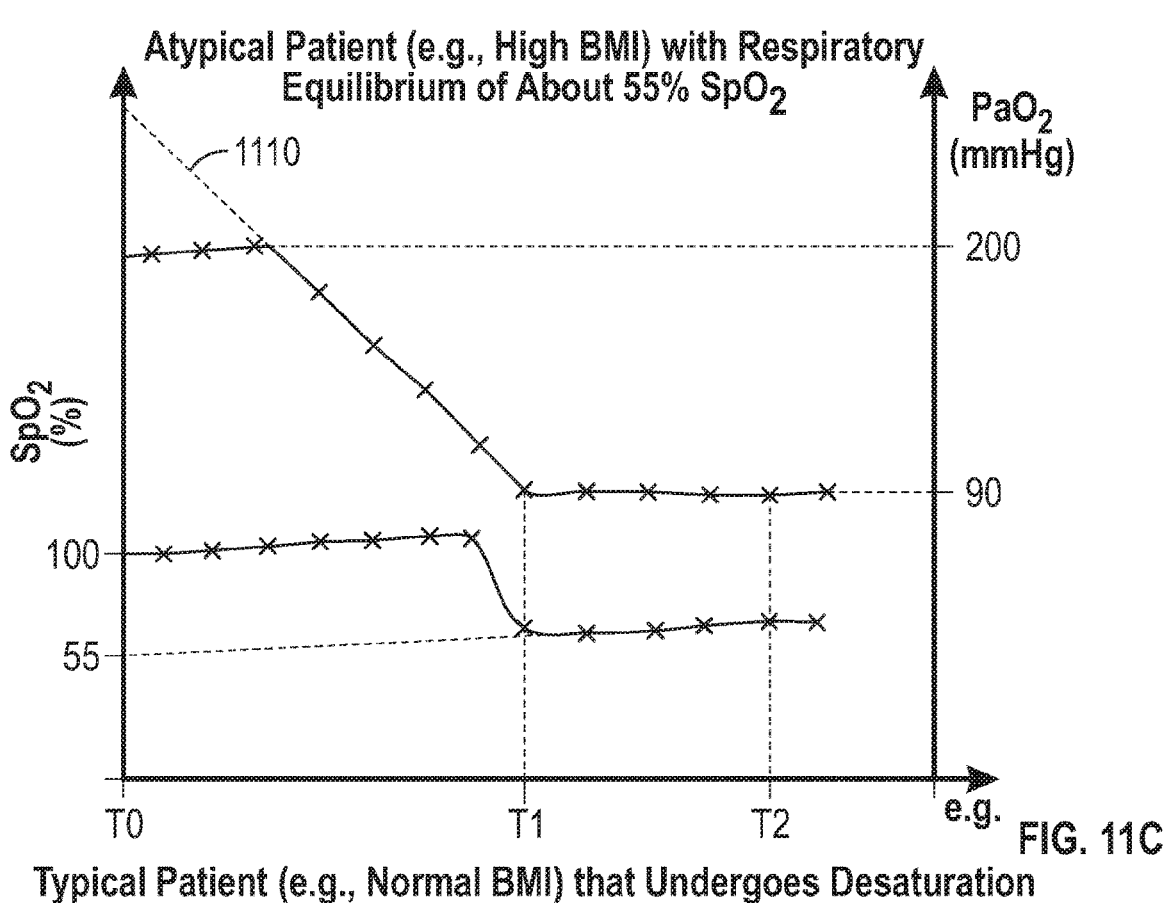

FIG. 11C shows an example of a profile for an atypical patient/individual, such as high BMI patient, where the patient equilibrates at what would ordinarily be considered an unacceptable safe saturation level of about 55%.

Figure 11D:
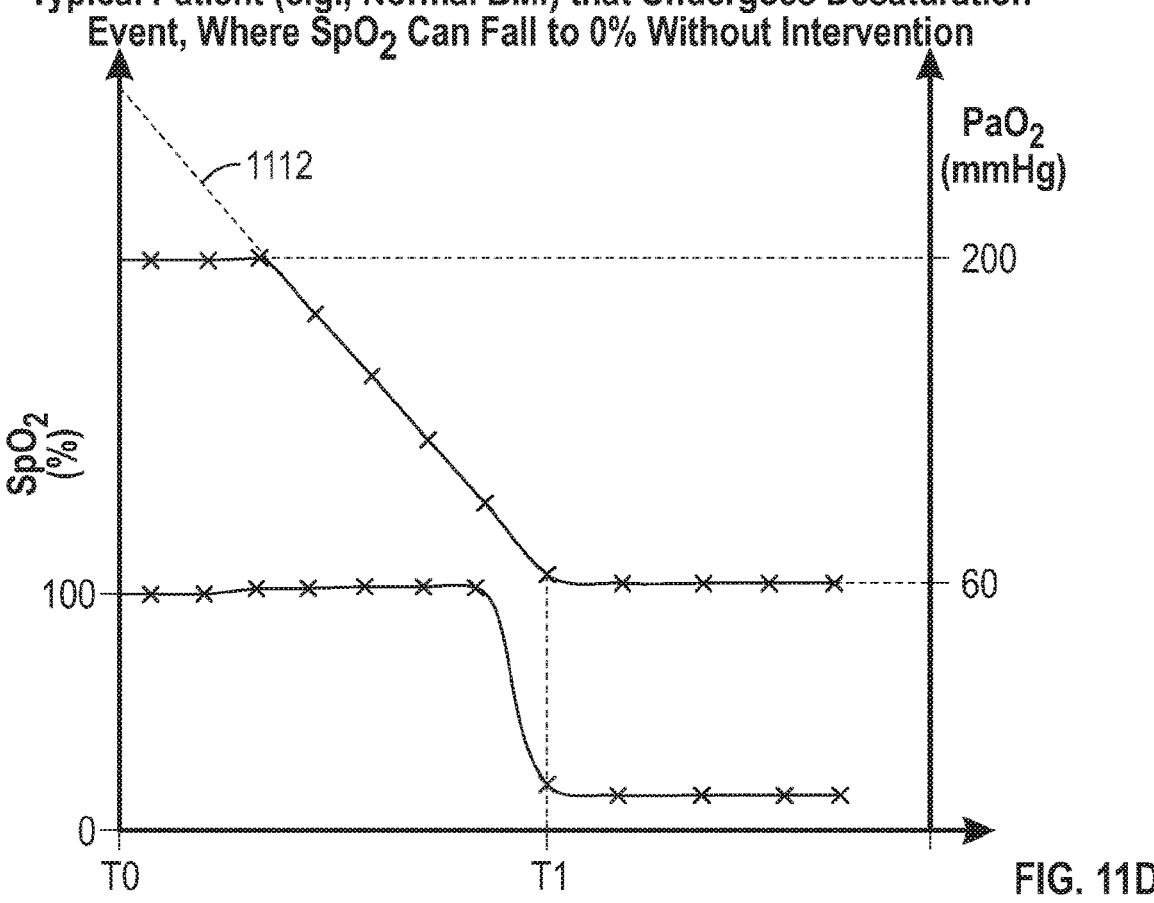

FIG. 11D shows an example of a profile for a typical patient/individual (e.g., a normal, non-high BMI patient), where the patient undergoes a desaturation event, such as an obstructed airway.

Referring first to FIGS. 11A-11B, for both a first patient (e.g., normal BMI, FIG. 11A) and second patient (e.g., high BMI, FIG. 11B) patient the clinician at step 1002 measures a neck circumference and weight prior to an intubation procedure. The clinician inputs the values into the system 100 using a keyboard of the I/O interface 110.

For both the first and second patients the system 100 at step 1004 calculates the patient's BMI. The system 100 stores in the memory 134 a database including a number of oxygen respiratory equilibrium profiles each corresponding to different BMI values or ranges of BMI values. The system 100 consults the database to select a matching predicted respiratory equilibrium profile for the patient corresponding to the calculated BMI. For the non-high BMI patient (FIG. 11A) the matching equilibrium profile indicates a respiratory equilibrium value of between about 95-100% and a duration of safe equilibrium of 10 minutes. For the high BMI patient (FIG. 11B) the matching equilibrium profile indicates a respiratory equilibrium value of 85% and a duration of safe equilibrium of 8 minutes.

The system 100 can also determine a duration of safe apnoea. For example, for the first patient (FIG. 11A), a 90% $SpO_2$ value is the desaturation threshold. As shown, the non-high BMI patient has an initial $SpO_2$ of about 100%, and an initial $PaO_2$ of about 200 mmHg. Once the apnoea event begins the patient's $PaO_2$ decreases as oxygen is consumed but not replaced. Even though $PaO_2$ is decreasing no corresponding decrease in $SpO_2$ is initially observed. For this patient, once a significant decrease of $SpO_2$ is observed it may be too late to act because the patient can desaturate rapidly.

Thus, the system 100 can predict the safe apnoea time for the non-high BMI patient based on a threshold arterial partial pressure of oxygen ($PaO_2$). This threshold $PaO_2$ may be determined from a threshold haemoglobin oxygen saturation ($SpO_2$) as described above, and as shown in FIG. 6A. For the first patient, the threshold PaO2 value is a value less than 140 mmHg $PaO_2$ because, as shown in FIG. 11A, the patient is expected to equilibriate at what is normally a safe saturation value of 95-100% at a corresponding PaO2 value of 140 mmHg. For example, the threshold saturation amount for the first patient may be 90% $SpO_2$, which corresponds to a threshold $PaO_2$ value of about 60 mmHg. Because the system 100 has determined that the patient is expected to equilibriate at a safe level between 95-100%, the system 100 in one embodiment can utilize the respiratory equilibrium and duration of safe equilibrium predictions (which could be impacted by factors affecting the patient during the medical procedure, e.g. planned administration of medication at certain time points, changes in patient position at certain time points, etc.) to determine the duration of safe apnoea. In particular, the system 100 may predict that the patient will equilibrate to the 95-100% $SpO_2$ level after 2 minutes, and therefore predict or determine that the duration of safe apnoea is 12 minutes (2 minutes predicted time to equilibrium plus 10 minutes predicted duration of safe equilibrium).

On the other hand, FIG. 11B shows a corresponding plot for the atypical, high BMI patient. A respiratory equilibrium can be seen to be occurring at about 85% $SpO_2$ due to compression atelectasis, as predicted. Although the 85% equilibrium number is lower than the threshold for typical patients, the system 100 may determine that the 85% $O_2$ predicted respiratory equilibrium value for the high-BMI patient is a potentially acceptable level based on the determination that the patient is a high-BMI patient. Thus, the system 100 utilizes the respiratory equilibrium and duration of safe equilibrium predictions to determine the duration of safe apnoea. In particular, the system 100 may predict that the patient will equilibrate to the 85% $SpO_2$ level after 2 minutes, and therefore predict that the duration of safe apnoea is 10 minutes (2 minutes predicted to equilibrium plus 8 minutes predicted duration of safe equilibrium). FIG. 11C shows that for a second atypical patient (e.g., a second high BMI patient), the system 100 predicts an equilibrium value of about 55%, which may be below what would be considered an acceptable level. As just one example, this patient may be high BMI and also have a respiratory disease or some other type of compromised lung function, resulting in the lower equilibrium prediction than the patient of FIG. 11B.

In the procedures for both of the two patients, at step 1006 the system 100 displays the respiratory equilibrium and duration of safe apnoea values on a display of the I/O interface 110. The clinician reviews the information and begins to administer anaesthetic while the patient is monitored by a pulse oximeter of the physiological sensor module 121.

Returning to step 1004, the system 100 according to the illustrative implementation uses physiological measurements to confirm the initial respiratory equilibrium predictions and safe apnoea determinations. In particular, the system 100 compares $PaO_2$ measurements (or $PaO_2$ proxy measurements) taken using the physiological sensor module 121 prior to administration of anaesthetic (e.g., TA in FIG. 9) to values measured as the anaesthetic drug begins to take effect (e.g., TB in FIG. 9). The system 100 uses the measured values to predict or determine a projected $PaO_2$ profile over the course of the procedure. The system 100 can determine the patient's V/Q mismatch and/or change in V/Q mismatch using such measurements because the change in $PaO_2$ from a non-paralyzed to paralyzed state is reflective of the level of compression atelectasis and how quickly oxygen is being consumed. The system 100 uses the projected $PaO_2$ profile to consult a stored database (in the memory 134) that includes a set of empirically obtained $PaO_2$ profiles corresponding to different levels of V/Q mismatch. The database returns a level of V/Q mismatch for the patient corresponding to the projected $PaO_2$ mismatch. For example, in a first example scenario, based on the V/Q mismatch calculated in the procedures for both the high BMI patient (FIG. 11B) and the non-high BMI patient (FIG. 11A), the system 100 determines that the initially predicted respiratory equilibriums (85% and 95-100% respectively) and durations of safe apnoea predictions (10 minutes and 12 minutes respectively) continue to be correct.

When the patient is fully anaesthetized the clinician begins the intubation procedure. At step 1008, the system 100 continues to monitor the patient using a pulse oximeter of the physiological sensor module 121. The system 100 monitors $PaO_2$ (or a proxy for $PaO_2$) with the pulse oximeter. For example, during the intubation or surgical procedure, such physiological parameters can continue to be monitored continuously or at set intervals.

At step 1008 and referring again to FIG. 11A, as the non-high BMI patient is monitored, the system 100 may monitor the slope 1102 of the $PaO_2$ change from time T0 to time T1 and, if the slope 1102 indicates that the threshold $PaO_2$ and/or $SpO_2$ level (e.g., 60 mmHg/90% $SpO_2$ level) will be reached prior to the original 12 minute duration of safe apnoea prediction, the system 100 updates the predicted duration of safe apnoea accordingly and informs the user, e.g., change the value displayed on the I/O interface 110, issue an audible alarm, or the like. For example, referring to FIG. 11D, the system 100 in one example scenario may detect an unexpectedly steep downwards $PaO_2$ slope 1112, which indicates that a desaturation event (e.g., due to a blocked airway) will occur if there is no intervention by the clinician, and the system 100 may output an alarm or otherwise notify the clinician. In such a case, the duration of safe apnoea is based on, or may be equal to, a predicted length of time until the arterial partial pressure of oxygen reaches (or optionally goes below) a threshold $PaO_2$ value, which corresponds to a threshold $SPO_2$ (e.g., 90%). The length of time until the $PaO_2$ reaches the threshold $PaO_2$ may be determined by measuring or estimating a rate of change of $PaO_2$. For example, in FIG. 11D at time T1 the $PaO_2$ is approximately 60 mmHg, which corresponds to a haemoglobin oxygen saturation ($SpO_2$) approaching 0%. Thus, the threshold $PaO_2$ value in the illustrated example would be some value above 60 mmHg (e.g., 80 or 90 mmHg).

On the other hand, if the readings conform to the predictions, the system 100 may continue to display the originally predicted duration of safe apnoea of 12 minutes.

With respect to the high BMI patient, referring to FIG. 11B, the system 100 may similarly monitor the $PaO_2$ readings, and if the slope 1104 indicates that the actual equilibrium value is likely to be lower than the originally predicted 85% $SpO_2$ value. In such a case, the system 100 can update the display to inform the user of a new equilibrium and/or duration of safe apnoea value, issue an audible alarm, or the like. On the other hand, if the system 100 determines (e.g., by monitoring the slope 1104 of the $PaO_2$) that the patient is on track to reach $SpO_2$ equilibrium at the predicted value of 85%, the system 100 may continue to display the originally predicted equilibrium value and duration of safe apnoea of 10 minutes.

Moreover, when compression atelectasis occurs in the high BMI patient and the respiratory equilibrium is observed, there is also an equilibrium in $PaO_2$. These parameters may then remain in equilibrium until a desaturation due to, for example, a blocked airway. The system 100 can continue to monitor the $PaO_2$ and $SpO_2$ to confirm that they are remaining in equilibrium as expected. If the system 100 detects a sufficient threshold deviation from the equilibrium value of $SpO_2$ or $PaO_2$, the system 100 can inform the user as appropriate with an audible or visual alarm. Otherwise, if the system 100 detects that the parameters remain in equilibrium, the system 100 may leave the predicted values on the display and the clinician may continue the procedure without intervention until the end of the duration of safe apnoea at T2, at which time the system 100 may notify the user, again via a visual or audible notification.

Referring again to FIG. 11B, in some embodiments, the system 100 monitors whether the patient's respiratory equilibrium stays within an envelope 1106 defined by an upper threshold (e.g., 87%) set a certain amount above the 85% predicted $SpO_2$ saturation equilibrium, and a lower threshold (e.g., 83%) set a certain amount below the 85% predicted $SpO_2$ saturation equilibrium. The system 100 can additionally or alternatively monitor whether the $PaO_2$ stays within an envelope 1108 defined by upper an upper threshold (e.g., 125 mmHg) set a certain amount above the 120 mmHg predicted $PaO_2$ equilibrium, and a lower threshold (e.g., 115 mmHg) set a certain amount below the 120 mmHg predicted equilibrium. If the system 100 detects that the $SpO_2$ or $PaO_2$ deviate outside of the envelopes 1106, 1108, the system 100 can notify the user by issuing an alarm, updating the reported equilibrium value on the display, or the like.

As shown, $PaO_2$ generally levels out if there is shunt occurring (e.g., shortly after T1 in FIG. 11B due to compression atelectasis), reduction in metabolic rate (e.g. reduction in oxygen consumption, reduction in carbon dioxide production) and there is a patent airway. Using these PaO2 measurements, the system can determine the value of $PaO_2$ at which the curve will plateau and the time until this will occur (i.e. the expected level of respiratory equilibrium and the time until this expected level is reached, can be estimated), and use this information to adjust the respiratory equilibrium, duration until equilibrium, and/or duration of safe apnoea determinations and inform the user as appropriate.

Any of the other types of physiological monitoring described herein can also be used to assist in the safe apnoea determination. As one example, in some embodiments, the system 100 can use a capnography reading to analyse expired $CO_2$ to detect a likely airway blockage, and issue an alarm accordingly. The system 100 can use the sensor 120 on the patient interface 200 or a separate capnography device to perform such monitoring, for example.

FIG. 12 shows a schematic diagram showing respiratory equilibrium and safe apnoea calculations at different stages 1200, 1210, 1220 of an operation.

The diagram shows a respiratory equilibrium calculator 1202, safe apnoea calculator 1204, output 1206, and controller 1208. The respiratory equilibrium calculator 1202, safe apnoea calculator 1204, and controller 1208 may be modules implemented as firmware or software in the controller 108 of the system 100, for example. The output 1206 may be part of the I/O 110.

At a pre-operative stage 1200 respiratory equilibrium calculator 1202 receives one or more pre-operative measurements and/or other inputs associated with a patient. These can be any appropriate physiological or other parameters such as any of those described herein (e.g., with respect to FIGS. 9-11B) including height, weight, blood oxygen or carbon dioxide related parameters, lung volume, and cardiac output, or any combination thereof, to name a few.

Based on one or more of the received inputs, the respiratory equilibrium calculator 1202 generates an initial equilibrium prediction, and provides it to one or more of the safe apnoea calculator 1204, the output 1206, and the controller 1208. The respiratory equilibrium calculator 1204 can perform the prediction in any of the ways described herein, for example.

The safe apnoea calculator 1204 can receive one or more pre-operative measurements and/or other inputs. These can be any appropriate physiological or other parameters such as any of those described herein including any of the parameters described herein as being useful in determining a duration of safe apnoea, including height, weight, blood oxygen or carbon dioxide related parameters, lung volume, and cardiac output, or any combination thereof.

As shown, the safe apnoea calculator 1204 can also receive the initial respiratory equilibrium prediction from the respiratory equilibrium calculator 1202.

The safe apnoea calculator 1204 generates an initial safe apnoea prediction and provides it to one or both of the output 1206 and the controller 1208. The safe apnoea calculator 1204 can generate the safe apnoea prediction using any combination of one or more of the initial equilibrium prediction and the other pre-operative measurements/inputs. For instance, in one embodiment the safe apnoea calculator 1204 uses solely the initial equilibrium prediction in generating the safe apnoea prediction. In other embodiments, the safe apnoea calculator 1204 uses the equilibrium prediction in combination with any of the other parameters described herein in making the prediction. In yet further embodiments, the safe apnoea calculator 1204 does not use the initial equilibrium prediction, and only uses one or more of the other pre-operative measurements/inputs in making the prediction. In some embodiments, the safe apnoea calculator uses one or more of BMI, a ratio of $PaO_2$ and BMI (e.g., $PaO_2$ to BMI), BMI distribution, and BSI in making the prediction, but does not directly use an equilibrium prediction.

For example, the respiratory equilibrium calculator 1202 can use any of the methods of FIGS. 15A-15C to generate the initial equilibrium prediction, and the safe apnoea calculator 1204 can similarly use any of the methods of FIGS. 15A-15C to generate the initial safe apnoea prediction.

The output 1206 can output information relating to one or more of the initial equilibrium prediction and the safe apnoea predictions to the user, including outputting the predicted equilibrium value, equilibrium duration, time to equilibrium, duration of safe apnoea prediction, or any related values on a display for the clinician to consider in planning the procedure.

The controller 1208 can use the predictions as feedback to control one or more devices. As just a few examples, the controller 1208 may increase the flow to the flow generator 102 in response to a predicted equilibrium value or equilibrium duration that is lower than desired, or in response to a predicted duration of safe apnoea that is shorter than desired.

At an initial stage 1210 of the operation one or both of the respiratory equilibrium calculator 1202 and the safe apnoea calculator 1204 receive one or more measurements/inputs relating to the patient. These can be any of the measurements/inputs described herein, including as just a few possible examples, $SpO_2$ measurements, $PaO_2$ measurements, $CO_2$ measurements, or any combination thereof, which may obtained by the physiological sensor module 121 of the system 100, for example.

The respiratory equilibrium calculator 1202 generates an updated equilibrium prediction at first stage 1210 using the measurements/inputs. For instance, in one illustrative implementation, the calculator 1202 uses BMI to generate the initial prediction at stage 1200 and uses monitored $PaO_2$ at the second stage 1210 to update and/or confirm the prediction made at the first stage 1200. The calculator 1202 may at stage 1210 generate an updated equilibrium prediction based on the slope 1102/1104 (FIGS. 11A/11B) of monitored $PaO_2$, for example. For instance, a steeper than predicted downward $PaO_2$ slope 1102/1104 may lead to a downward adjustment of the equilibrium value, and shallower than expected $PaO_2$ slope 1102/1104 may lead to an upward adjustment of the equilibrium value. The respiratory equilibrium calculator 1202 outputs the updated equilibrium prediction to one or more of the safe apnoea calculator 1204, the output 1206, and the controller 1208.

Similarly, the safe apnoea calculator 1204 generates an updated safe apnoea prediction and provides it to one or both of the output 1206 and the controller 1208.

Figure 13:
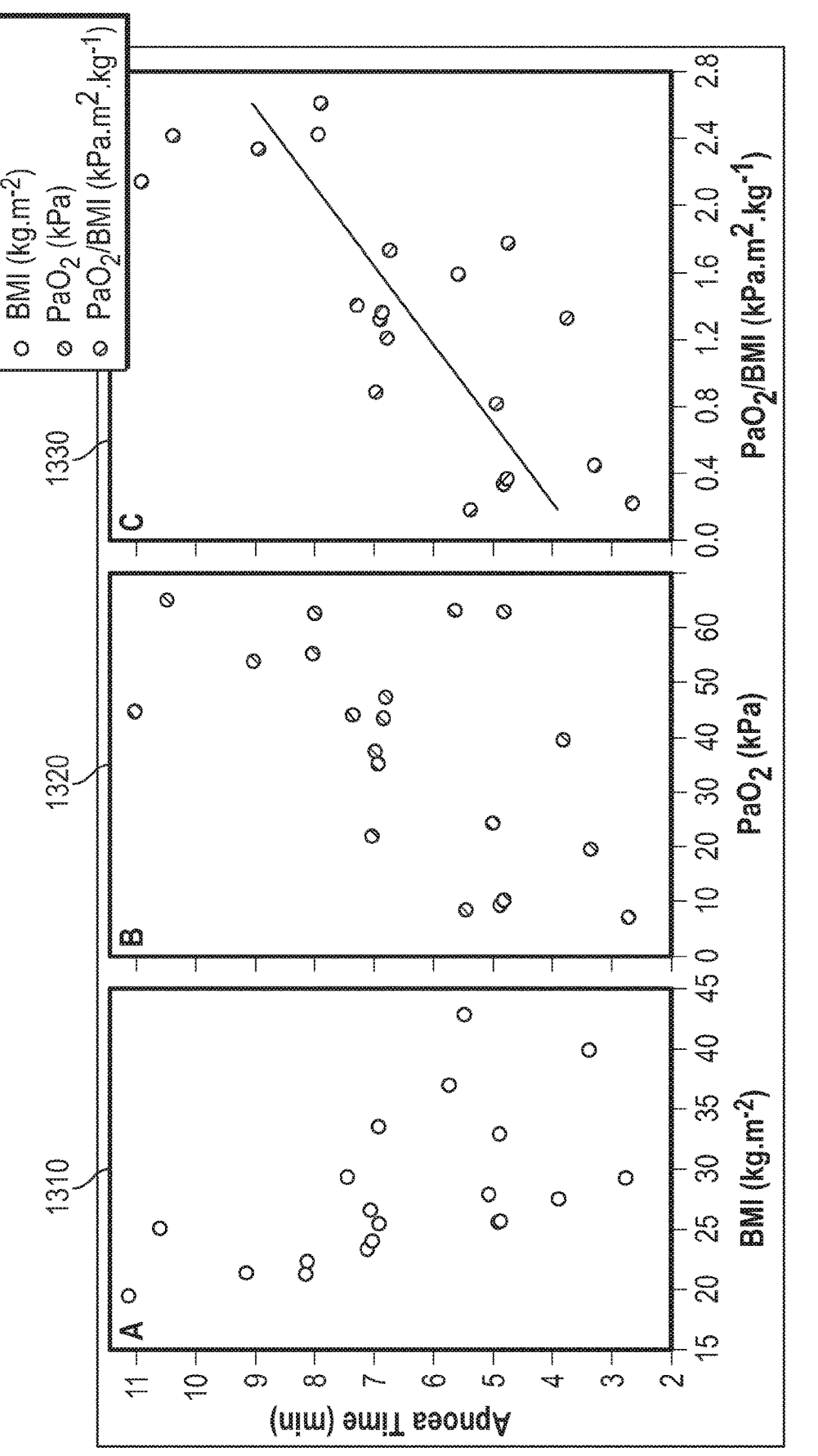
FIG. 13 shows plots, for a plurality of patients, of apnoea time versus body mass index (BMI), apnoea time versus $PaO_2$, and apnoea time versus a ratio of $PaO_2$ to BMI.

The safe apnoea calculator 1204 can generate the safe apnoea prediction using any combination of one or more of the updated equilibrium prediction and the other pre-operative measurements/inputs. For instance, a downwardly adjusted equilibrium value may correspond to an updated duration of safe apnoea that is shorter than the initial prediction, and an upwardly adjusted equilibrium value may correspond to an updated duration of safe apnoea that is longer than the initial prediction. In some implementations the safe apnoea calculator 1204 can make the safe apnoea prediction/update using a ratio of PaO2 to BMI. The authors conducted a randomised controlled trial of Transnasal Humidified Rapid-Insufflation Ventilatory Exchange (THRIVE) versus facemask oxygenation on a group of 40 patients. In a subgroup analysis of patients in the facemask group, it was shown that the ratio of PaO2 to BMI can be strongly correlated with apnoea time, FIG. 13 shows data plots for a plurality of patients from the subgroup analysis, including, for each patient, safe apnoea time versus BMI (1310), apnoea time versus $PaO_2$ (1320), and apnoea time versus a ratio of $PaO_2$ to BMI (1320). Each data point in the plots corresponds to a particular patient, with PaO2 values measured at the time of intubation. As shown at 1320, the ratio of PaO2 to BMI can be strongly correlated with apnoea time.

For example, during the initial stage of operation, the respiratory equilibrium calculator 1202 can use any of the methods of FIGS. 15A-15C to generate the updated equilibrium prediction based on appropriate measurements/inputs, and the safe apnoea calculator 1204 can similarly use any of the methods of FIGS. 15A-15C to generate the updated safe apnoea prediction based on appropriate measurements/inputs.

At stage 1210 the output 1206 can update the information provided to the user to reflect the updated equilibrium prediction, the updated safe apnoea prediction, or both, such as by updating the appropriate values on a display of the I/O 100.

Following the initial operation stage 1210, at an operation stage 1220, one or both of the respiratory equilibrium calculator 1202 and the safe apnoea calculator 1204 continue to receive one or more measurements/inputs relating to the patient. These can be any of the measurements/inputs described herein, including as just a few examples, $SpO_2$ measurements, $PaO_2$ measurements, $CO_2$ measurements, or any combination thereof, which may obtained by the physiological sensor module 121 of the system 100, for example.

The respiratory equilibrium calculator 1202 generates real-time equilibrium calculations at stage 1220 using the received measurements/inputs. For instance, the calculator 1202 at stage 1220 can monitor $PaO_2$, $SpO_2$ or any other appropriate parameter to further update the predicted equilibrium calculation, to monitor the actual observed equilibrium, or both. In one embodiment, the calculator 1202 observes the equilibrium using $SpO_2$ and/or $PaO_2$ measurements and compares the observed equilibrium to one or more of the $SpO_2$ and $PaO_2$ envelopes 1106, 1108 (FIG. 11B), as described previously.

Similarly, the safe apnoea calculator 1204 generates real time safe apnoea calculations at stage 1220 using the real-time equilibrium and/or the received measurements/inputs. For instance, the calculator 1204 may generate a real-time update of the duration of safe apnoea in response to a real-time observed value of the observed equilibrium received from the respiratory equilibrium calculator 1202. Or the calculator 1204 may update the duration of safe apnoea in response to a change in the observed slope $PaO_2$ slope 1102/1104 (FIGS. 11A/11B) or other appropriate measured values.

"Before operation" and "pre-operative" as used herein and in the context of FIG. 12 can in some implementations mean any combination of one or more of before anaesthetic has been administered, before anaesthetic has taken significant effect, or before the planned medical procedure (e.g., intubation, surgery, etc.) has taken place.

"Initial stage of operation" as used herein and in context of FIG. 12 can in some implementations can correspond any combination of one or more of the following time periods: any portion of the time period from when anaesthetic is administered to when the anaesthetic has taken substantially full effect or apnoea is induced, any portion of the time period from when a physiological sensor module 121 begins to monitor the patient in the operating room to when the anaesthetic takes substantially full effect or apnoea is induced, any portion of the time period from when anaesthetic is administered until respiratory equilibrium is reached, and any portion of the time period from when anaesthetic is administered until when an intubation or other procedure begins.

"During operation" as used herein and in the context of FIG. 12 can mean any time after from completion of the initial operation stage until completion of the medical procedure, or from completion of the initial operation stage 1210 until cessation of physiological monitoring of the patient following completion of the operation.

Determining Blood Gases $CO_2$ and/or $O_2$ Level Progression and Equilibrium

Because blood gas levels, such as blood gas $CO_2$ levels (e.g., $PaCO_2$) and/or $O_2$ (e.g., $SpO_2$ or $PaO_2$) levels can be useful indications of duration of safe apnoea and/or apnoeic respiratory equilibrium, it can be useful to predict or determine blood gas level progression. For example, it can be useful to simulate predicted $CO_2$ or $O_2$ levels for an upcoming medical procedure or other apnoeic conditions, determine such levels in real-time using measured data, or update previous predictions using real-time measurements.

FIGS. 15A-15C show examples of methods of determining blood gas $CO_2$ (FIG. 15A) and/or $O_2$ levels (FIGS. 15A-15C) during a medical procedure or other apnoeic conditions. For example, the methods can be used predict blood gases progression in a patient before a procedure in which a patient will be apnoeic (e.g., due to intubation). The methods can also be used to better predict blood gases level progression during the procedure using real-time measurements, or to update previously predicted values.

According to certain embodiments, the methods assumes one or more of the following conditions are present:

The patient is in a state of approximate gaseous equilibrium with small gradients between different body compartments.

The lungs may have an amount of shunt where minimal or no gas exchange takes place.

There is minimal or no restriction to oxygen transport from the pharynx to the lungs.

$CO_2$ transport from the lungs to the pharynx is determined by the gas exchange volume dependent on physiological factors which include cardiogenic action.

Nitrogen is transported from the lungs to the pharynx by the same mechanism as $CO_2$, dependent on physiological factors which include cardiogenic action.

There is a defined relationship between arterial pH and $PaCO_2$ (e.g. a straight line with a negative gradient).

The methods can be implemented in whole or in part by the controller 108 or some other processor of either the system 100 of FIG. 1 or the system 300 of FIG. 3, for example, or by one or more other processors. The methods will be described in certain places with reference to the system 300 of FIG. 3 merely for the purposes of illustration. Where an "amount" of a particular substance such as $CO_2$ or $O_2$ is discussed, units may or may not be specifically called out, but it will be appreciated that the amount can be in any appropriate unit including moles or in volume units (e.g., litres), without limitation. The methods of FIG. 15A-15C are described in the context of a patient is apnoeic during the entirety of the measured time period ($t_1$-$t_i$). In other embodiments, the patient may be apnoeic during only a portion of $t_1$-$t_i$.

At step 1502 the method of FIG. 15A includes determining the total amount of $CO_2$ stored in a patient at the beginning of a current time interval ($t_n$) in a medical procedure (e.g., beginning of apnoea) or other condition which the patient may become apnoeic. According to an illustrative embodiment, the total amount of $CO_2$ is obtained based on a starting $PaCO_2$ value for the patient at $t_n$.

When current time period is the first time period ($t_n = t_1$) corresponding to the start of apnoea, the starting $PaCO_2$ value can be a static value for all patients, e.g., based on average patient data. In such a case the starting $PaCO_2$ value can be pre-loaded in the memory 134 for access by the controller 108, for example, or provided to the controller 108 by a user via the I/O 110. In other cases, the controller 108 can derive the starting PaCO2 value at $t_1$ from other inputs. For example, the controller 108 can look up the starting $PaCO_2$ from a table or other database using one or more patient parameters (e.g., weight, height, gender, age, BMI, or any of the other parameters described herein). In yet further embodiments, the $PaCO_2$ is obtained from direct measurement, such as from blood sample analysis.

However obtained, the starting $PaCO_2$ value at $t_1$ is used in the illustrative embodiment to determine the total amount of stored $CO_2$ in the patient at $t_1$ via a relationship table or database that relates $PaCO_2$ values to values of total amount of stored $CO_2$. The table can be derived by calculating the CO2 stored in the patient as a function of $PaCO_2$ using one or more of a variety of possible patient parameters as inputs, such as body mass, weight, height, gender, age, lung functional residual capacity (FRC), lung volume, solubility of $CO_2$, percentage of water in the patient's body excluding blood, percentage of blood $CO_2$ in haemoglobin, and blood volume. The patient parameters used to generate the table or database can be referenced to a population dataset, and in some embodiments the method can include collecting patient data during a medical procedure to form the population dataset.

Certain values in the table can additionally be derived using one or more known relationships, such as a clinically or otherwise determined relationship between pH and $PaCO_2$, Dalton's law of partial pressures, the ideal gas law for $CO_2$ stored as gas in the lung volume, an assumption that a certain percentage of blood $CO_2$ is stored in haemoglobin, etc.

The above-described and/or other inputs and relationships can be used to derive a relationship table. For example, amounts of $CO_2$ in various body compartments (e.g., without limitation, amounts dissolved in body, existing as bicarbonate, in haemoglobin, in lungs, existing in body water, etc.) can be calculated for a given $PaCO_2$ value and summed together to provide an estimated total amount of moles of $CO_2$ in the body, which can in turn be converted (e.g., using the ideal gas law) into a total estimated volume $CO_2$. A blood pH value (see step 1512) can be used in calculating an amount of $CO_2$ existing as bicarbonate in the blood, for example. The amounts of $CO_2$ in various body compartments can be determined using the $PaCO_2$ value in combination with various other appropriate inputs. The values in such a table can be pre-populated and stored in the memory 134, can be entirely calculated by the controller 108 (e.g., prior to a medical procedure), or can be pre-populated but updated in real-time using measured parameters (e.g., temperature or pressure readings or patient data such as weight, height, or the like).

At step 1504, the method includes calculating an estimated total amount of $CO_2$ (e.g., $CO_2$ volume) that will be produced in the patient over the current time interval ($t_n$). For example, for initial time interval $t_1$ the controller 108 can determine the total estimated amount of $CO_2$ that will be produced based on calculating a rate of production of $CO_2$ using a given respiratory exchange ratio or rate for the patient, and an assumed initial rate of oxygen consumption or metabolic rate of the patient.

At step 1506, the method includes subtracting the estimated amount of $CO_2$ that will be cleared over $t_n$ from the estimated total estimated $CO_2$ produced calculated at step 1504, to determine estimated total net $CO_2$ that will be added to the patient over $t_n$. The $CO_2$ clearance rate can generally be based on one or more of the patient's cardiogenic action (which can be measured or assumed) and $CO_2$ concentration in the patient's lungs (which can be measured or assumed). For example, the controller 108 can determine the amount of $CO_2$ cleared over $t_n$ based on an assumed or measured gas exchange ratio due to cardiogenic action of the patient. For example, changes in amplitudes of cardiogenic oscillations over time can be used as an input to determine $CO_2$ clearance, which can impact $PaCO_2$ progression and blood pH, which in turn affects $O_2$ progression levels.

Depending on the embodiment, the $CO_2$ clearance rate for one or more of the time intervals $t_1$-$t_i$ can be obtained from a population dataset, measured, estimated, or calculated. The $CO_2$ clearance rate can be based on one or more characteristics of the respiratory therapy or other gases flow provided to the patient. For example, in the illustrative embodiment, the patient is additionally subject to a respiratory support provided by the flow generator 102, which increases the $CO_2$ clearance rate. In some embodiments, the respiratory support is a high flow respiratory support. Thus, the controller 108 accounts for this enhanced clearance rate (which can be pre-determined or measured or otherwise determined in real-time) when calculating the amount $CO_2$ cleared over $t_n$. For example, the clearance rate can be updated using real-time measurements taken using the sensor 120 or the physiological sensing module 121. The respiratory therapy can be any of those described herein, or some other flow of gases provided to the patient. In one embodiment, an estimated $CO_2$ clearance rate is determined based on the Transnasal Humidified Rapid-Insufflation Ventilatory Exchange (THRIVE) referenced above.

The gases flow provided to the patient can be at any of the following flow rates: about 5 litres/minute to about 150 litres/minute; about 20 litres/minute to about 90 litres/minute (which can correspond to a range of clearance values for an average adult population); about 0.4 litres/minute/kilogram to about 8 litres/minute/kilogram, with a minimum of about 0.5 litres/minute and a maximum of about 25 litres/minute (which can correspond to a range of clearance values for infant, premature, and/or paediatric populations); or at any of the other flow rates or ranges of flow rates described herein. Preferably, the gases flow provided to the patient is at flow rates of about 40 litres/minute to about 70 litres/minute.

Moreover, the characteristics of the gases flow can include one or more of a flow rate, pressure, and humidity of the gases flow.

At step 1508, the method includes adding the total estimated net amount $CO_2$ produced over $t_n$ (determined at step 1506) to the estimated total initial amount $CO_2$ stored (determined at step 1502) to determine estimated total $CO_2$ that will be stored in the patient at the end of $t_n$, which is the beginning of the next time interval ($t_{n+1}$). The total amount (e.g., volume) of $CO_2$ can be referred to as an "intermediate" $CO_2$ parameter because it is calculated between and used in the $PaCO_2$ calculations.

At step 1510, the method includes determining the predicted PaCO2 value at the end of $t_n$, which will be used in time period $t_n 1$. For example, the controller 108 can use the Table 1 to lookup the $PaCO_2$ value ($A_n$) corresponding to the total amount of $CO_2$ ($H_n$ or $G_n$) determined at step 1508.

At step 1512 the method includes determining a pH of the patient's arterial blood based on the determined $PaCO_2$ at the beginning of $t_n$. For example, the controller 108 can determine the pH using a known relationship between $PaCO_2$ and pH. The pH level can be used in calculating a $CO_2$ or $O_2$ level progression. Further steps for calculating a $O_2$ level progression will be described with respect to FIGS. 15B and 15C. The method can also include calculating a pH level for use in determining the $CO_2$ progression level, according to certain embodiments. The pH level can be referred to as a "correction factor" because it can be used to correct or otherwise determine a blood gases level (e.g., blood gases $O_2$ or $CO_2$) level (see, e.g., steps FIG. 15C).

Where the method includes determining a $CO_2$ progression level, the method can additionally include moving to step 1514 to determine an updated rate of rise of $PaCO_2$. For example, the controller 108 calculates the difference between the value of $PaCO_2$ at beginning of $t_n$ (determined at step 1502) and the predicted value of $PaCO_2$ at the end of $t_n$ (beginning of $t_{n+1}$) (determined at step 1510), and divides it by the time interval duration to determine the updated rate of $PaCO_2$ rise. In certain embodiments, this step is performed when the real-time patient monitoring data is used in performance of the method, and can optionally be omitted in some other situations where real-time patient monitoring data is not used and the method is solely predictive.

At step 1516, the method calculates an updated $CO_2$ production rate. For example, the processor can calculate the updated $CO_2$ production rate by differentiating the table of $PaCO_2$ vs. total amount $CO_2$ (e.g., from Table 1), and using: 1) the differentiated table, 2) the determined rate of rise of $PaCO_2$ (determined at step 1514), and 3) the $PaCO_2$ value at $t_n$ to calculate a new rate of $CO_2$ storage. In some embodiments, the updated $CO_2$ storage rate corresponds to the updated $CO_2$ production rate. In some embodiments, the updated $CO_2$ storage rate corresponds to the difference between the updated $CO_2$ production rate and a $CO_2$ clearance rate. The $CO_2$ clearance rate may be based on one or more of the patient's cardiogenic action (which can be measured or assumed) and $CO_2$ concentration in the patient's lungs (which can be measured or assumed) In some of such embodiments, the patient may be apnoeic and a gases flow is provided to the patient. Where a gases flow is provided to the patient, the $CO_2$ clearance rate may be based on one or more characteristics of the respiratory therapy or other gases flow provided to the patient. The updated $CO_2$ production rate will be used during $t_{n+1}$, to estimate total amount $CO_2$ produced over $t_{n+1}$ (at the next iteration of step 1504).

Depending on the embodiment, the method can include calculating an $O_2$ level progression, a $CO_2$ level progression, or both. Where the method includes calculating an $O_2$ progression level, the method can include moving to step 1530 shown of FIG. 15B, or step 1560 of FIG. 15C, which will be described below.

Otherwise, e.g., when calculating a $CO_2$ level progression and not an $O_2$ level progression, the method can include at step 1518 iterating some or all of step 1502 through step 1516 for each of the subsequent time periods $t_{n+1}$ to $t_i$ (end of procedure and/or apnoea), thereby predicting a simulated progression of $PaCO_2$ values from $t_1$ to $t_i$.

Notably, after $t_1$, for subsequent time periods ($t_2$-$t_i$), the $PaCO_2$ of the patient at the beginning of current time period ($t_n$) is the $PaCO_2$ calculated at step 1510 during the previous time period ($t_{n-1}$). Thus, for $t_2$-$t_i$ at step 1502 the controller 108 can retrieve a stored value of $PaCO_2$ calculated at step 1510 during $t_{n-1}$.

Similarly, for $t_2$-$t_i$, the $CO_2$ production rate for the current time period ($t_n$) is the updated $CO_2$ production rate calculated at step 1516 at $t_{n-1}$. Thus, for $t_2$-$t_{is}$ at step 1504 the controller 108 can retrieve a stored value of the updated $CO_2$ production rate calculated at step 1516 during $t_{n-1}$. In various embodiments, the $CO_2$ production rate during $t_2$-$t_1$ can be based on one or more of the following inputs: a respiratory exchange ratio or rate of the patient, a metabolic rate or oxygen consumption rate of the patient, a temperature of the patient, a volume of the patient's blood, body fluids, or lungs; a blood $PaCO_2$ or blood pH of the patient or associated parameter thereof, or a haemoglobin concentration in the patient's blood. Moreover, some or all of these inputs can be obtained using real-time measurements, e.g., using the sensor 120 or the sensor.

According to certain embodiments, the methods of FIGS. 15A-15B can be carried out entirely before a medical procedure. In other cases, the methods can be carried out at least partly during a medical procedure, such as where one or more of the $PaCO_2$ values or the values for the total amount of stored $CO_2$ are determined using real time measurements (e.g., measured $PaCO_2$ values, cardiac action [e.g., heart rate which can impact clearance], $O_2$ consumption which can impact metabolic rate, pH from blood gas analysis, or airway patency estimates which can affect how effective cardiac action is at clearing $CO_2$).

Figure 16A:
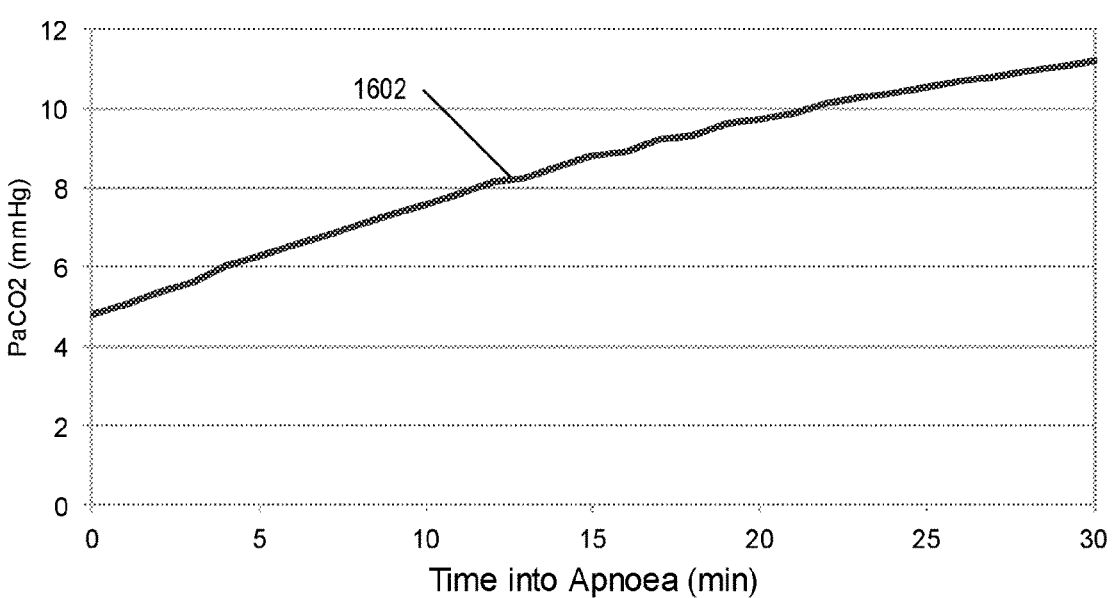
FIG. 16A shows an example of a plot of predicted $PaCO_2$ levels during apnoea, where the $PaCO_2$ levels are determined using the method of FIG. 15A.
Figure 16B:
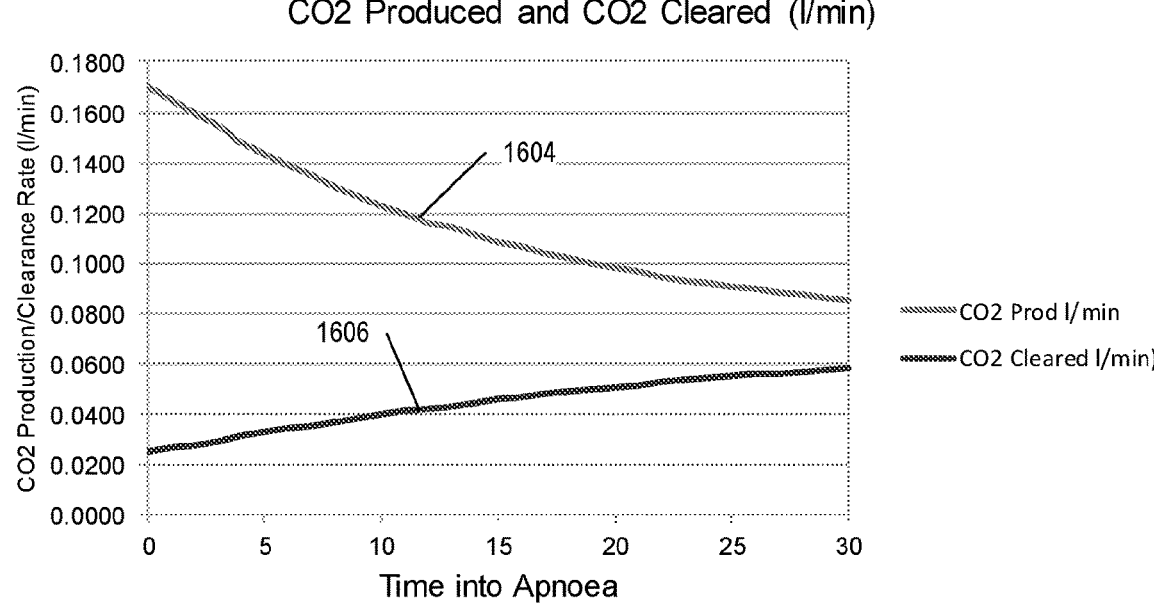
FIG. 16B shows plots of volume of $CO_2$ produced and volume of $CO_2$ cleared during apnoea, where the values are determined using the method of FIG. 15A.

FIG. 16A shows an example of a plot 1602 of predicted $PaCO_2$ time over a 30 minute period of apnoea, where the $PaCO_2$ values are determined using the method of FIG. 15A. FIG. 16B shows plots of volume of $CO_2$ produced 1604 and volume of $CO_2$ cleared 1604 over a 30 minute period of apnoea, where the values are determined using the method of FIG. 15A.

The method of FIG. 15A can further include at step 1520 determining a parameter related to a respiratory equilibrium and/or a duration of safe apnoea based on blood gases $CO_2$ information determined during steps 1502-1518. For example, the method can include determining one or more of the following parameters relating to a respiratory equilibrium:

A $PaCO_2$ level at or during respiratory equilibrium where the CO2 production rate and the CO2 clearance rate are substantially the same or the difference between the two is less than a predetermined threshold, which can provide an indication that the patient is in respiratory equilibrium has been reached;

a time point into apnoea when the $CO_2$ production rate and the $CO_2$ clearance rate are substantially the same or the difference between the two is less than a predetermined threshold, which can provide an indication that the patient is in respiratory equilibrium has been reached;

a length of time during which the $CO_2$ production rate and the $CO_2$ clearance rate are substantially the same or the difference between the two is less than a predetermined threshold, which can provide an indication as to how long respiratory equilibrium and/or safe apnoea is likely to last; and a time point when the CO2 production rate is substantially greater than the $CO_2$ clearance rate and the $CO_2$ production rate is greater than or equal to a predetermined threshold, which can provide an indication as to when the patient will become dangerously hypercapnic.

The predetermined thresholds can be set by a user, for example, or pre-loaded into the memory 134.

According to certain embodiments, the $CO_2$ production rate and the $CO_2$ clearance rate are substantially the same when a difference between the CO2 production rate and the CO2 clearance rate falls within a predetermined tolerance range. Conversely, the $CO_2$ production rate according to some embodiments is substantially greater than the $CO_2$ clearance rate when a difference between the CO2 production rate and the CO2 clearance rate falls outside a predetermined tolerance range.

At step 1520 the method can additionally determine a duration of safe apnoea based on blood gases $CO_2$ information. For example, the processor 108 can determine a duration of safe apnoea that includes the length of time until reaching the time point when the $CO_2$ production rate is substantially greater than the $CO_2$ clearance rate and the $CO_2$ production rate is at the predetermined threshold. Such a circumstance may occur, for example, when there is an airway blockage. In some embodiments, the duration of safe apnoea includes the length of time until a predetermined $PaCO_2$ threshold is reached.

In various embodiments, one or more parameters related to a respiratory equilibrium or duration of safe apnoea can be determined from values calculated using the method of FIG. 15A. For example, the controller or other appropriate component can use one or more of the $PaCO_2$ values (determined at step 1510) or other values calculated using the method of FIG. 15A to determine one or more properties associated with a respiratory equilibrium or duration of safe apnoea using any of the techniques described herein, including those described with respect to FIGS. 4, 6-10, 11A-11D, and 12.

While the method of FIG. 15A has been described in the context of determining $PaCO_2$, in other embodiments different $CO_2$ blood gas parameters can be determined using the method of FIG. 15A, such as $PvCO_2$ or end tidal $CO_2$ ($EtCO_2$), or other parameters relating to venous or arterial carbon dioxide content. For example, $EtCO_2$ can be measured by detecting gases coming out of the patient (e.g., the sensor 120).

FIGS. 15B and 15C show portions of two different techniques for determining blood gas $O_2$ levels during a medical procedure or other apnoeic conditions. In particular, FIG. 15B shows a technique where the $O_2$ level calculation (steps 1530-1548) for each time period $t_n$ generally follows sequentially from the $CO_2$ level calculation (steps 1502-1516).

On the other hand, FIG. 15C shows an alternative technique where the method includes generating a lookup table at step 1522 (see below) for use in determining the $O_2$ levels (steps 1560-1578) for each time period $t_n$. According to such an alternative technique, the lookup table allows the $O_2$ level progression to be determined at some later point in time, disconnected from the $CO_2$ and pH level calculations, as will be explained in greater detail with respect to FIG. 15C.

Referring now to FIG. 15B, continuing from step 1516 (FIG. 15A), at step 1530 the method includes calculating a shift in p50 (the partial pressure of $O_2$ required to achieve 50% haemoglobin saturation) using the blood pH value obtained at step 1512. In some embodiments, step 1530 further includes calculating the shift in p50 using the patient temperature and/or 2,3-diphosphoglyceric acid concentration in the patient's blood. For example, the method can include applying a Bohr shift of the oxygen-haemoglobin dissociation curve using the blood pH obtained at step 1512 to calculate the shift in p50. As one example, the controller

108 uses the following equation to calculate a shift in p50 from its normal value at pH=7.4 in the Hills equation to the p50 value at the pH value obtained from step 1512:

$$\frac{\Delta \log(p50)}{\Delta(\text{pH})} = -0.5$$

At step 1532, the method includes calculating the alveolal partial pressure of $O_2$ (alveolal $PO_2$). For example, according to certain embodiments, the controller 108 calculates the aveolal partial pressure of $O_2$ based on at least one of an i) amount of $FiO_2$ supplied to the patient, corrected for the partial pressure of water vapour assuming 100% saturation at the patient temperature, and ii) alveolal partial pressure of $CO_2$ (assume alveolal $PCO_2$ is equal to the $PaCO_2$ which could be obtained from the method of FIG. 15A). For example, with respect to i), the calculation of aveolal partial pressure of $O_2$ can be based on one or more characteristics of $FiO_2$ or other gas flow provided to the patient, such as percentage of oxygen or flow rate. For instance, the controller 108 can determine the patient's $FiO_2$ based on a gases flow provided to the patient. In certain, embodiments, the gases flow comprises an $O_2$ percentage of about 15% to about 100%. The method can include administering $FiO_2$ in any of the manners described herein.

At step 1534, the method includes using the shifted p50 value in Hills equation (determined at step 1530) and the calculated alveolal $PO_2$ level (determined at step 1532) to calculate the saturation of the patient's blood at the alveolal $PO_2$ level using Hills Equation. This calculation can assume that the arterial blood is in gaseous equilibrium with the $O_2$ in the alveoli. In some embodiments, the method can additionally include applying a factor to account for the oxygen transfer efficiency across the alveolal membrane.

At step 1536, the method includes calculating the concentration of $O_2$ per unit volume of oxygenated blood. For example the controller 108 can execute the calculation using: 1) the saturation of the patient's blood at the aveolal $PO_2$ level (determined at step 1534), the concentration of Haemoglobin in the blood, and the capacity of the Haemoglobin to calculate the concentration of O2 per unit volume of oxygenated blood. The concentration of Haemoglobin in the blood and the capacity of the Haemoglobin can be retrieved from a database stored in the memory 134 or obtained from measurements, e.g., using the physiological sensing module 121. For example, the values can be estimated based on certain patient factors, e.g. age, weight/volume of blood, gender, or determined by taking a blood sample and using known techniques (e.g. HiCN method, blood gas analyzer) to determine the amount of Hb in that blood sample and extrapolating that based on the patient's blood volume (using possibly weight) to obtain the concentration of Hb in the patient's blood.

At step 1538, the method includes calculating the diluted $O_2$ concentration when venous blood at low saturation is mixed with oxygenated blood. This can include factoring in a level of shunt/V/Q mismatch in the patient's lungs. For example, when the patient experiences shunt in the lungs, blood passing some parts of the lung is not oxygenated and when it mixes with oxygenated blood, dilutes the $O_2$ concentration in the blood leaving the lungs. Because the level of shunt can change during the progression of apnoea/medical procedure, step 1538 can include measuring a rate of change of shunt and using it to calculate the diluted $O_2$ concentration. Factors that could affect shunt can include disease state, position of patient during the procedure, medication, BMI, or BSI.

At step 1540, the method includes calculating the mixed arterial oxygen saturation ($SaO_2$) from the $O_2$ concentration levels in non-shunted and shunted blood. For example, the controller 108 can calculate the $SaO_2$ from diluted oxygen concentration (determined at step 1538). In some embodiments, the controller 108 can further apply Hills equation in reverse (with shifted p50) to calculate the arterial $PaO_2$ from the arterial $SaO_2$ at step 1540.

At step 1542 the method includes calculating the rate at which $O_2$ is transported to the patient's tissues using the patient's cardiac output and arterial $O_2$ saturation (determined at step 1540). Depending on the embodiment, the controller 108 can obtain the patient's cardiac output from real-time measurements taken using the physiological sensing module 121, or from a population dataset stored in a database in the memory 134. In some cases, cardiac output can be calculated at least in part based on knowledge that a pharmacological substance has been administered to the patient (e.g., a drug affecting cardiac output). Cardiac output can additionally be determined based on a patient's BMI or BSI.

At step 1544 the method includes calculating the current $O_2$ consumption rate. For example, the controller 1508 can perform the calculation using the current CO2 production rate (FIG. 15A step 1516) and a respiratory exchange rate, which can be obtained via real-time measurements, from a population dataset, or in any of the other manners discussed above.

At step 1546, the method includes calculating venous $O_2$ concentration (of blood leaving the tissues) based on the arterial $O_2$ concentration (of blood arriving at the tissues) and the $O_2$ consumption rate (determined at step 1544).

At step 1548, the method includes calculating the venous $O_2$ saturation ($SvO_2$) from the venous $O_2$ concentration (determined at step 1546). For example, the controller 108 can calculate venous $O_2$ saturation ($SvO_2$) from the venous $O_2$ concentration by applying Hills equation in reverse (with shifted p50). For example, at step 1548 the controller 108 can access a table or other database of a pH vs. Bohr-shifted dissociation curve. The curve can be generated based on patient parameters measured using the physiological sensor module 121 or another sensor. Or, in other embodiments, because the relationships represented in such a database can be generally similar amongst certain patient populations, the database can be generated from a population dataset. In various embodiments, the table can be generated based on one or more of the following, without limitation: patient haemoglobin concentration, patient cardiogenic gas exchange, patient cardiac output, patient metabolism (at rest and/or during procedure), patient $O_2$ storage efficiency of haemoglobin, and patient disease status. Some or all of these may be measured before or during the procedure, or can be assumed based on patient population data, depending on the embodiment. Determined values of venous oxygen saturation ($PvO_2$) and/or the partial pressure of oxygen in the venous blood ($PvO_2$) can be used as an input in the next iteration to determine the diluted O2 concentration when venous blood at low saturation is mixed with oxygenated blood at step 1538, particularly when there is shunt.

At step 1550, the method can include iterating some or all of steps 1502 through step 1516 (FIG. 15A) and 1530 through 1548 (FIG. 15B) for each of the subsequent time periods $t_{n+1}$ to $t_i$ (end of procedure and/or apnoea), thereby predicting a simulated progression of $CO_2$ values (e.g., $PaCO_2$ values) and $O_2$ (e.g., $SpO_2/SaO_2$, $PaO_2$, $SvO_2$, and/or $PvO_2$ values) from $t_1$ to $t_i$. While in such a case the illustrated techniques for determining $CO_2$ progression and $O_2$ progression can be performed together, the techniques are independent and in other embodiments the can be used to predict only $CO_2$ level progression or only $O_2$ level progression.

For the purposes of illustration, the method of obtaining oxygen level progression shown in FIGS. 15A-15B has been described with respect to certain examples that determine and/or use certain oxygen-related parameters. However, depending on the embodiment, the method can determine and/or use a variety of oxygen-related parameters, including $SpO_2$, $PaO_2$, $SvO_2$, or $PvO_2$.

The method can further include at step 1552 determining a parameter related to a respiratory equilibrium and/or a duration of safe apnoea based on blood gases $O_2$ information determined during one or more of the steps 1502-1516 and 1530-1550. For instance, the determined progression of $SpO_2$ and $PaO_2$ over time can help predict/determine parameters associated with respiratory equilibrium, such as when equilibrium is reached, at what $SpO_2/PaO_2$ level equilibrium is reached, how long equilibrium may last for, the time point when equilibrium ends (such as if there is a change in the patient's status or in a medical procedure that could impact the equilibrium). Moreover, from such information safe apnoea can be determined. Or safe apnoea can be determined based on clinician input, such as setting of a set maximum period of time to be kept at equilibrium (e.g., no more than 10 minutes).

For example, one or more of the arterial $O_2$ saturation level (determined at step 1540), venous $O_2$ saturation level (determined at step 1548), or other $O_2$ related values can be used to determine one or more properties associated with a respiratory equilibrium or duration of safe apnoea in a variety of the manners. For instance, the controller 108 or other appropriate component can calculate such respiratory equilibrium or duration of safe apnoea properties can be determined using any of the techniques described herein, including those described with respect to FIGS. 4, 6-10, 11A-11D, and 12.

As indicated, in certain other embodiments, instead of sequentially iterating 1502-1516 and then 1530-1548, the method instead determines a lookup table storing the relationship over time between pH values and the shifted p50 values and, using this table, the method can then calculate oxygen saturation related parameters (e.g., $SpO_2$, $PaO_2$, $SvO_2$, or $PvO_2$) over time. According to such embodiments, referring again to FIG. 15A, instead of moving to step 1530 (FIG. 15B), the method performs step 1518 to iterate some or all of steps 1502-1516, thereby generating pH blood values for each $PaCO_2$ level at each time interval $t_n$.

At step 1522, the method includes calculating the shift in p50 for each pH calculation previously determined at step 1512, for each time period $t_n$. For example, the controller 108 can store the pH values in the memory 134 at step 1512, and later retrieve the stored pH values at step 1522 and use them to calculate the shift in p50 for each pH value, e.g., according to a similar approach described with respect to step 1530 of FIG. 15B. The pH values and corresponding shifts in p50 can be stored in a lookup table. In various embodiments, the table can additionally be generated based on one or more of the following, without limitation: patient haemoglobin concentration, patient cardiogenic gas exchange, patient cardiac output, patient metabolism (at rest and/or during procedure), patient $O_2$ storage efficiency of haemoglobin, and patient disease status. Some or all of these may be measured before or during the procedure, or can be assumed based on patient population data, depending on the embodiment The lookup table can be used, e.g., at later point in time to predict or determine a progression of $O_2$ levels. For instance, referring to FIG. 15C, at step 1560 the method can further include accessing the lookup table to obtain the shifted p50 value for the previously predicted and stored pH level corresponding to each time period $t_n$.

The method can then include for time period $t_n$ performing some or all of steps 1562-1578, which can be generally similar to or the same as steps 1532-1548, respectively. At step 1580, the method includes iterating steps 1560-1578 for time periods to obtain appropriate $O_2$ levels (e.g., $SpO_2$, $PaO_2$, $SvO_2$, or $PvO_2$ for the remaining time periods $t_{n+1}$ to $t_i$.

Some specific examples of determining duration of safe apnoea have been described above in conjunction with utilizing respiratory equilibrium information and other parameters. However, depending on the embodiment, any of the techniques for determining a duration of safe apnoea described herein may be used in conjunction with respiratory equilibrium information, and incorporating any of the outputs described herein.

Features from one or more of the above methods may be combined with features of one or more other methods. Additionally, more than one method may be used together during a process of respiratory support of a patient.

The described systems can be useful for patients that are not spontaneously breathing, are sedated, or have reduced respiratory drive due to anaesthesia.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The inventions may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory therapy system comprising:
a flow generator for providing a gases flow to a patient;
at least one processor in electronic communication with the flow generator, the at least one processor provided with instructions which, when implemented, cause the at least one processor to:
receive one or more physiological parameters associated with the patient;
calculate a predicted apnoeic respiratory equilibrium value of the patient based on the one or more physiological parameters, wherein the predicted apnoeic respiratory equilibrium value is an oxygen saturation value where an oxygen saturation of haemoglobin in the patient is predicted to be at a stable level for a period of time during apnoeic oxygen delivery to the patient; and
cause the flow generator to control the gases flow to the patient based at least in part on the predicted apnoeic respiratory equilibrium value; and
an electronic display which receives an output from the at least one processor and displays one or more properties associated with the predicted apnoeic respiratory equilibrium value.

2. The respiratory therapy system of claim 1, wherein the one or more properties associated with the predicted apnoeic respiratory equilibrium value include one or more of: a time to reach equilibrium, a duration of equilibrium, or a rate of decline till equilibrium.

3. The respiratory therapy system of claim 1, wherein the instructions, when implemented, further cause the at least one processor to: determine a duration of safe apnoea based on the predicted apnoeic respiratory equilibrium value.

4. The respiratory therapy system of claim 1, wherein the one or more properties associated with the predicted apnoeic respiratory equilibrium value comprise properties associated with oxygen saturation and/or carbon dioxide saturation.

5. The respiratory therapy system of claim 1, wherein the instructions, when implemented, further cause the at least one processor to: receive real-time patient data from one or more respiratory sensors and/or one or more physiological sensors.

6. The respiratory therapy system of claim 5, wherein the instructions, when implemented, further cause the at least one processor to: calculate an updated predicted apnoeic respiratory equilibrium value, cause the electronicdisplay to display one or more updated properties associated with the updated predicted apnoeic respiratory equilibrium value, determine an updated duration of safe apnoea, and/or determine one or more properties associated with an airway patency of the patient based on the real-time patient data.

7. The respiratory therapy system of claim 1, wherein the instructions, when implemented, further cause the at least one processor to: receive one or more safety parameters including at least one of: a threshold desaturation level or a threshold respiratory equilibrium duration.

8. The respiratory therapy system of claim 1, wherein the one or more physiological parameters associated with the patient comprise one or more of: a height, a weight, a neck circumference, a waist circumference, a hip to waist ratio, a body mass index (BMI), a BMI distribution, a body shape index (BSI), a body morphology indication, a lung volume, a cardiac output, an age, a pregnancy status, a difficult airway type, a medical history, disease characteristics, a treatment history, or gas flow characteristics.

9. The respiratory therapy system of claim 1, wherein the instructions, when implemented, further cause the at least one processor to:

determine a ventilation/perfusion (V/Q) mismatch for the patient based on the one or more physiological parameters associated with the patient; and determine, based on the V/Q mismatch, the one or more properties associated with the predicted apnoeic respiratory equilibrium value.

10. The respiratory therapy system of claim 9, wherein the V/Q mismatch for the patient is determined based on a correlation of a BMI of the patient with one or more of: a neck circumference, a BSI, a hip-to-waist ratio, a monitored $PaO_2$, or a blood gas concentration of the patient.

11. The respiratory therapy system of claim 1, wherein the instructions, when implemented, further cause the at least one processor to: compare or fit a model to the one or more physiological parameters associated with the patient to determine the one or more properties associated with the predicted apnoeic respiratory equilibrium value.

12. The respiratory therapy system of claim 1, wherein the instructions, when implemented, further cause the at least one processor to:

determine the one or more properties associated with the predicted apnoeic respiratory equilibrium value using a first parameter of the one or more physiological parameters associated with the patient; and calculate a duration of safe apnoea of the patient using a second parameter of the one or more physiological parameters associated with the patient.

13. The respiratory therapy system of claim 12, wherein the first parameter comprises: a BMI, a $PaO_2$, a blood gas concentration, or a cardiac output of the patient, and wherein the second parameter comprises: the $PaO_2$ or the blood gas concentration of the patient.

14. The respiratory therapy system of claim 1, wherein the one or more properties associated with the predicted apnoeic respiratory equilibrium value are determined based on one or more of: a ratio of a $PaO_2$ and a BMI of the patient, a ratio of a blood gas concentration and the BMI of the patient, or a ratio of a cardiac output and the BMI of the patient.

15. The respiratory therapy system of claim 1, wherein the instructions, when implemented, further cause the at least one processor to:

calculate a ratio of measured $PaO_2$, blood gas concentration, or cardiac output of the patient to a BMI of the patient; and compare or fit a model to the ratio to determine the one or more properties associated with the predicted apnoeic respiratory equilibrium value.

16. The respiratory therapy system of claim 1, wherein the instructions, when implemented, further cause the at least one processor to:

determine that the patient is atypical based on the one or more physiological parameters associated with the patient; and determine the one or more properties associated with the predicted apnoeic respiratory equilibrium value based on the atypical determination.

17. The respiratory therapy system of claim 1, wherein the predicted apnoeic respiratory equilibrium value is above or below a threshold desaturation level for the patient.

18. The respiratory therapy system of claim 1, wherein the stable level is when the oxygen saturation of haemoglobin in the patient has a rate of binding that is equal to a rate of release.

19. The respiratory therapy system of claim 1, wherein causing the flow generator to control the gases flow to the patient based at least in part on the predicted apnoeic respiratory equilibrium value, is based on receiving user input from a user via the electronic display.

20. The respiratory therapy system of claim 1, wherein the respiratory therapy system uses the predicted apnoeic respiratory equilibrium value as feedback to automatically control the gases flow to the patient.

21. The respiratory therapy system of claim 1, wherein causing the flow generator to control the gases flow to the patient based at least in part on the predicted apnoeic respiratory equilibrium value includes comparing the predicted apnoeic respiratory equilibrium value to a target value, and increasing a flow rate of the gases flow based on determining that the predicted apnoeic respiratory equilibrium value is lower than the target value.

* * * * *